(12) United States Patent
Braje et al.

(10) Patent No.: US 7,320,979 B2
(45) Date of Patent: Jan. 22, 2008

(54) N-[(PIPERAZINYL)HETARYL]ARYLSULFONA-MIDE COMPOUNDS

(75) Inventors: Wilfried M. Braje, Rintein (DE); Andreas Haupt, Schwetzingen (DE); Wilfried Lubisch, Heidelberg (DE); Roland Grandel, Dossenheim (DE); Karla Drescher, Dossenheim (DE); Hervé Geneste, Neuhofen (DE); Liliane Unger, Ludwigshafen (DE); Daryl R. Sauer, Trevor, WI (US); Sean C. Turner, Mannheim (DE)

(73) Assignee: Abbott GmbH & Co. KG., Wiesbaden (DE)

( * ) Notice: Subject to any disclaimer, the term of this patent is extended or adjusted under 35 U.S.C. 154(b) by 160 days.

(21) Appl. No.: 10/823,317

(22) Filed: Apr. 13, 2004

(65) Prior Publication Data
US 2006/0160809 A1    Jul. 20, 2006

Related U.S. Application Data

(60) Provisional application No. 60/462,782, filed on Apr. 14, 2003.

(51) Int. Cl.
  A61K 31/496   (2006.01)
  A61K 31/506   (2006.01)
  C07D 213/72   (2006.01)
  C07D 213/74   (2006.01)
  C07D 239/48   (2006.01)

(52) U.S. Cl. .............. 514/252.14; 514/253.01; 544/295; 544/360

(58) Field of Classification Search ............ 544/360, 544/295; 546/276.7; 514/252.14, 253.01, 514/338
See application file for complete search history.

(56) References Cited

U.S. PATENT DOCUMENTS

| | | | |
|---|---|---|---|
| 4,577,020 | A | 3/1986 | Gall |
| 5,958,923 | A | 9/1999 | Hellendahl et al. |
| 6,090,807 | A | 7/2000 | Hellendahl et al. |
| 6,172,227 | B1 * | 1/2001 | Xiang et al. ............ 544/326 |
| 6,342,604 | B1 | 1/2002 | Hellendahl et al. |
| 6,380,206 | B1 * | 4/2002 | Pamukcu et al. .......... 514/269 |
| 6,472,392 | B1 | 10/2002 | Starck et al. |

FOREIGN PATENT DOCUMENTS

WO    WO 03/002543 A1    1/2003
WO    WO 2004/058265 A    7/2004

OTHER PUBLICATIONS

Jones et al. Chemical Abstracts, vol. 141, No. 123654 (Abstract for WO 2004/058265, Jul. 15, 2004) (2004).*
Database Chemcats, Chemical Abstracts Service, Columbus, Ohio, US; XP002294060.
Willecomme, B.: Recherches dans la série de la pipérizine; Annales de Chimie, vol. 4, No. 6, 1969, pp. 405-428, XP009035691.
Bromidge et al; "5-Chloro-N-(4-methoxy-3-piperazine-1-yl-phenyl)-3-methyl-2-benzothiophenesulfonamide (SB-271046): A Potent, Selective, and Orally Bioavailable 5-HT6 Receptor Antagonist"; Journal of Medicinal Chemistry, American Chemican Society, Washington, D.C. US, vol. 42, No. 2, Jan. 28, 1999, pp. 202-205, XP002109186; ISSN: 0022-2623.

(Continued)

*Primary Examiner*—Emily Bernhardt
(74) *Attorney, Agent, or Firm*—Wood Phillips et al.

(57) ABSTRACT

The invention relates to N-[(piperazinyl)hetaryl]arylsulfonamide compounds of the general formula I

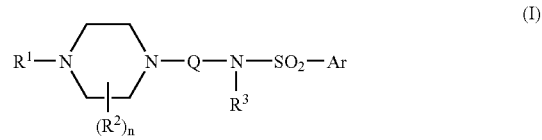

in which
Q is a bivalent, 6-membered heteroaromatic radical which possesses 1 or 2 N atoms as ring members and which optionally carries one or two substituents $R^a$ which is/are selected, independently of each other, from halogen, CN, $NO_2$, $CO_2R^4$, $COR^5$, $C_1$-$C_4$-alkyl and $C_1$-$C_4$-haloalkyl;
Ar is phenyl or a 6-membered heteroaromatic radical which possesses 1 or 2 N atoms as ring members and which optionally carries one or two substituents $R^b$, which is/are selected from halogen, $NO_2$, CN, $CO_2R^4$, $COR^5$, $C_1$-$C_6$-alkyl, $C_2$-$C_6$-alkenyl, $C_2$-$C_6$-alkynyl, $C_3$-$C_6$-cycloalkyl, $C_3$-$C_6$-cycloalkyl-$C_1$-$C_4$-alkyl and $C_1$-$C_4$-haloalkyl, with it also being possible for two radicals $R^b$ which are bonded to adjacent C atoms of Ar to be together $C_3$-$C_4$-alkylene;
$R^1$ is hydrogen, $C_1$-$C_4$-alkyl, $C_1$-$C_4$-haloalkyl, $C_3$-$C_6$-cycloalkyl, $C_3$-$C_6$-cycloalkyl-$C_1$-$C_4$-alkyl, $C_1$-$C_4$-hydroxyalkyl, $C_1$-$C_4$-alkoxy-$C_1$-$C_4$-alkyl, $C_3$-$C_4$-alkenyl or $C_3$-$C_4$-alkynyl;
with the radicals n, $R^1$, $R^2$, $R^3$, $R^4$ and $R^5$ having the meanings given in the patent claims, to the N-oxides and to the physiologically tolerated acid addition salts of these compounds and to pharmaceutical compositions which comprise at least one N-[(piperazinyl)hetaryl]arylsulfonamide compound as claimed in one of claims 1 to 10 and/or at least one physiologically tolerated acid addition salt of I and/or an N-oxide of I, where appropriate together with physiologically acceptable carriers and/or auxiliary substances for treating diseases which respond to influencing by dopamine $D_3$ receptor antagonists or agonists, in particular for treating diseases of the central nervous system and disturbances of kidney function.

22 Claims, No Drawings

OTHER PUBLICATIONS

Bromidge, S.M. et al; "Novel (4-piperazin-1-ylquinolin-6-yl) arylsulfonamides with high affinity and selectivity for the 5-HT6 receptor"; Bioorg. med. chem. Lett., vol. 11, 2001, pp. 2843-2846, XP002294076.

J.C. Schwartz, et al., The Dopamine $D_3$ Receptor as a Target for Antiphyschotics; Novel Antipsychotic Drugs, Raven Press, Ltd., 1992, pp. 135-144; France.

M. Dooley, et al., Pramipexole—A Review of Its use in the Management of Early and Advanced Parkinson's Disease; Drugs & Aging, 1998, vol. 12, pp. 495-514, New Zealand.

J.N. Joyce, Dopamine $D_3$ receptor as a therapeutic target for antiphyschotic and antiparkinsonian drugs; Pharmacology & Therapeutics, 2001, vol. 90, pp. 231-259, USA.

P. Solokoff, et al, Localization and Function of the D3 Dopamine Receptor; Arzneim-Forsch./Drug Res. vol. 42(1), 12992, pp. 224-230, France.

* cited by examiner

N-[(PIPERAZINYL)HETARYL]ARYLSULFONAMIDE COMPOUNDS

CROSS-REFERENCE TO RELATED APPLICATION

This application claims priority under 35 U.S.C. §119(e) to U.S. application Ser. No. 60/462,782, filed on Apr. 14, 2003.

The present invention relates to novel N-[(piperazinyl)hetaryl]arylsulfonamide compounds. The compounds possess valuable therapeutic properties and are suitable, in particular, for treating diseases which respond to modulation of the dopamine $D_3$ receptor.

Neurons obtain their information by way of G protein-coupled receptors, inter alia. A large number of substances exert their effect by way of these receptors. One of them is dopamine. Confirmed findings exist with regard to the presence of dopamine and its physiological function as a neurotransmitter. Disturbances in the dopaminergic transmitter system result in diseases of the central nervous system which include, for example, schizophrenia, depression and Parkinson's disease. These diseases, and others, are treated with drugs which interact with the dopamine receptors.

Up until 1990, two subtypes of dopamine receptor had been clearly defined pharmacologically, namely the $D_1$ and $D_2$ receptors. More recently, a third subtype was found, namely the $D_3$ receptor which appears to mediate some effects of antipsychotics and antiparkinsonians (J. C. Schwartz et al., The Dopamine $D_3$ Receptor as a Target for Antipsychotics., in Novel Antipsychotic Drugs, H. Y. Meltzer, Ed. Raven Press, New York 1992, pages 135-144; M. Dooley et al., Drugs and Aging 1998, 12, 495-514, J. N. Joyce, Pharmacology and Therapeutics 2001, 90, pp. 231-59 "The Dopamine $D_3$ Receptor as a Therapeutic Target for Antipsychotic and Antiparkinsonian Drugs").

Since then, the dopamine receptors have been divided into two families. On the one hand, there is the $D_2$ group, consisting of $D_2$, $D_3$ and $D_4$ receptors, and, on the other hand, the $D_1$ group, consisting of $D_1$ and $D_5$ receptors. Whereas $D_1$ and $D_2$ receptors are widely distributed, $D_3$ receptors appear to be expressed regioselectively. Thus, these receptors are preferentially to be found in the limbic system and the projection regions of the mesolimbic dopamine system, especially in the nucleus accumbens, but also in other regions, such as the amygdala. Because of this comparatively regioselective expression, $D_3$ receptors are regarded as being a target having few side-effects and it is assumed that while a selective $D_3$ ligand would have the properties of known antipsychotics, it would not have their dopamine $D_2$ receptor-mediated neurological side-effects (P. Sokoloff et al., Localization and Function of the $D_3$ Dopamine Receptor, *Arzneim. Forsch./Drug Res.* 42(1), 224 (1992); P. Sokoloff et al. Molecular Cloning and Characterization of a Novel Dopamine Receptor ($D_3$) as a Target for Neuroleptics, *Nature,* 347, 146 (1990)).

Compounds having an affinity for the dopamine $D_3$ receptor have been described in the prior art on various occasions, e.g. in WO 96/02519, WO 96/02520, WO 96/02249, WO 96/02246 and DE 10131543 and WO 99/02503. Some of these compounds possess high affinities for the dopamine $D_3$ receptor. They have therefore been proposed as being suitable for treating diseases of the central nervous system. Some of the compounds described in these publications possess a piperazinylhetaryl structure.

The invention is based on the object of providing compounds which act as selective dopamine $D_3$ receptor ligands.

This object is achieved by means of N-[(piperazinyl)hetaryl]arylsulfonamide compounds of the general formula I

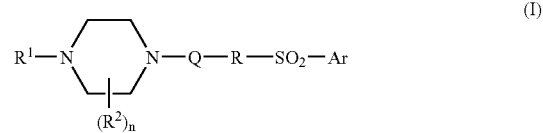

in which

R is oxygen, a group N—$R^3$ or a group $CR^{3a}R^{3b}$;

Q is a bivalent, 6-membered heteroaromatic radical which possesses 1 or 2 N atoms as ring members and which optionally carries one or two substituents $R^a$ which is/are selected, independently of each other, from halogen, CN, $NO_2$, $CO_2R^4$, $COR^5$, $C_1$-$C_4$-alkyl, $C_1$-$C_4$-alkoxy, $C_1$-$C_4$-haloalkyl, $NH_2$, $NHR^6$, $NR^6R^7$ and $C_1$-$C_4$-haloalkoxy;

Ar is phenyl or a 6-membered heteroaromatic radical which possesses 1 or 2 N atoms as ring members and which optionally carries one or two substituents $R^b$, which is/are selected from halogen, $NO_2$, CN, $CO_2R^4$, $COR^5$, $NH_2$, $NHR^6$, $NR^6R^7$, $C_1$-$C_6$-alkyl, $C_1$-$C_6$-haloalkyl, $C_1$-$C_6$-alkoxy, $C_1$-$C_6$-haloalkoxy, $C_2$-$C_6$-alkenyl, $C_2$-$C_6$-alkynyl, $C_3$-$C_6$-cycloalkyl, $C_3$-$C_6$-cycloalkoxy, $C_3$-$C_6$-cycloalkyl-$C_1$-$C_4$-alkyl and $C_1$-$C_4$-haloalkyl, with it also being possible for two radicals $R^b$ which are bonded to adjacent C atoms of Ar to be together $C_3$-$C_4$-alkylene;

n is 0, 1 or 2;

$R^1$ is hydrogen, $C_1$-$C_4$-alkyl, $C_1$-$C_4$-haloalkyl, $C_3$-$C_6$-cycloalkyl, $C_3$-$C_6$-cycloalkyl-$C_1$-$C_4$-alkyl, $C_1$-$C_4$-hydroxyalkyl, $C_1$-$C_4$-alkoxy-$C_1$-$C_4$-alkyl, $C_3$-$C_4$-alkenyl or $C_3$-$C_4$-alkynyl;

$R^2$ is $C_1$-$C_4$-alkyl, $C_1$-$C_4$-haloalkyl or, together with $R^1$, is $C_2$-$C_5$-alkylene or, in the case of n=2, the two radicals $R^2$ can together be $C_1$-$C_4$-alkylene;

$R^3$ is hydrogen or $C_1$-$C_4$-alkyl;

$R^{3a}$, $R^{3b}$ are, independently of each other, hydrogen or $C_1$-$C_4$-alkyl;

$R^4$ is $C_1$-$C_4$-alkyl, $C_1$-$C_4$-haloalkyl, $C_2$-$C_4$-alkenyl $C_3$-$C_6$-cycloalkyl, $C_3$-$C_6$-cycloalkyl-$C_1$-$C_4$-alkyl, phenyl or benzyl;

$R^5$ is hydrogen, $C_1$-$C_4$-alkyl, $C_1$-$C_4$-haloalkyl, $C_2$-$C_4$-alkenyl $C_3$-$C_6$-cycloalkyl, $C_3$-$C_6$-cycloalkyl-$C_1$-$C_4$-alkyl, phenyl or benzyl; and $R^6$, $R^7$ are each independently selected from $C_1$-$C_4$-alkyl, $C_1$-$C_4$-haloalkyl or together with the nitrogen to which they are bound form a saturated 3-, 4-, 5- or 6-membered heterocycle, which additionally may comprise an oxygen atom or an additional nitrogen atom as a ring member and which may carry 1, 2, 3 or 4 $C_1$-$C_4$ alkyl groups;

the N-oxides thereof and the physiologically tolerated acid addition salts of these compounds.

These compounds have not previously been described, with the exception of 4-methyl-N-[6-(4-methylpiperazin-1-yl)pyridin-3-yl)benzenesulfonamide and 4-chloro-N-[6-(4-methylpiperazin-1-yl)pyridin-3-yl)benzenesulfonamide, which are offered for sale by Ambinter, Paris, as test substances for exploratory libraries.

The present invention therefore relates to N-[(piperazinyl)hetaryl]arylsulfonamide compounds of the general formula 1, to their N-oxides and to their physiologically tolerated acid addition salts, with the exception of the compounds 4-methyl-N-[6-(4-methylpiperazin-1-yl)pyridin-3-yl)benzenesulfonamide and 4-chloro-N-[6-(4-methylpiperazin-1-yl)pyridin-3-yl)benzenesulfonamide.

The present invention also relates to the use of N-[(piperazinyl)hetaryl]arylsulfonamide compounds of the general formula 1, of their N-oxides and of their acid addition salts for producing a pharmaceutical composition for treating diseases which respond to the influence of dopamine-$D_3$ receptor antagonists or agonists.

The diseases which respond to the influence of dopamine $D_3$ receptor antagonists or agonists include, in particular, disturbances and diseases of the central nervous system, in particular affective disturbances, neurotic disturbances, stress disturbances and somatoform disturbances and psychoses, especially schizophrenia and depression and, in addition, disturbances of kidney function, in particular kidney function disturbances which are caused by diabetes mellitus (see WO 00/67847).

According to the invention, at least one compound of the general formula I having the meanings mentioned at the outset is used for treating the abovementioned indications. Provided the compounds of the formula I possess one or more centers of asymmetry, it is also possible to use enantiomeric mixtures, in particular racemates, diastereomeric mixtures and tautomeric mixtures, preferably, however, the respective essentially pure enantiomers, diastereomers and tautomers.

It is likewise possible to use physiologically tolerated salts of the compounds of the formula I, especially acid addition salts with physiologically tolerated acids. Examples of suitable physiologically tolerated organic and inorganic acids are hydrochloric acid, hydrobromic acid, phosphoric acid, sulfuric acid, $C_1$-$C_4$-alkylsulfonic acids, such as methanesulfonic acid, aromatic sulfonic acids, such as benzenesulfonic acid and toluenesulfonic acid, oxalic acid, maleic acid, fumaric acid, lactic acid, tartaric acid, adipic acid and benzoic acid. Other utilizable acids are described in Fortschritte der Arzneimittelforschung [Advances in drug research], Volume 10, pages 224 ff., Birkhäuser Verlag, Basel and Stuttgart, 1966.

It is likewise possible to use N-oxides of the compounds of the formula I. In the N-oxides of the compounds of the formula I, one or more of the N atoms which is/are ring members, and in particular ring members in the aromatic heterocycles Q and/or Ar, are present as an N-oxide group. Preference is given to those N-oxides of the formula I in which the ring nitrogen atoms in the piperazine ring do not form any N-oxide group. Particularly preferred N-oxides exhibit a N-oxide group on one or two of the ring nitrogen atoms of Ar and/or Q.

Here and in that which follows, halogen is fluorine, chlorine, bromine or iodine.

$C_n$-$C_m$-Alkyl (in radicals such as alkoxy, alkoxyalkyl, alkylthio, alkylamino, dialkylamino etc., as well) is a straight-chain or branched alkyl group having from n to m carbon atoms, e.g. from 1 to 4 carbon atoms. Examples of an alkyl group are methyl, ethyl, n-propyl, iso-propyl, n-butyl, 2-butyl, iso-butyl, tert-butyl, n-pentyl, 2-pentyl, neopentyl, n-hexyl and the like.

$C_1$-$C_4$-Haloalkyl (in radicals such as haloalkoxy, haloalkoxyalkyl, haloalkylthio, etc., as well) is an alkyl group having from 1 to 4 C atoms in which all or some, e.g. 1, 2, 3 or 4 of the hydrogen atoms, is/are replaced by halogen atoms, in particular by chlorine or fluorine. Preferred haloalkyl is $C_1$-$C_2$-fluoroalkyl or $C_1$-$C_2$-fluorochloroalkyl, in particular $CF_3$, $CHF_2$, $CF_2Cl$, $CH_2F$, and $CH_2CF_3$.

$C_1$-$C_4$-Hydroxyalkyl is a $C_1$-$C_4$-alkyl group which possesses an OH group, such as 2-hydroxyethyl, 2-hydroxypropyl, 3-hydroxypropyl, 2-hydroxybutyl, 3-hydroxybutyl, 2-methyl-2-hydroxypropyl etc.

$C_1$-$C_4$-Alkoxy-$C_1$-$C_4$-alkyl is a $C_1$-$C_4$-alkyl group which carries a $C_1$-$C_4$-alkoxy substituent, e.g. methoxymethyl, ethoxymethyl, 2-methoxyethyl, 1-methoxyethyl, 2-ethoxyethyl, 1-ethoxyethyl, n-propoxymethyl, isopropoxymethyl, n-butoxymethyl, (1-methylpropoxy)methyl, (2-methylpropoxy)methyl, $CH_2$—$OC(CH_3)_3$, 2-(methoxy)ethyl, 2-(ethoxy)ethyl, 2-(n-propoxy)ethyl, 2-(1-methylethoxy)ethyl, 2-(n-butoxy)ethyl, 2-(1-methylpropoxy)ethyl, 2-(2-methylpropoxy)ethyl, 2-(1,1-dimethylethoxy)ethyl, 2-(methoxy)propyl, 2-(ethoxy)propyl, 2-(n-propoxy)propyl, 2-(1-methylethoxy)propyl, 2-(n-butoxy)propyl, 2-(1-methylpropoxy)propyl, 2-(2-methylpropoxy)propyl, 2-(1,1-dimethylethoxy)propyl, 3-(methoxy)propyl, 3-(ethoxy)propyl, 3-(n-propoxy)propyl, 3-(1-methylethoxy)propyl, 3-(n-butoxy)propyl, 3-(1-methylpropoxy)propyl, 3-(2-methylpropoxy)propyl, 3-(1,1-dimethylethoxy)propyl, 2-(methoxy)butyl, 2-(ethoxy)butyl, 2-(n-propoxy)butyl, 2-(1-methylethoxy)butyl, 2-(n-butoxy)butyl, 2-(1-methylpropoxy)butyl, 2-(2-methylpropoxy)butyl, 2-(1,1-dimethylethoxy)butyl, 3-(methoxy)butyl, 3-(ethoxy)butyl, 3-(n-propoxy)butyl, 3-(1-methylethoxy)butyl, 3-(n-butoxy)butyl, 3-(1-methylpropoxy)butyl, 3-(2-methylpropoxy)butyl, 3-(1,1-dimethylethoxy)butyl, 4-(methoxy)butyl, 4-(ethoxy)butyl, 4-(n-propoxy)butyl, 4-(1-methylethoxy)butyl, 4-(n-butoxy)butyl, 4-(1-methylpropoxy)butyl, 4-(2-methylpropoxy)butyl or 4-(1,1-dimethylethoxy)butyl, preferably methoxymethyl, ethoxymethyl, 2-methoxyethyl, 2-ethoxyethyl, 2-(methoxy)propyl, 2-(ethoxy)propyl or 3-(methoxy)propyl, or 3-(ethoxy)propyl.

$C_3$-$C_6$-Cycloalkyl is a cycloaliphatic radical having from 3 to 6 C atoms, such as cyclopropyl, cyclobutyl, cyclopentyl and cyclohexyl.

$C_3$-$C_6$-Cycloalkyl-$C_1$-$C_4$-alkyl is a $C_1$-$C_4$-alkyl group which carries a $C_3$-$C_6$-cycloalkyl radical, e.g. cyclopropylmethyl, cyclobutylmethyl, cyclopentylmethyl, 1-cyclopropylethyl, 1-cyclobutylethyl, 1-cyclopentylethyl, 2-cyclopropylethyl, 2-cyclobutylethyl, 2-cyclopentylethyl, 1-cyclopropylpropyl, 1-cyclobutylpropyl, 1-cyclopentylpropyl, 2-cyclopropylpropyl, 2-cyclobutylpropyl, 2-cyclopentylpropyl, 3-cyclopropylpropyl, 3-cyclobutylpropyl, 3-cyclopentylpropyl, 1-cyclopropyl-1-methylethyl, 1-cyclopentyl-1-methylethyl, 1-cyclopentyl-1-methylethyl, 3-cyclohexylpropyl, 1-cyclohexyl-1-methylethyl, 1-cyclohexyl-1-methylethyl or 1-cyclohexyl-1-methylethyl.

$C_2$-$C_4$-Alkenyl (in radicals such as alkenyloxy as well) is a singly unsaturated hydrocarbon radical having 2, 3, 4, 5 or 6 C-atoms, e.g. vinyl, allyl(2-propen-1-yl), 1-propen-1-yl, 2-propen-2-yl, methallyl(2-methylprop-2-en-1-yl) and the like. $C_3$-$C_4$-Alkenyl is, in particular, allyl, 1-methylprop-2-en-1-yl, 2-buten-1-yl, 3-buten-1-yl, methallyl, 2-penten-1-yl, 3-penten-1-yl, 4-penten-1-yl, 1-methylbut-2-en-1-yl or 2-ethylprop-2-en-1-yl.

$C_3$-$C_6$-Alkynyl (in radicals such as alkinyloxy as well) is a hydrocarbon radical having 2, 3, 4, 5 or 6 C atoms which possesses a triple bond, e.g. propargyl (2-propyn-1-yl), 1-methylprop-2-yn-1-yl, 2-butyn-1-yl, 3-butyn-1-yl, 2-pentyn-1-yl, 1-pentyn-3-yl, etc.

Examples of 6-membered heteroaromatic radicals which possess 1 or 2 nitrogen atoms as ring members are, in particular, 2-, 3- or 4-pyridinyl, 2-, 4- or 5-pyrimidinyl, 2- or 3-pyrazinyl and 3- or 4-pyridazinyl. Examples of bivalent, 6-membered heteroaromatic radicals which possess 1 or 2 nitrogen atoms as ring members are, in particular, pyridin-2,4-diyl, pyridin-2,5-diyl, pyridin-2,6-diyl, pyridin-3,5-diyl, pyrimidin-2,4-diyl, pyrimidin-2,5-diyl, pyrimidin-4,6-diyl, pyrazin-2,5-diyl, pyrazin-2,6-diyl, pyridazin-3,6-diyl and pyridazin-3,5-diyl.

With regard to using the compounds according to the invention as dopamine $D_3$ receptor ligands, preference is given to those compounds of formula I in which the piperazin ring is bonded to the heteroaromatic radical Q in the meta position or, in particular, in the para position with respect to the group R.

In one embodiment the radical $R^a$ is selected from halogen, CN, $NO_2$, $CO_2R^4$, $COR^5$, $C_1$-$C_4$-alkyl and $C_1$-$C_4$-haloalkyl. Preferred meanings of $R^4$ and $R^5$ are, independently of each other, H or $C_1$-$C_4$-alkyl. In another embodiement $R^a$ is selected from $C_1$-$C_4$-alkoxy, $C_1$-$C_4$-haloalkoxy, $NH_2$, $NHR^6$ and $NR^6R^7$. In this embodiment preferred meanings of $R^6$ and $R^7$ are independently of each other methyl or ethyl.

The heteroaromatic radical Q may be unsubstituted or possess a substituent $R^a$ which is selected from halogen, $C_1$-$C_4$-alkyl and $C_1$-$C_4$-haloalkyl, $C_1$-$C_4$-alkoxy, $NH_2$, $NHR^6$, $NR^6R^7$ and $C_1$-$C_4$-haloalkoxy. In one embodiment the radical $R^a$ is selected from halogen, $C_1$-$C_4$-alkyl and $C_1$-$C_4$-haloalkyl. In another preferred embodiment $R^a$ is selected from $C_1$-$C_4$-alkoxy, $C_1$-$C_4$-haloalkoxy, $NH_2$, $NHR^6$ and $NR^6R^7$ with specific preference given to methoxy, $NH_2$, methylamino, dimethylamino, ethylamine, diethylamino and methylethylamino.

In a very preferred embodiment, Q is unsubstituted.

In another very preferred embodiment, Q carries a radical selected from $C_1$-$C_4$-haloalkoxy, $C_1$-$C_4$-alkoxy, $C_1$-$C_4$-haloalkyl, $C_1$-$C_4$-alkyl, $NH_2$, $NHR^6$ or $NR^6R^7$. and especially methoxy or methyl.

Preference is given to the variables Q, $R^1$, $R^2$, $R^3$ and Ar preferably having, independently of each other, the meanings given below:

Q is preferably a radical of the formula A:

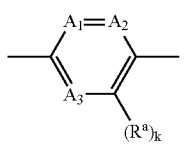

(A)

in which $A_1$, $A_2$ and $A_3$ are, independently of each other, N or CH, and one or two of the variables $A_1$, $A_2$ and $A_3$ can also be C—$R^a$, with $A_1$, $A_2$ and $A_3$ not simultaneously being N or being simultaneously selected from CH and C—$R^a$. In formula A, k is 0 or 1 and $R^a$ has the previously mentioned meanings.

In formula A, $R^a$ is preferably selected from halogen, especially chlorine or fluorine, $C_1$-$C_4$-alkyl, especially methyl, and $C_1$-$C_4$-haloalkyl, especially trifluoromethyl, $C_1$-$C_4$-alkoxy especially methoxy, $C_1$-$C_4$-haloalkoxy, especially difluormethoxy or trifluormethoxy, $NH_2$, $NHR^6$ especially methylamino or ethylamino, and $NR^6R^7$, especially dimethylamino, diethylamino or methylethylamino. The C atom which is located between the atoms $A_1$ and $A_3$ preferably carries the piperazinyl radical.

In particular, none of the variables $A_1$, $A_2$ and $A_3$ is C—$R_a$. Preferred radicals Q are those of formula A, in which $A_1$ and/or $A_3$ is/are N, the remaining variable $A_1$ or $A_2$ is CH or C—$R^a$, $A_2$ is CH, and the piperazinyl radical is bonded to the C atom which is located between $A_1$ and $A_3$.

Preference is furthermore given to compounds of the formula 1, in which $A_1$ and $A_2$ in formula A are N and $A_3$ is CH or C—$R^a$.

In a very preferred embodiment k in formula A is 0. In particular, Q is pyridin-2,5-diyl or pyrimidin-2,5-diyl which are unsubstituted or able to possess a substituent $R^a$ which is different from hydrogen. The piperazinyl radical is then preferably arranged in the 2 position.

In another very preferred embodiment k in formula A is 1, $A_3$ is N, $A_1$ and $A_2$ are, independently of each other, N or CH and $R^a$ is selected from $C_1$-$C_4$-alkoxy, $C_1$-$C_4$-alkyl, $NH_2$, $NHR^6$, $NR^6R^7$ and $C_1$-$C_4$-haloalkoxy. In particular $R^a$ is methoxy or methyl. Most preferably the piperazine radical is located in the 2 position. In this embodiment compounds are especially preferred, in which $A_1$ is N or CH, in particular CH and $A_2$ is CH.

Ar is preferably phenyl or pyridyl which, where appropriate, possesses one or two of the abovementioned substituents $R^b$. With regard to using the compounds according to the invention as dopamine $D_3$ receptor ligands, preference is given to those compounds of formula I in which Ar carries one substituent $R^b$ in the para position and, where appropriate, a further substituent $R^b$ in the ortho position or in the metaposition, in each case related to the binding site for the sulfonamide group. The radicals $R^b$ may be identical or different. Preference is given to the radicals $R^b$ in the para position being selected from $C_2$-$C_6$-alkyl, $C_2$-$C_6$-alkenyl, $C_2$-$C_6$-alkynyl, $C_3$-$C_6$-Cycloalkyl, $NH_2$, $NHR^6$ and $NR^6R^7$.

In one preferred embodiment the radical $R^b$ in the para position is selected from $C_2$-$C_6$-alkyl, $C_2$-$C_6$-alkenyl, $C_2$-$C_6$-alkynyl, $C_3$-$C_6$-cycloalkyl, in particular, from branched $C_3$-$C_6$-alkyl, especially isopropyl, and $C_3$-$C_6$-cycloalkyl, especially cyclopropyl. Very particular preference is given to the radical $R^b$ which is arranged in the para position of Ar being isopropyl.

In one preferred embodiment the radical $R^b$ in the para position is selected from $NHR^6$ and $NR^6R^7$. In this embodiment preferred meanings of $R^6$ and $R^7$ are independently of each other methyl or ethyl or form together with the N atom a saturated 3-, 4-, 5- or 6-membered heterocycle, which additionally may comprise an oxygen atom or an additional nitrogen atom as a ring member and which may carry 1, 2, 3 or 4 $C_1$-$C_4$ alkyl groups, e.g. a radical from the group consisting of aziridinyl, azetidinyl, pyrrolidinyl, piperidinyl, morpholinyl etc.

Preferred radicals $R^b$ in the meta position or ortho position are selected from halogen, especially chlorine and fluorine, $C_1$-$C_4$-alkyl, especially methyl, CN, trifluoromethyl and difluoromethyl.

With regard to using the compounds according to the invention as dopamine $D_3$ receptor ligands, preference is given to those compounds of the formula I in which $R^1$ is different from hydrogen, in particular hydrogen and methyl. In particular, $R^1$ is $C_2$-$C_3$-alkyl, cyclopropylmethyl or, particularly preferably, ethyl, allyl or n-propyl.

The variable n is preferably 0 or 1. Provided n is ≠0, $R^2$ is preferably methyl. When n is ≠0, the group $R^2$ is preferably bonded to a carbon atom in the piperazine ring which is adjacent to the group $R^1$—N. In particularly preferred compounds, n=0. Particular preference is also given to compounds of the formula I in which it applies that n=1 and $R^2$ is a methyl group which is bonded to a carbon atom in the piperazine ring which is adjacent to the group $R^1$—N. The compounds can then be present as a racemate, as pure enantiomers or as nonracemic mixtures of the enantiomers.

Among these, particular preference is given to those compounds in which the C atom which carries the methyl group exhibits the S configuration.

$R^3$ is preferably hydrogen or $C_1$-$C_4$-alkyl and, in particular, hydrogen.

If R is a group $CR^{3a}R^{3b}$, at least one of the radicals $R^{3a}$ or $R^{3b}$ is hydrogen. More preferably both radicals $R^{3a}$ and $R^{3b}$ are hydrogen.

Among the compounds of the general formula 1, preference is given to the compounds I, wherein R is N—$R^3$, wherein $R^3$ is as defined above and especially H. Amongst these compounds preference is given to the compounds of the general formula Ia

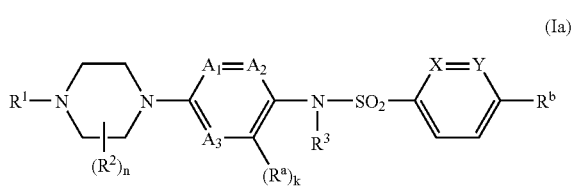

(Ia)

in which n, $R^1$, $R^2$, $R^3$, $R^a$ and $R^b$ have the previously mentioned meanings, in particular the meanings specified as being preferred, and in which $A_1$, $A_2$ and $A_3$ are, independently of each other, N or CH, and one of the variables $A_1$, $A_2$ and $A_3$ can also be C—$R^a$, with $A_1$, $A_2$ and $A_3$ not simultaneously being N or simultaneously being selected from CH and C—$R^a$, and X and Y are selected from CH, C—$R^{b'}$ and N, in which $R^{b'}$ is halogen, methyl, CN, difluoromethyl or trifluoromethyl, with X and Y not simultaneously being N or simultaneously being C—$R^{b'}$, and k is 0 or 1. $R^a$ has the previously mentioned meanings. In particular, $R^a$ is selected from halogen, especially chlorine or fluorine, $C_1$-$C_4$-alkyl, especially methyl, and $C_1$-$C_4$-haloalkyl, especially trifluoromethyl, $C_1$-$C_4$-alkoxy especially methoxy, $C_1$-$C_4$-haloalkoxy, especially difluormethoxy or trifluormethoxy, $NH_2$, $NHR^6$ especially methylamino or ethylamino, and $NR^6R^7$, especially dimethylamino, diethylamino or methylethylamino.

In particular, none of the variables $A_1$, $A^2$ and $A^3$ is C—$R^a$. Preferred compounds Ia are those in which $A_1$ and/or $A_3$ is/are N, the remaining variable $A_1$ or $A_2$ is CH or C—$R^a$, $A_2$ is CH.

In particular preferred embodiment, k=0. Among these, preference is furthermore given to compound I in which $A_1$ and $A_2$ are N and $A_3$ is CH or C—$R^a$. Among these, preference is given to those compounds of the formula Ia in which X or Y is CH or N and, in particular, both are CH.

In another very preferred embodiment k in formula Ia is 1, $A_3$ is N, $A_1$ and $A_2$ are, independently of each other, N or CH and $R^a$ is selected from $C_1$-$C_4$-alkyl, $C_1$-$C_4$-alkoxy, $C_1$-$C_4$-haloalkyl, $NH_2$, $NHR^6$, $NR^6R^7$ and $C_1$-$C_4$-haloalkoxy. In particular $R^a$ is methoxy or methyl. In this embodiment compounds are especially preferred, in which $A_1$ is N or CH, in particular CH and $A_2$ is CH.

Among the compounds of general formula Ia, preference is given to the compounds of general formula Ia.1

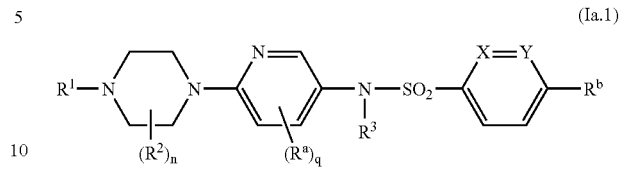

(Ia.1)

in which n, X, Y, $R^1$, $R^2$, $R^3$, $R^a$ and $R^b$ have the previously mentioned meanings, in particular the meanings specified as being preferred, and q is 0, 1 or 2 and in particular 0 or 1. If q is 1, the radical $R^a$ is preferably bound to the carbon atom which is adjacent to the nitrogen atom of the pyridine ring Among the compounds of general formula Ia, preference is furthermore given to the compounds of general formula Ia.2

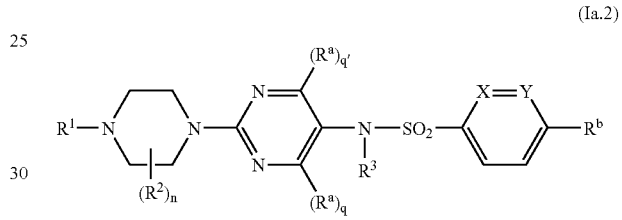

(Ia.2)

in which n, X, Y, $R^1$, $R^2$, $R^3$, $R^a$ and $R^b$ have the previously mentioned meanings, in particular the meanings specified as being preferred, and q and q' are independently of each other 0 or 1, with q+q' preferably being 0 or 1.

Examples of compounds of the formula Ia.1 are the compounds of the following general formulae Ia.1a, Ia.1b, Ia.1c, Ia.1d, Ia.1e, Ia.1f, Ia.1g, Ia.1h and Ia.1k:

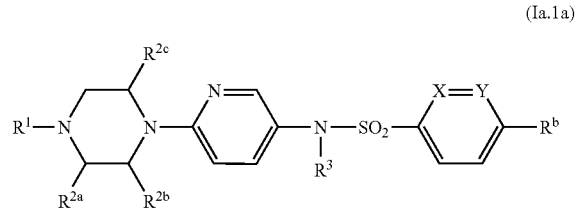

(Ia.1a)

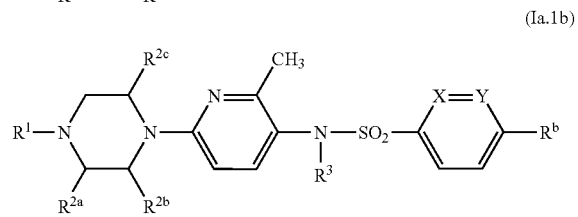

(Ia.1b)

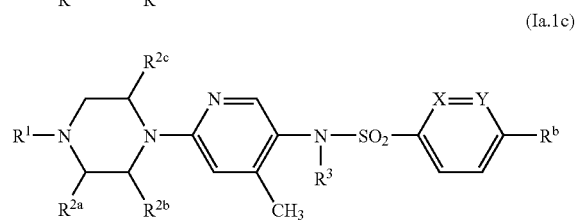

(Ia.1c)

-continued

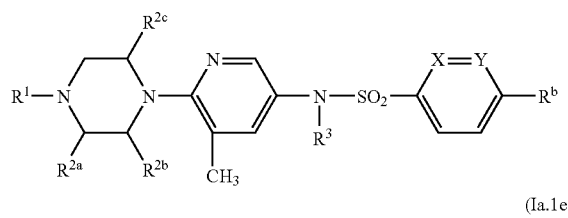
(Ia.1d)

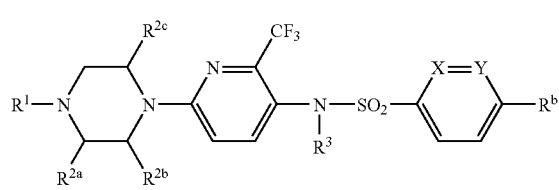
(Ia.1e)

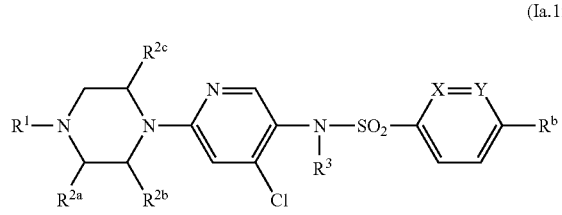
(Ia.1f)

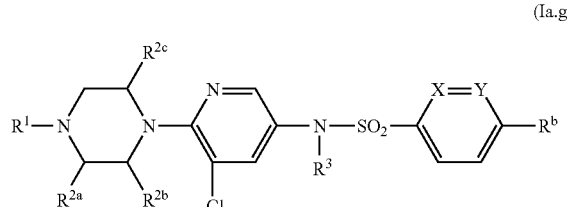
(Ia.g)

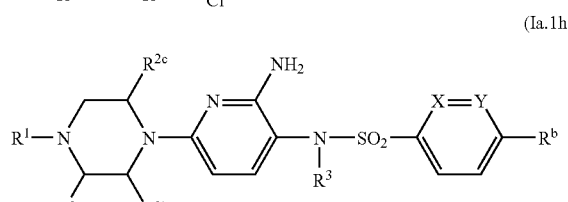
(Ia.1h)

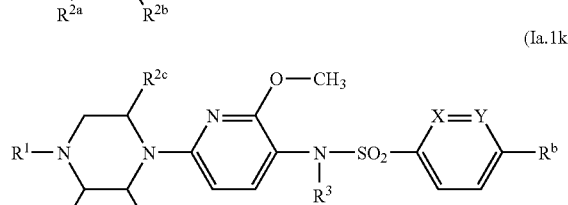
(Ia.1k)

in which $R^1$, $R^{2a}$, $R^{2b}$, $R^{2c}$, $R^3$, X, Y and $R^b$, have the meanings specified in one line in Table 1.

Examples of compounds of the formula Ia.2 are the compounds of the following general formulae Ia.2a, Ia.2b, Ia.2c, Ia.2d and Ia.2e:

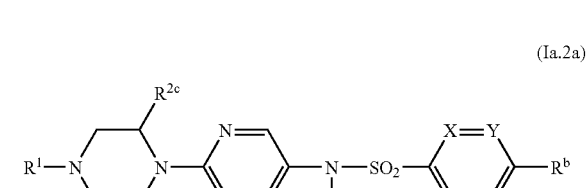
(Ia.2a)

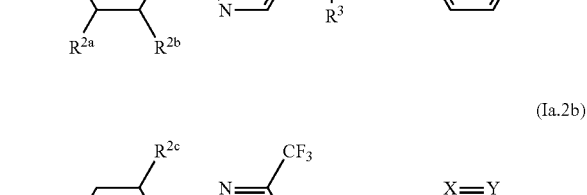
(Ia.2b)

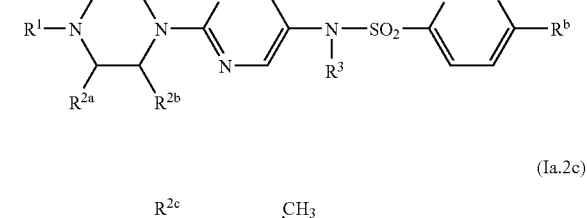
(Ia.2c)

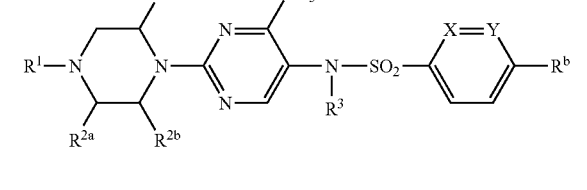
(Ia.2d)

(Ia.2e)

in which $R^1$, $R^{2a}$, $R^{2b}$, $R^{2c}$, $R^3$, X, Y and $R^b$ have the meanings specified in one line in Table 1.

TABLE 1

| No. | $R^1$ | $R^{2a}$ | $R^{2b}$ | $R^{2c}$ | $R^3$ | X | Y | $R^b$ |
|---|---|---|---|---|---|---|---|---|
| 1. | H | H | H | H | H | CH | CH | $CH(CH_3)_2$ |
| 2. | $CH_3$ | H | H | H | H | CH | CH | $CH(CH_3)_2$ |
| 3. | $CH_2CH_3$ | H | H | H | H | CH | CH | $CH(CH_3)_2$ |
| 4. | $CH_2CH=CH_2$ | H | H | H | H | CH | CH | $CH(CH_3)_2$ |
| 5. | $CH_2$-c-$C_3H_5$ | H | H | H | H | CH | CH | $CH(CH_3)_2$ |
| 6. | $CH_2CH_2CH_3$ | H | H | H | H | CH | CH | $CH(CH_3)_2$ |
| 7. | H | (s)$CH_3$ | H | H | H | CH | CH | $CH(CH_3)_2$ |
| 8. | $CH_3$ | (s)$CH_3$ | H | H | H | CH | CH | $CH(CH_3)_2$ |

TABLE 1-continued

| No. | R¹ | R²ᵃ | R²ᵇ | R²ᶜ | R³ | X | Y | Rᵇ |
|---|---|---|---|---|---|---|---|---|
| 9. | CH₂CH₃ | (s)CH₃ | H | H | H | CH | CH | CH(CH₃)₂ |
| 10. | CH₂CH=CH₂ | (s)CH₃ | H | H | H | CH | CH | CH(CH₃)₂ |
| 11. | CH₂-c-C₃H₅ | (s)CH₃ | H | H | H | CH | CH | CH(CH₃)₂ |
| 12. | CH₂CH₂CH₃ | (s)CH₃ | H | H | H | CH | CH | CH(CH₃)₂ |
| 13. | CH₃ | rac-CH₃ | H | H | H | CH | CH | CH(CH₃)₂ |
| 14. | CH₂CH=CH₂ | rac-CH₃ | H | H | H | CH | CH | CH(CH₃)₂ |
| 15. | CH₂-c-C₃H₅ | rac-CH₃ | H | H | H | CH | CH | CH(CH₃)₂ |
| 16. | CH₂CH₂CH₃ | rac-CH₃ | H | H | H | CH | CH | CH(CH₃)₂ |
| 17. | CH₃ | (R)CH₃ | H | H | H | CH | CH | CH(CH₃)₂ |
| 18. | CH₂CH=CH₂ | (R)CH₃ | H | H | H | CH | CH | CH(CH₃)₂ |
| 19. | CH₂-c-C₃H₅ | (R)CH₃ | H | H | H | CH | CH | CH(CH₃)₂ |
| 20. | CH₂CH₂CH₃ | (R)CH₃ | H | H | H | CH | CH | CH(CH₃)₂ |
| 21. | CH₃ | H | CH₃ | H | H | CH | CH | CH(CH₃)₂ |
| 22. | CH₂CH=CH₂ | H | CH₃ | H | H | CH | CH | CH(CH₃)₂ |
| 23. | CH₂-c-C₃H₅ | H | CH₃ | H | H | CH | CH | CH(CH₃)₂ |
| 24. | CH₂CH₂CH₃ | H | CH₃ | H | H | CH | CH | CH(CH₃)₂ |
| 25. | CH₃ | CH₃ | H | CH₃ | H | CH | CH | CH(CH₃)₂ |
| 26. | CH₂CH=CH₂ | CH₃ | H | CH₃ | H | CH | CH | CH(CH₃)₂ |
| 27. | CH₂-c-C₃H₅ | CH₃ | H | CH₃ | H | CH | CH | CH(CH₃)₂ |
| 28. | CH₂CH₂CH₃ | CH₃ | H | CH₃ | H | CH | CH | CH(CH₃)₂ |
| 29. | CH₃ | CH₃ | CH₃ | H | H | CH | CH | CH(CH₃)₂ |
| 30. | CH₂CH=CH₂ | CH₃ | CH₃ | H | H | CH | CH | CH(CH₃)₂ |
| 31. | CH₂-c-C₃H₅ | CH₃ | CH₃ | H | H | CH | CH | CH(CH₃)₂ |
| 32. | CH₂CH₂CH₃ | CH₃ | CH₃ | H | H | CH | CH | CH(CH₃)₂ |
| 33. | (s)(CH₂)₃ | | H | H | H | CH | CH | CH(CH₃)₂ |
| 34. | (s)(CH₂)₄ | | H | H | H | CH | CH | CH(CH₃)₂ |
| 35. | rac(CH₂)₃ | | H | H | H | CH | CH | CH(CH₃)₂ |
| 36. | rac (CH₂)₄ | | H | H | H | CH | CH | CH(CH₃)₂ |
| 37. | (R)(CH₂)₃ | | H | H | H | CH | CH | CH(CH₃)₂ |
| 38. | (R)(CH₂)₄ | | H | H | H | CH | CH | CH(CH₃)₂ |
| 39. | CH₂CH=CH₂ | H | H | H | H | C—Cl | CH | CH(CH₃)₂ |
| 40. | CH₂-c-C₃H₅ | H | H | H | H | C—Cl | CH | CH(CH₃)₂ |
| 41. | CH₂CH₂CH₃ | H | H | H | H | C—Cl | CH | CH(CH₃)₂ |
| 42. | CH₂CH=CH₂ | (s)CH₃ | H | H | H | C—Cl | CH | CH(CH₃)₂ |
| 43. | CH₂-c-C₃H₅ | (s)CH₃ | H | H | H | C—Cl | CH | CH(CH₃)₂ |
| 44. | CH₂CH₃ | (s)CH₃ | H | H | H | C—Cl | CH | CH(CH₃)₂ |
| 45. | CH₂CH₂CH₃ | (s)CH₃ | H | H | H | C—Cl | CH | CH(CH₃)₂ |
| 46. | CH₂CH=CH₂ | rac-CH₃ | H | H | H | C—Cl | CH | CH(CH₃)₂ |
| 47. | CH₂-c-C₃H₅ | rac-CH₃ | H | H | H | C—Cl | CH | CH(CH₃)₂ |
| 48. | CH₂CH₂CH₃ | rac-CH₃ | H | H | H | C—Cl | CH | CH(CH₃)₂ |
| 49. | CH₂CH₃ | rac-CH₃ | H | H | H | C—Cl | CH | CH(CH₃)₂ |
| 50. | CH₂CH=CH₂ | (R)CH₃ | H | H | H | C—Cl | CH | CH(CH₃)₂ |
| 51. | CH₂-c-C₃H₅ | (R)CH₃ | H | H | H | C—Cl | CH | CH(CH₃)₂ |
| 52. | CH₂CH₃ | (R)CH₃ | H | H | H | C—Cl | CH | CH(CH₃)₂ |
| 53. | CH₂CH₂CH₃ | (R)CH₃ | H | H | H | C—Cl | CH | CH(CH₃)₂ |
| 54. | CH₂CH=CH₂ | H | CH₃ | H | H | C—Cl | CH | CH(CH₃)₂ |
| 55. | CH₂-c-C₃H₅ | H | CH₃ | H | H | C—Cl | CH | CH(CH₃)₂ |
| 56. | CH₂CH₂CH₃ | H | CH₃ | H | H | C—Cl | CH | CH(CH₃)₂ |
| 57. | CH₂CH=CH₂ | CH₃ | H | CH₃ | H | C—Cl | CH | CH(CH₃)₂ |
| 58. | CH₂-c-C₃H₅ | CH₃ | H | CH₃ | H | C—Cl | CH | CH(CH₃)₂ |
| 59. | CH₂CH₂CH₃ | CH₃ | H | CH₃ | H | C—Cl | CH | CH(CH₃)₂ |
| 60. | CH₂CH=CH₂ | CH₃ | CH₃ | H | H | C—Cl | CH | CH(CH₃)₂ |
| 61. | CH₂-c-C₃H₅ | CH₃ | CH₃ | H | H | C—Cl | CH | CH(CH₃)₂ |
| 62. | CH₂CH₂CH₃ | CH₃ | CH₃ | H | H | C—Cl | CH | CH(CH₃)₂ |
| 63. | (CH₂)₃ | | H | H | H | C—Cl | CH | CH(CH₃)₂ |
| 64. | (CH₂)₄ | | H | H | H | C—Cl | CH | CH(CH₃)₂ |
| 65. | CH₂CH=CH₂ | H | H | H | H | CH | C—Cl | CH(CH₃)₂ |
| 66. | CH₂-c-C₃H₅ | H | H | H | H | CH | C—Cl | CH(CH₃)₂ |
| 67. | CH₂CH₂CH₃ | H | H | H | H | CH | C—Cl | CH(CH₃)₂ |
| 68. | CH₂CH=CH₂ | (s)CH₃ | H | H | H | CH | C—Cl | CH(CH₃)₂ |
| 69. | CH₂-c-C₃H₅ | (s)CH₃ | H | H | H | CH | C—Cl | CH(CH₃)₂ |
| 70. | CH₂CH₂CH₃ | (s)CH₃ | H | H | H | CH | C—Cl | CH(CH₃)₂ |
| 71. | CH₂CH₃ | (s)CH₃ | H | H | H | CH | C—Cl | CH(CH₃)₂ |
| 72. | CH₂CH=CH₂ | rac-CH₃ | H | H | H | CH | C—Cl | CH(CH₃)₂ |
| 73. | CH₂-c-C₃H₅ | rac-CH₃ | H | H | H | CH | C—Cl | CH(CH₃)₂ |
| 74. | CH₂CH₂CH₃ | rac-CH₃ | H | H | H | CH | C—Cl | CH(CH₃)₂ |
| 75. | CH₂CH₃ | rac-CH₃ | H | H | H | CH | C—Cl | CH(CH₃)₂ |
| 76. | CH₂CH=CH₂ | (R)CH₃ | H | H | H | CH | C—Cl | CH(CH₃)₂ |
| 77. | CH₂-c-C₃H₅ | (R)CH₃ | H | H | H | CH | C—Cl | CH(CH₃)₂ |
| 78. | CH₂CH₃ | (R)CH₃ | H | H | H | CH | C—Cl | CH(CH₃)₂ |
| 79. | CH₂CH₂CH₃ | (R)CH₃ | H | H | H | CH | C—Cl | CH(CH₃)₂ |
| 80. | CH₂CH=CH₂ | H | CH₃ | H | H | CH | C—Cl | CH(CH₃)₂ |
| 81. | CH₂-c-C₃H₅ | H | CH₃ | H | H | CH | C—Cl | CH(CH₃)₂ |
| 82. | CH₂CH₂CH₃ | H | CH₃ | H | H | CH | C—Cl | CH(CH₃)₂ |
| 83. | CH₂CH=CH₂ | CH₃ | H | CH₃ | H | CH | C—Cl | CH(CH₃)₂ |
| 84. | CH₂-c-C₃H₅ | CH₃ | H | CH₃ | H | CH | C—Cl | CH(CH₃)₂ |
| 85. | CH₂CH₂CH₃ | CH₃ | H | CH₃ | H | CH | C—Cl | CH(CH₃)₂ |

TABLE 1-continued

| No. | R¹ | R²ᵃ | R²ᵇ | R²ᶜ | R³ | X | Y | Rᵇ |
|---|---|---|---|---|---|---|---|---|
| 86. | CH₂CH=CH₂ | CH₃ | CH₃ | H | H | CH | C—Cl | CH(CH₃)₂ |
| 87. | CH₂-c-C₃H₅ | CH₃ | CH₃ | H | H | CH | C—Cl | CH(CH₃)₂ |
| 88. | CH₂CH₂CH₃ | CH₃ | CH₃ | H | H | CH | C—Cl | CH(CH₃)₂ |
| 89. | (CH₂)₃ | | H | H | H | CH | C—Cl | CH(CH₃)₂ |
| 90. | (CH₂)₄ | | H | H | H | CH | C—Cl | CH(CH₃)₂ |
| 91. | CH₂CH=CH₂ | H | H | H | H | C—CH₃ | CH | CH(CH₃)₂ |
| 92. | CH₂-c-C₃H₅ | H | H | H | H | C—CH₃ | CH | CH(CH₃)₂ |
| 93. | CH₂CH₂CH₃ | H | H | H | H | C—CH₃ | CH | CH(CH₃)₂ |
| 94. | CH₂CH=CH₂ | (s)CH₃ | H | H | H | C—CH₃ | CH | CH(CH₃)₂ |
| 95. | CH₂-c-C₃H₅ | (s)CH₃ | H | H | H | C—CH₃ | CH | CH(CH₃)₂ |
| 96. | CH₂CH₂CH₃ | (s)CH₃ | H | H | H | C—CH₃ | CH | CH(CH₃)₂ |
| 97. | CH₂CH=CH₂ | rac-CH₃ | H | H | H | C—CH₃ | CH | CH(CH₃)₂ |
| 98. | CH₂-c-C₃H₅ | rac-CH₃ | H | H | H | C—CH₃ | CH | CH(CH₃)₂ |
| 99. | CH₂CH₂CH₃ | rac-CH₃ | H | H | H | C—CH₃ | CH | CH(CH₃)₂ |
| 100 | CH₂CH=CH₂ | (R)CH₃ | H | H | H | C—CH₃ | CH | CH(CH₃)₂ |
| 101 | CH₂-c-C₃H₅ | (R)CH₃ | H | H | H | C—CH₃ | CH | CH(CH₃)₂ |
| 102 | CH₂CH₂CH₃ | (R)CH₃ | H | H | H | C—CH₃ | CH | CH(CH₃)₂ |
| 103 | CH₂CH=CH₂ | H | CH₃ | H | H | C—CH₃ | CH | CH(CH₃)₂ |
| 104 | CH₂-c-C₃H₅ | H | CH₃ | H | H | C—CH₃ | CH | CH(CH₃)₂ |
| 105 | CH₂CH₂CH₃ | H | CH₃ | H | H | C—CH₃ | CH | CH(CH₃)₂ |
| 106 | CH₂CH=CH₂ | CH₃ | H | CH₃ | H | C—CH₃ | CH | CH(CH₃)₂ |
| 107 | CH₂-c-C₃H₅ | CH₃ | H | CH₃ | H | C—CH₃ | CH | CH(CH₃)₂ |
| 108 | CH₂CH₂CH₃ | CH₃ | H | CH₃ | H | C—CH₃ | CH | CH(CH₃)₂ |
| 109 | CH₂CH=CH₂ | CH₃ | CH₃ | H | H | C—CH₃ | CH | CH(CH₃)₂ |
| 110 | CH₂-c-C₃H₅ | CH₃ | CH₃ | H | H | C—CH₃ | CH | CH(CH₃)₂ |
| 111 | CH₂CH₂CH₃ | CH₃ | CH₃ | H | H | C—CH₃ | CH | CH(CH₃)₂ |
| 112 | (CH₂)₃ | | H | H | H | C—CH₃ | CH | CH(CH₃)₂ |
| 113 | (CH₂)₄ | | H | H | H | C—CH₃ | CH | CH(CH₃)₂ |
| 114 | CH₂CH=CH₂ | H | H | H | H | CH | C—CH₃ | CH(CH₃)₂ |
| 115 | CH₂-c-C₃H₅ | H | H | H | H | CH | C—CH₃ | CH(CH₃)₂ |
| 116 | CH₂CH₂CH₃ | H | H | H | H | CH | C—CH₃ | CH(CH₃)₂ |
| 117 | CH₂CH=CH₂ | (s)CH₃ | H | H | H | CH | C—CH₃ | CH(CH₃)₂ |
| 118 | CH₂-c-C₃H₅ | (s)CH₃ | H | H | H | CH | C—CH₃ | CH(CH₃)₂ |
| 119 | CH₂CH₂CH₃ | (s)CH₃ | H | H | H | CH | C—CH₃ | CH(CH₃)₂ |
| 120 | CH₂CH=CH₂ | rac-CH₃ | H | H | H | CH | C—CH₃ | CH(CH₃)₂ |
| 121 | CH₂-c-C₃H₅ | rac-CH₃ | H | H | H | CH | C—CH₃ | CH(CH₃)₂ |
| 122 | CH₂CH₂CH₃ | rac-CH₃ | H | H | H | CH | C—CH₃ | CH(CH₃)₂ |
| 123 | CH₂CH=CH₂ | (R)CH₃ | H | H | H | CH | C—CH₃ | CH(CH₃)₂ |
| 124 | CH₂-c-C₃H₅ | (R)CH₃ | H | H | H | CH | C—CH₃ | CH(CH₃)₂ |
| 125 | CH₂CH₂CH₃ | (T)CH₃ | H | H | H | CH | C—CH₃ | CH(CH₃)₂ |
| 126 | CH₂CH=CH₂ | H | CH₃ | H | H | CH | C—CH₃ | CH(CH₃)₂ |
| 127 | CH₂-c-C₃H₅ | H | CH₃ | H | H | CH | C—CH₃ | CH(CH₃)₂ |
| 128 | CH₂CH₂CH₃ | H | CH₃ | H | H | CH | C—CH₃ | CH(CH₃)₂ |
| 129 | CH₂CH=CH₂ | CH₃ | H | CH₃ | H | CH | C—CH₃ | CH(CH₃)₂ |
| 130 | CH₂-c-C₃H₅ | CH₃ | H | CH₃ | H | CH | C—CH₃ | CH(CH₃)₂ |
| 131 | CH₂CH₂CH₃ | CH₃ | H | CH₃ | H | CH | C—CH₃ | CH(CH₃)₂ |
| 132 | CH₂CH=CH₂ | CH₃ | CH₃ | H | H | CH | C—CH₃ | CH(CH₃)₂ |
| 133 | CH₂-c-C₃H₅ | CH₃ | CH₃ | H | H | CH | C—CH₃ | CH(CH₃)₂ |
| 134 | CH₂CH₂CH₃ | CH₃ | CH₃ | H | H | CH | C—CH₃ | CH(CH₃)₂ |
| 135 | (CH₂)₃ | | H | H | H | CH | C—CH₃ | CH(CH₃)₂ |
| 136 | (CH₂)₄ | | H | H | H | CH | C—CH₃ | CH(CH₃)₂ |
| 137 | H | H | H | H | H | CH | CH | c-C₃H₅ |
| 138 | CH₃ | H | H | H | H | CH | CH | c-C₃H₅ |
| 139 | CH₂CH₃ | H | H | H | H | CH | CH | c-C₃H₅ |
| 140 | CH₂CH=CH₂ | H | H | H | H | CH | CH | c-C₃H₅ |
| 141 | CH₂-c-C₃H₅ | H | H | H | H | CH | CH | c-C₃H₅ |
| 142 | CH₂CH₂CH₃ | H | H | H | H | CH | CH | c-C₃H₅ |
| 143 | H | (s)CH₃ | H | H | H | CH | CH | c-C₃H₅ |
| 144 | CH₃ | (s)CH₃ | H | H | H | CH | CH | c-C₃H₅ |
| 145 | CH₂CH₃ | (s)CH₃ | H | H | H | CH | CH | c-C₃H₅ |
| 146 | CH₂CH=CH₂ | (s)CH₃ | H | H | H | CH | CH | c-C₃H₅ |
| 147 | CH₂-c-C₃H₅ | (s)CH₃ | H | H | H | CH | CH | c-C₃H₅ |
| 148 | CH₂CH₂CH₃ | (s)CH₃ | H | H | H | CH | CH | c-C₃H₅ |
| 149 | CH₃ | rac-CH₃ | H | H | H | CH | CH | c-C₃H₅ |
| 150 | CH₂CH=CH₂ | rac-CH₃ | H | H | H | CH | CH | c-C₃H₅ |
| 151 | CH₂-c-C₃H₅ | rac-CH₃ | H | H | H | CH | CH | c-C₃H₅ |
| 152 | CH₂CH₂CH₃ | rac-CH₃ | H | H | H | CH | CH | c-C₃H₅ |
| 153 | CH₂CH₃ | (R)CH₃ | H | H | H | CH | CH | c-C₃H₅ |
| 154 | CH₂CH=CH₂ | (R)CH₃ | H | H | H | CH | CH | c-C₃H₅ |
| 155 | CH₂-c-C₃H₅ | (R)CH₃ | H | H | H | CH | CH | c-C₃H₅ |
| 156 | CH₂CH₂CH₃ | (R)CH₃ | H | H | H | CH | CH | c-C₃H₅ |
| 157 | CH₃ | H | CH₃ | H | H | CH | CH | c-C₃H₅ |
| 158 | CH₂CH=CH₂ | H | CH₃ | H | H | CH | CH | c-C₃H₅ |
| 159 | CH₂-c-C₃H₅ | H | CH₃ | H | H | CH | CH | c-C₃H₅ |
| 160 | CH₂CH₂CH₃ | H | CH₃ | H | H | CH | CH | c-C₃H₅ |
| 161 | CH₃ | CH₃ | H | CH₃ | H | CH | CH | c-C₃H₅ |
| 162 | CH₂CH=CH₂ | CH₃ | H | CH₃ | H | CH | CH | c-C₃H₅ |

TABLE 1-continued

| No. | R¹ | R²ᵃ | R²ᵇ | R²ᶜ | R³ | X | Y | Rᵇ |
|---|---|---|---|---|---|---|---|---|
| 163 | CH₂-c-C₃H₅ | CH₃ | H | CH₃ | H | CH | CH | c-C₃H₅ |
| 164 | CH₂CH₂CH₃ | CH₃ | H | CH₃ | H | CH | CH | c-C₃H₅ |
| 165 | CH₃ | CH₃ | CH₃ | H | H | CH | CH | c-C₃H₅ |
| 166 | CH₂CH=CH₂ | CH₃ | CH₃ | H | H | CH | CH | c-C₃H₅ |
| 167 | CH₂-c-C₃H₅ | CH₃ | CH₃ | H | H | CH | CH | c-C₃H₅ |
| 168 | CH₂CH₂CH₃ | CH₃ | CH₃ | H | H | CH | CH | c-C₃H₅ |
| 169 | (s)(CH₂)₃ | | H | H | H | CH | CH | c-C₃H₅ |
| 170 | (s)(CH₂)₄ | | H | H | H | CH | CH | c-C₃H₅ |
| 171 | rac(CH₂)₃ | | H | H | H | CH | CH | c-C₃H₅ |
| 172 | rac(CH₂)₄ | | H | H | H | CH | CH | c-C₃H₅ |
| 173 | (R)(CH₂)₃ | | H | H | H | CH | CH | c-C₃H₅ |
| 174 | (R)(CH₂)₄ | | H | H | H | CH | CH | c-C₃H₅ |
| 175 | CH₂CH=CH₂ | H | H | H | H | CH | C—Cl | c-C₃H₅ |
| 176 | CH₂-c-C₃H₅ | H | H | H | H | CH | C—Cl | c-C₃H₅ |
| 177 | CH₂CH₂CH₃ | H | H | H | H | CH | C—Cl | c-C₃H₅ |
| 178 | CH₂CH=CH₂ | (s)CH₃ | H | H | H | CH | C—Cl | c-C₃H₅ |
| 179 | CH₂-c-C₃H₅ | (s)CH₃ | H | H | H | CH | C—Cl | c-C₃H₅ |
| 180 | CH₂CH₃ | (s)CH₃ | H | H | H | CH | C—Cl | c-C₃H₅ |
| 181 | CH₂CH₂CH₃ | (s)CH₃ | H | H | H | CH | C—Cl | c-C₃H₅ |
| 182 | CH₂CH=CH₂ | rac-CH₃ | H | H | H | CH | C—Cl | c-C₃H₅ |
| 183 | CH₂-c-C₃H₅ | rac-CH₃ | H | H | H | CH | C—Cl | c-C₃H₅ |
| 184 | CH₂CH₃ | rac-CH₃ | H | H | H | CH | C—Cl | c-C₃H₅ |
| 185 | CH₂CH₂CH₃ | rac-CH₃ | H | H | H | CH | C—Cl | c-C₃H₅ |
| 186 | CH₂CH=CH₂ | (R)CH₃ | H | H | H | CH | C—Cl | c-C₃H₅ |
| 187 | CH₂-c-C₃H₅ | (R)CH₃ | H | H | H | CH | C—Cl | c-C₃H₅ |
| 188 | CH₂CH₃ | (R)CH₃ | H | H | H | CH | C—Cl | c-C₃H₅ |
| 189 | CH₂CH₂CH₃ | (R)CH₃ | H | H | H | CH | C—Cl | c-C₃H₅ |
| 190 | CH₂CH=CH₂ | H | H | H | H | CH | C—CH₃ | c-C₃H₅ |
| 191 | CH₂-c-C₃H₅ | H | H | H | H | CH | C—CH₃ | c-C₃H₅ |
| 192 | CH₂CH₂CH₃ | H | H | H | H | CH | C—CH₃ | c-C₃H₅ |
| 193 | CH₂CH=CH₂ | (s)CH₃ | H | H | H | CH | C—CH₃ | c-C₃H₅ |
| 194 | CH₂-c-C₃H₅ | (s)CH₃ | H | H | H | CH | C—CH₃ | c-C₃H₅ |
| 195 | CH₂CH₃ | (s)CH₃ | H | H | H | CH | C—CH₃ | c-C₃H₅ |
| 196 | CH₂CH₂CH₃ | (s)CH₃ | H | H | H | CH | C—CH₃ | c-C₃H₅ |
| 197 | CH₂CH=CH₂ | rac-CH₃ | H | H | H | CH | C—CH₃ | c-C₃H₅ |
| 198 | CH₂-c-C₃H₅ | rac-CH₃ | H | H | H | CH | C—CH₃ | c-C₃H₅ |
| 199 | CH₂CH₃ | rac-CH₃ | H | H | H | CH | C—CH₃ | c-C₃H₅ |
| 200 | CH₂CH₂CH₃ | rac-CH₃ | H | H | H | CH | C—CH₃ | c-C₃H₅ |
| 201 | CH₂CH=CH₂ | (R)CH₃ | H | H | H | CH | C—CH₃ | c-C₃H₅ |
| 202 | CH₂-c-C₃H₅ | (R)CH₃ | H | H | H | CH | C—CH₃ | c-C₃H₅ |
| 203 | CH₂CH₃ | (R)CH₃ | H | H | H | CH | C—CH₃ | c-C₃H₅ |
| 204 | CH₂CH₂CH₃ | (R)CH₃ | H | H | H | CH | C—CH₃ | c-C₃H₅ |
| 205 | CH₂CH=CH₂ | H | H | H | H | C—Cl | CH | c-C₃H₅ |
| 206 | CH₂-c-C₃H₅ | H | H | H | H | C—Cl | CH | c-C₃H₅ |
| 207 | CH₂CH₂CH₃ | H | H | H | H | C—Cl | CH | c-C₃H₅ |
| 208 | CH₂CH=CH₂ | (s)CH₃ | H | H | H | C—Cl | CH | c-C₃H₅ |
| 209 | CH₂-c-C₃H₅ | (s)CH₃ | H | H | H | C—Cl | CH | c-C₃H₅ |
| 210 | CH₂CH₂CH₃ | (s)CH₃ | H | H | H | C—Cl | CH | c-C₃H₅ |
| 211 | CH₂CH=CH₂ | rac-CH₃ | H | H | H | C—Cl | CH | c-C₃H₅ |
| 212 | CH₂-c-C₃H₅ | rac-CH₃ | H | H | H | C—Cl | CH | c-C₃H₅ |
| 213 | CH₂CH₂CH₃ | rac-CH₃ | H | H | H | C—Cl | CH | c-C₃H₅ |
| 214 | CH₂CH=CH₂ | H | H | H | H | C—CH₃ | CH | c-C₃H₅ |
| 215 | CH₂-c-C₃H₅ | H | H | H | H | C—CH₃ | CH | c-C₃H₅ |
| 216 | CH₂CH₂CH₃ | H | H | H | H | C—CH₃ | CH | c-C₃H₅ |
| 217 | CH₂CH=CH₂ | (s)CH₃ | H | H | H | C—CH₃ | CH | c-C₃H₅ |
| 218 | CH₂-c-C₃H₅ | (s)CH₃ | H | H | H | C—CH₃ | CH | c-C₃H₅ |
| 219 | CH₂CH₃ | (s)CH₃ | H | H | H | C—CH₃ | CH | C-C₃H₅ |
| 220 | CH₂CH₂CH₃ | (s)CH₃ | H | H | H | C—CH₃ | CH | c-C₃H₅ |
| 221 | CH₂CH=CH₂ | rac-CH₃ | H | H | H | C—CH₃ | CH | c-C₃H₅ |
| 222 | CH₂-c-C₃H₅ | rac-CH₃ | H | H | H | C—CH₃ | CH | c-C₃H₅ |
| 223 | CH₂CH₂CH₃ | rac-CH₃ | H | H | H | C—CH₃ | CH | c-C₃H₅ |
| 224 | CH₂CH=CH₂ | (R)CH₃ | H | H | H | C—CH₃ | CH | c-C₃H₅ |
| 225 | CH₂-c-C₃H₅ | (R)CH₃ | H | H | H | C—CH₃ | CH | c-C₃H₅ |
| 226 | CH₂CH₂CH₃ | (R)CH₃ | H | H | H | C—CH₃ | CH | c-C₃H₅ |
| 227 | H | H | H | H | H | CH | CH | C₂H₅ |
| 228 | CH₃ | H | H | H | H | CH | CH | C₂H₅ |
| 229 | CH₂CH₃ | H | H | H | H | CH | CH | C₂H₅ |
| 230 | CH₂CH=CH₂ | H | H | H | H | CH | CH | C₂H₅ |
| 231 | CH₂-c-C₃H₅ | H | H | H | H | CH | CH | C₂H₅ |
| 232 | CH₂CH₂CH₃ | H | H | H | H | CH | CH | C₂H₅ |
| 233 | H | (s)CH₃ | H | H | H | CH | CH | C₂H₅ |
| 234 | CH₃ | (s)CH₃ | H | H | H | CH | CH | C₂H₅ |
| 235 | CH₂CH₃ | (s)CH₃ | H | H | H | CH | CH | C₂H₅ |
| 236 | CH₂CH=CH₂ | (s)CH₃ | H | H | H | CH | CH | C₂H₅ |
| 237 | CH₂-c-C₃H₅ | (s)CH₃ | H | H | H | CH | CH | C₂H₅ |
| 238 | CH₂CH₂CH₃ | (s)CH₃ | H | H | H | CH | CH | C₂H₅ |
| 239 | CH₃ | rac-CH₃ | H | H | H | CH | CH | C₂H₅ |

TABLE 1-continued

| No. | R¹ | R²ᵃ | R²ᵇ | R²ᶜ | R³ | X | Y | Rᵇ |
|---|---|---|---|---|---|---|---|---|
| 240 | CH₂CH=CH₂ | rac-CH₃ | H | H | H | CH | CH | C₂H₅ |
| 241 | CH₂-c-C₃H₅ | rac-CH₃ | H | H | H | CH | CH | C₂H₅ |
| 242 | CH₂CH₂CH₃ | rac-CH₃ | H | H | H | CH | CH | C₂H₅ |
| 243 | CH₃ | (R)CH₃ | H | H | H | CH | CH | C₂H₅ |
| 244 | CH₂CH₃ | (R)CH₃ | H | H | H | CH | CH | C₂H₅ |
| 245 | CH₂CH=CH₂ | (R)CH₃ | H | H | H | CH | CH | C₂H₅ |
| 246 | CH₂-c-C₃H₅ | (R)CH₃ | H | H | H | CH | CH | C₂H₅ |
| 247 | CH₂CH₂CH₃ | (R)CH₃ | H | H | H | CH | CH | C₂H₅ |
| 248 | CH₃ | H | CH₃ | H | H | CH | CH | C₂H₅ |
| 249 | CH₂CH=CH₂ | H | CH₃ | H | H | CH | CH | C₂H₅ |
| 250 | CH₂-c-C₃H₅ | H | CH₃ | H | H | CH | CH | C₂H₅ |
| 251 | CH₂CH₂CH₃ | H | CH₃ | H | H | CH | CH | C₂H₅ |
| 252 | CH₃ | CH₃ | H | CH₃ | H | CH | CH | C₂H₅ |
| 253 | CH₂CH=CH₂ | CH₃ | H | CH₃ | H | CH | CH | C₂H₅ |
| 254 | CH₂-c-C₃H₅ | CH₃ | H | CH₃ | H | CH | CH | C₂H₅ |
| 255 | CH₂CH₂CH₃ | CH₃ | H | CH₃ | H | CH | CH | C₂H₅ |
| 256 | CH₃ | CH₃ | CH₃ | H | H | CH | CH | C₂H₅ |
| 257 | CH₂CH=CH₂ | CH₃ | CH₃ | H | H | CH | CH | C₂H₅ |
| 258 | CH₂-c-C₃H₅ | CH₃ | CH₃ | H | H | CH | CH | C₂H₅ |
| 259 | CH₂CH₂CH₃ | CH₃ | CH₃ | H | H | CH | CH | C₂H₅ |
| 260 | (s)(CH₂)₃ | | H | H | H | CH | CH | C₂H₅ |
| 261 | (s)(CH₂)₄ | | H | H | H | CH | CH | C₂H₅ |
| 262 | rac(CH₂)₃ | | H | H | H | CH | CH | C₂H₅ |
| 263 | rac(CH₂)₄ | | H | H | H | CH | CH | C₂H₅ |
| 264 | (R)(CH₂)₃ | | H | H | H | CH | CH | C₂H₅ |
| 265 | (R)(CH₂)₄ | | H | H | H | CH | CH | C₂H₅ |
| 266 | H | H | H | H | H | CH | CH | CH₃ |
| 267 | CH₃ | H | H | H | H | CH | CH | CH₃ |
| 268 | CH₂CH₃ | H | H | H | H | CH | CH | CH₃ |
| 269 | CH₂CH=CH₂ | H | H | H | H | CH | CH | CH₃ |
| 270 | CH₂-c-C₃H₅ | H | H | H | H | CH | CH | CH₃ |
| 271 | CH₂CH₂CH₃ | H | H | H | H | CH | CH | CH₃ |
| 272 | H | (s)CH₃ | H | H | H | CH | CH | CH₃ |
| 273 | CH₃ | (s)CH₃ | H | H | H | CH | CH | CH₃ |
| 274 | CH₂CH₃ | (s)CH₃ | H | H | H | CH | CH | CH₃ |
| 275 | CH₂CH=CH₂ | (s)CH₃ | H | H | H | CH | CH | CH₃ |
| 276 | CH₂-c-C₃H₅ | (s)CH₃ | H | H | H | CH | CH | CH₃ |
| 277 | CH₂CH₂CH₃ | (s)CH₃ | H | H | H | CH | CH | CH₃ |
| 278 | CH₂CH=CH₂ | rac-CH₃ | H | H | H | CH | CH | CH₃ |
| 279 | CH₂CH₂CH₃ | rac-CH₃ | H | H | H | CH | CH | CH₃ |
| 280 | CH₂CH₃ | (R)CH₃ | H | H | H | CH | CH | CH₃ |
| 281 | CH₂CH=CH₂ | (R)CH₃ | H | H | H | CH | CH | CH₃ |
| 282 | CH₂-c-C₃H₅ | (R)CH₃ | H | H | H | CH | CH | CH₃ |
| 283 | CH₂CH₂CH₃ | (R)CH₃ | H | H | H | CH | CH | CH₃ |
| 284 | CH₂CH=CH₂ | H | CH₃ | H | H | CH | CH | CH₃ |
| 285 | CH₂CH₂CH₃ | H | CH₃ | H | H | CH | CH | CH₃ |
| 286 | CH₂CH=CH₂ | CH₃ | H | CH₃ | H | CH | CH | CH₃ |
| 287 | CH₂CH₂CH₃ | CH₃ | H | CH₃ | H | CH | CH | CH₃ |
| 288 | CH₂CH=CH₂ | CH₃ | CH₃ | H | H | CH | CH | CH₃ |
| 289 | CH₂CH₂CH₃ | CH₃ | CH₃ | H | H | CH | CH | CH₃ |
| 290 | (s)(CH₂)₃ | | H | H | H | CH | CH | CH₃ |
| 291 | (s)(CH₂)₄ | | H | H | H | CH | CH | CH₃ |
| 292 | rac(CH₂)₃ | | H | H | H | CH | CH | CH₃ |
| 293 | rac(CH₂)₄ | | H | H | H | CH | CH | CH₃ |
| 294 | (R)(CH₂)₃ | | H | H | H | CH | CH | CH₃ |
| 295 | (R)(CH₂)₄ | | H | H | H | CH | CH | CH₃ |
| 296 | H | H | H | H | H | N | CH | CH(CH₃)₂ |
| 297 | CH₃ | H | H | H | H | N | CH | CH(CH₃)₂ |
| 298 | CH₂CH₃ | H | H | H | H | N | CH | CH(CH₃)₂ |
| 299 | CH₂CH=CH₂ | H | H | H | H | N | CH | CH(CH₃)₂ |
| 300 | CH₂-c-C₃H₅ | H | H | H | H | N | CH | CH(CH₃)₂ |
| 301 | CH₂CH₂CH₃ | H | H | H | H | N | CH | CH(CH₃)₂ |
| 302 | H | (s)CH₃ | H | H | H | N | CH | CH(CH₃)₂ |
| 303 | CH₃ | (s)CH₃ | H | H | H | N | CH | CH(CH₃)₂ |
| 304 | CH₂CH₃ | (s)CH₃ | H | H | H | N | CH | CH(CH₃)₂ |
| 305 | CH₂CH=CH₂ | (s)CH₃ | H | H | H | N | CH | CH(CH₃)₂ |
| 306 | CH₂-c-C₃H₅ | (s)CH₃ | H | H | H | N | CH | CH(CH₃)₂ |
| 307 | CH₂CH₂CH₃ | (s)CH₃ | H | H | H | N | CH | CH(CH₃)₂ |
| 308 | CH₂CH=CH₂ | rac-CH₃ | H | H | H | N | CH | CH(CH₃)₂ |
| 309 | CH₂CH₂CH₃ | rac-CH₃ | H | H | H | N | CH | CH(CH₃)₂ |
| 310 | CH₂CH₃ | (R)CH₃ | H | H | H | N | CH | CH(CH₃)₂ |
| 311 | CH₂CH=CH₂ | (R)CH₃ | H | H | H | N | CH | CH(CH₃)₂ |
| 312 | CH₂-c-C₃H₅ | (R)CH₃ | H | H | H | N | CH | CH(CH₃)₂ |
| 313 | CH₂CH₂CH₃ | (R)CH₃ | H | H | H | N | CH | CH(CH₃)₂ |
| 314 | (s)(CH₂)₃ | | H | H | H | N | CH | CH(CH₃)₂ |
| 315 | (s)(CH₂)₄ | | H | H | H | N | CH | CH(CH₃)₂ |
| 316 | rac(CH₂)₃ | | H | H | H | N | CH | CH(CH₃)₂ |

TABLE 1-continued

| No. | R¹ | R²ᵃ | R²ᵇ | R²ᶜ | R³ | X | Y | Rᵇ |
|---|---|---|---|---|---|---|---|---|
| 317 | rac(CH₂)₄ | | H | H | H | N | CH | CH(CH₃)₂ |
| 318 | (R)(CH₂)₃ | | H | H | H | N | CH | CH(CH₃)₂ |
| 319 | (R)(CH₂)₄ | | H | H | H | N | CH | CH(CH₃)₂ |
| 320 | H | H | H | H | H | N | CH | CH=CH₂ |
| 321 | CH₃ | H | H | H | H | N | CH | CH=CH₂ |
| 322 | CH₂CH₃ | H | H | H | H | N | CH | CH=CH₂ |
| 323 | CH₂CH=CH₂ | H | H | H | H | N | CH | CH=CH₂ |
| 324 | CH₂-c-C₃H₅ | H | H | H | H | N | CH | CH=CH₂ |
| 325 | CH₂CH₂CH₃ | H | H | H | H | N | CH | CH=CH₂ |
| 326 | H | (s)CH₃ | H | H | H | N | CH | CH=CH₂ |
| 327 | CH₃ | (s)CH₃ | H | H | H | N | CH | CH=CH₂ |
| 328 | CH₂CH₃ | (s)CH₃ | H | H | H | N | CH | CH=CH₂ |
| 329 | CH₂CH=CH₂ | (s)CH₃ | H | H | H | N | CH | CH=CH₂ |
| 330 | CH₂-c-C₃H₅ | (s)CH₃ | H | H | H | N | CH | CH=CH₂ |
| 331 | CH₂CH₂CH₃ | (s)CH₃ | H | H | H | N | CH | CH=CH₂ |
| 332 | CH₂CH=CH₂ | (R)CH₃ | H | H | H | N | CH | CH=CH₂ |
| 333 | CH₂CH₂CH₃ | (R)CH₃ | H | H | H | N | CH | CH=CH₂ |
| 334 | CH₂CH=CH₂ | rac-CH₃ | H | H | H | N | CH | CH=CH₂ |
| 335 | CH₂CH₂CH₃ | rac-CH₃ | H | H | H | N | CH | CH=CH₂ |
| 336 | H | H | H | H | H | N | CH | c-C₃H₅ |
| 337 | CH₃ | H | H | H | H | N | CH | c-C₃H₅ |
| 338 | CH₂CH₃ | H | H | H | H | N | CH | c-C₃H₅ |
| 339 | CH₂CH=CH₂ | H | H | H | H | N | CH | c-C₃H₅ |
| 340 | CH₂-c-C₃H₅ | H | H | H | H | N | CH | c-C₃H₅ |
| 341 | CH₂CH₂CH₃ | H | H | H | H | N | CH | c-C₃H₅ |
| 342 | H | (s)CH₃ | H | H | H | N | CH | c-C₃H₅ |
| 343 | CH₃ | (s)CH₃ | H | H | H | N | CH | c-C₃H₅ |
| 344 | CH₂CH₃ | (s)CH₃ | H | H | H | N | CH | c-C₃H₅ |
| 345 | CH₂CH=CH₂ | (s)CH₃ | H | H | H | N | CH | c-C₃H₅ |
| 346 | CH₂-c-C₃H₅ | (s)CH₃ | H | H | H | N | CH | c-C₃H₅ |
| 347 | CH₂CH₂CH₃ | (s)CH₃ | H | H | H | N | CH | c-C₃H₅ |
| 348 | CH₂CH₃ | (R)CH₃ | H | H | H | N | CH | c-C₃H₅ |
| 349 | CH₂CH=CH₂ | (R)CH₃ | H | H | H | N | CH | c-C₃H₅ |
| 350 | CH₂CH₂CH₃ | (R)CH₃ | H | H | H | N | CH | c-C₃H₅ |
| 351 | CH₂CH=CH₂ | rac-CH₃ | H | H | H | N | CH | c-C₃H₅ |
| 352 | CH₂CH₂CH₃ | rac-CH₃ | H | H | H | N | CH | c-C₃H₅ |
| 353 | H | H | H | H | H | N | CH | CH₃ |
| 354 | CH₃ | H | H | H | H | N | CH | CH₃ |
| 355 | CH₂CH₃ | H | H | H | H | N | CH | CH₃ |
| 356 | CH₂CH=CH₂ | H | H | H | H | N | CH | CH₃ |
| 357 | CH₂-c-C₃H₅ | H | H | H | H | N | CH | CH₃ |
| 358 | CH₂CH₂CH₃ | H | H | H | H | N | CH | CH₃ |
| 359 | H | (s)CH₃ | H | H | H | N | CH | CH₃ |
| 360 | CH₃ | (s)CH₃ | H | H | H | N | CH | CH₃ |
| 361 | CH₂CH₃ | (s)CH₃ | H | H | H | N | CH | CH₃ |
| 362 | CH₂CH=CH₂ | (s)CH₃ | H | H | H | N | CH | CH₃ |
| 363 | CH₂-c-C₃H₅ | (s)CH₃ | H | H | H | N | CH | CH₃ |
| 364 | CH₂CH₂CH₃ | (s)CH₃ | H | H | H | N | CH | CH₃ |
| 365 | CH₂CH=CH₂ | (R)CH₃ | H | H | H | N | CH | CH₃ |
| 366 | CH₂CH₂CH₃ | (R)CH₃ | H | H | H | N | CH | CH₃ |
| 367 | CH₂CH=CH₂ | rac-CH₃ | H | H | H | N | CH | CH₃ |
| 368 | CH₂CH₂CH₃ | rac-CH₃ | H | H | H | N | CH | CH₃ |
| 369 | H | H | H | H | H | N | CH | CF₃ |
| 370 | CH₃ | H | H | H | H | N | CH | CF₃ |
| 371 | CH₂CH₃ | H | H | H | H | N | CH | CF₃ |
| 372 | CH₂CH=CH₂ | H | H | H | H | N | CH | CF₃ |
| 373 | CH₂-c-C₃H₅ | H | H | H | H | N | CH | CF₃ |
| 374 | CH₂CH₂CH₃ | H | H | H | H | N | CH | CF₃ |
| 375 | H | (s)CH₃ | H | H | H | N | CH | CF₃ |
| 376 | CH₃ | (s)CH₃ | H | H | H | N | CH | CF₃ |
| 377 | CH₂CH₃ | (s)CH₃ | H | H | H | N | CH | CF₃ |
| 378 | CH₂CH=CH₂ | (s)CH₃ | H | H | H | N | CH | CF₃ |
| 379 | CH₂-c-C₃H₅ | (s)CH₃ | H | H | H | N | CH | CF₃ |
| 380 | CH₂CH₂CH₃ | (s)CH₃ | H | H | H | N | CH | CF₃ |
| 381 | CH₂CH=CH₂ | (R)CH₃ | H | H | H | N | CH | CF₃ |
| 382 | CH₂CH₂CH₃ | (R)CH₃ | H | H | H | N | CH | CF₃ |
| 383 | CH₂CH=CH₂ | rac-CH₃ | H | H | H | N | CH | CF₃ |
| 384 | CH₂CH₂CH₃ | rac-CH₃ | H | H | H | N | CH | CF₃ |
| 385 | H | H | H | H | H | CH | N | CH(CH₃)₂ |
| 386 | CH₃ | H | H | H | H | CH | N | CH(CH₃)₂ |
| 387 | CH₂CH₃ | H | H | H | H | CH | N | CH(CH₃)₂ |
| 388 | CH₂CH=CH₂ | H | H | H | H | CH | N | CH(CH₃)₂ |
| 389 | CH₂-c-C₃H₅ | H | H | H | H | CH | N | CH(CH₃)₂ |
| 390 | CH₂CH₂CH₃ | H | H | H | H | CH | N | CH(CH₃)₂ |
| 391 | H | (s)CH₃ | H | H | H | CH | N | CH(CH₃)₂ |
| 392 | CH₃ | (s)CH₃ | H | H | H | CH | N | CH(CH₃)₂ |
| 393 | CH₂CH₃ | (s)CH₃ | H | H | H | CH | N | CH(CH₃)₂ |

TABLE 1-continued

| No. | R¹ | R²ᵃ | R²ᵇ | R²ᶜ | R³ | X | Y | Rᵇ |
|---|---|---|---|---|---|---|---|---|
| 394 | CH₂CH=CH₂ | (s)CH₃ | H | H | H | CH | N | CH(CH₃)₂ |
| 395 | CH₂-c-C₃H₅ | (s)CH₃ | H | H | H | CH | N | CH(CH₃)₂ |
| 396 | CH₂CH₂CH₃ | (s)CH₃ | H | H | H | CH | N | CH(CH₃)₂ |
| 397 | CH₂CH=CH₂ | rac-CH₃ | H | H | H | CH | N | CH(CH₃)₂ |
| 398 | CH₂CH₂CH₃ | rac-CH₃ | H | H | H | CH | N | CH(CH₃)₂ |
| 399 | CH₂CH₃ | (R)CH₃ | H | H | H | CH | N | CH(CH₃)₂ |
| 400 | CH₂CH=CH₂ | (R)CH₃ | H | H | H | CH | N | CH(CH₃)₂ |
| 401 | CH₂-c-C₃H₅ | (R)CH₃ | H | H | H | CH | N | CH(CH₃)₂ |
| 402 | CH₂CH₂CH₃ | (R)CH₃ | H | H | H | CH | N | CH(CH₃)₂ |
| 403 | H | H | H | H | H | CH | N | CH=CH₂ |
| 404 | CH₃ | H | H | H | H | CH | N | CH=CH₂ |
| 405 | CH₂CH₃ | H | H | H | H | CH | N | CH=CH₂ |
| 406 | CH₂CH=CH₂ | H | H | H | H | CH | N | CH=CH₂ |
| 407 | CH₂-c-C₃H₅ | H | H | H | H | CH | N | CH=CH₂ |
| 408 | CH₂CH₂CH₃ | H | H | H | H | CH | N | CH=CH₂ |
| 409 | H | (s)CH₃ | H | H | H | CH | N | CH=CH₂ |
| 410 | CH₃ | (s)CH₃ | H | H | H | CH | N | CH=CH₂ |
| 411 | CH₂CH₃ | (s)CH₃ | H | H | H | CH | N | CH=CH₂ |
| 412 | CH₂CH=CH₂ | (s)CH₃ | H | H | H | CH | N | CH=CH₂ |
| 413 | CH₂-c-C₃H₅ | (s)CH₃ | H | H | H | CH | N | CH=CH₂ |
| 414 | CH₂CH₂CH₃ | (s)CH₃ | H | H | H | CH | N | CH=CH₂ |
| 415 | CH₂CH=CH₂ | rac-CH₃ | H | H | H | CH | N | CH=CH₂ |
| 416 | CH₂CH₂CH₃ | rac-CH₃ | H | H | H | CH | N | CH=CH₂ |
| 417 | CH₂CH₃ | (R)CH₃ | H | H | H | CH | N | CH=CH₂ |
| 418 | CH₂CH=CH₂ | (R)CH₃ | H | H | H | CH | N | CH=CH₂ |
| 419 | CH₂-c-C₃H₅ | (R)CH₃ | H | H | H | CH | N | CH=CH₂ |
| 420 | CH₂CH₂CH₃ | (R)CH₃ | H | H | H | CH | N | CH=CH₂ |
| 421 | H | H | H | H | H | CH | N | c-C₃H₅ |
| 422 | CH₃ | H | H | H | H | CH | N | c-C₃H₅ |
| 423 | CH₂CH₃ | H | H | H | H | CH | N | c-C₃H₅ |
| 424 | CH₂CH=CH₂ | H | H | H | H | CH | N | c-C₃H₅ |
| 425 | CH₂-c-C₃H₅ | H | H | H | H | CH | N | c-C₃H₅ |
| 426 | CH₂CH₂CH₃ | H | H | H | H | CH | N | c-C₃H₅ |
| 427 | H | (s)CH₃ | H | H | H | CH | N | c-C₃H₅ |
| 428 | CH₃ | (s)CH₃ | H | H | H | CH | N | c-C₃H₅ |
| 429 | CH₂CH₃ | (s)CH₃ | H | H | H | CH | N | c-C₃H₅ |
| 430 | CH₂CH=CH₂ | (s)CH₃ | H | H | H | CH | N | c-C₃H₅ |
| 431 | CH₂-c-C₃H₅ | (s)CH₃ | H | H | H | CH | N | c-C₃H₅ |
| 432 | CH₂CH₂CH₃ | (s)CH₃ | H | H | H | CH | N | c-C₃H₅ |
| 433 | CH₂CH=CH₂ | rac-CH₃ | H | H | H | CH | N | c-C₃H₅ |
| 434 | CH₂CH₂CH₃ | rac-CH₃ | H | H | H | CH | N | c-C₃H₅ |
| 435 | CH₂CH₃ | (R)CH₃ | H | H | H | CH | N | c-C₃H₅ |
| 436 | CH₂CH=CH₂ | (R)CH₃ | H | H | H | CH | N | c-C₃H₅ |
| 437 | CH₂-c-C₃H₅ | (R)CH₃ | H | H | H | CH | N | c-C₃H₅ |
| 438 | CH₂CH₂CH₃ | (R)CH₃ | H | H | H | CH | N | c-C₃H₅ |
| 439 | H | H | H | H | H | CH | N | CH₃ |
| 440 | CH₃ | H | H | H | H | CH | N | CH₃ |
| 441 | CH₂CH₃ | H | H | H | H | CH | N | CH₃ |
| 442 | CH₂CH=CH₂ | H | H | H | H | CH | N | CH₃ |
| 443 | CH₂-c-C₃H₅ | H | H | H | H | CH | N | CH₃ |
| 444 | CH₂CH₂CH₃ | H | H | H | H | CH | N | CH₃ |
| 445 | H | (s)CH₃ | H | H | H | CH | N | CH₃ |
| 446 | CH₃ | (s)CH₃ | H | H | H | CH | N | CH₃ |
| 447 | CH₂CH₃ | (s)CH₃ | H | H | H | CH | N | CH₃ |
| 448 | CH₂CH=CH₂ | (s)CH₃ | H | H | H | CH | N | CH₃ |
| 449 | CH₂-c-C₃H₅ | (s)CH₃ | H | H | H | CH | N | CH₃ |
| 450 | CH₂CH₂CH₃ | (s)CH₃ | H | H | H | CH | N | CH₃ |
| 451 | CH₂CH=CH₂ | rac-CH₃ | H | H | H | CH | N | CH₃ |
| 452 | CH₂CH₂CH₃ | rac-CH₃ | H | H | H | CH | N | CH₃ |
| 453 | CH₂CH₃ | (R)CH₃ | H | H | H | CH | N | CH₃ |
| 454 | CH₂CH=CH₂ | (R)CH₃ | H | H | H | CH | N | CH₃ |
| 455 | CH₂-c-C₃H₅ | (R)CH₃ | H | H | H | CH | N | CH₃ |
| 456 | CH₂CH₂CH₃ | (R)CH₃ | H | H | H | CH | N | CH₃ |
| 457 | H | H | H | H | H | CH | N | CF₃ |
| 458 | CH₃ | H | H | H | H | CH | N | CF₃ |
| 459 | CH₂CH₃ | H | H | H | H | CH | N | CF₃ |
| 460 | CH₂CH=CH₂ | H | H | H | H | CH | N | CF₃ |
| 461 | CH₂-c-C₃H₅ | H | H | H | H | CH | N | CF₃ |
| 462 | CH₂CH₂CH₃ | H | H | H | H | CH | N | CF₃ |
| 463 | H | (s)CH₃ | H | H | H | CH | N | CF₃ |
| 464 | CH₃ | (s)CH₃ | H | H | H | CH | N | CF₃ |
| 465 | CH₂CH₃ | (s)CH₃ | H | H | H | CH | N | CF₃ |
| 466 | CH₂CH=CH₂ | (s)CH₃ | H | H | H | CH | N | CF₃ |
| 467 | CH₂-c-C₃H₅ | (s)CH₃ | H | H | H | CH | N | CF₃ |
| 468 | CH₂CH₂CH₃ | (s)CH₃ | H | H | H | CH | N | CF₃ |
| 469 | CH₂CH₃ | (R)CH₃ | H | H | H | CH | N | CF₃ |
| 470 | CH₂CH=CH₂ | (R)CH₃ | H | H | H | CH | N | CF₃ |

TABLE 1-continued

| No. | R¹ | R²ᵃ | R²ᵇ | R²ᶜ | R³ | X | Y | Rᵇ |
|---|---|---|---|---|---|---|---|---|
| 471 | CH₂-c-C₃H₅ | (R)CH₃ | H | H | H | CH | N | CF₃ |
| 472 | CH₂CH₂CH₃ | (R)CH₃ | H | H | H | CH | N | CF₃ |
| 473 | CH₂CH=CH₂ | rac-CH₃ | H | H | H | CH | N | CF₃ |
| 474 | CH₂CH₂CH₃ | rac-CH₃ | H | H | H | CH | N | CF₃ |
| 475 | H | H | H | H | CH₃ | CH | CH | CH(CH₃)₂ |
| 476 | CH₃ | H | H | H | CH₃ | CH | CH | CH(CH₃)₂ |
| 477 | CH₂CH₃ | H | H | H | CH₃ | CH | CH | CH(CH₃)₂ |
| 478 | CH₂CH=CH₂ | H | H | H | CH₃ | CH | CH | CH(CH₃)₂ |
| 479 | CH₂-c-C₃H₅ | H | H | H | CH₃ | CH | CH | CH(CH₃)₂ |
| 480 | CH₂CH₂CH₃ | H | H | H | CH₃ | CH | CH | CH(CH₃)₂ |
| 481 | H | (s)CH₃ | H | H | CH₃ | CH | CH | CH(CH₃)₂ |
| 482 | CH₃ | (s)CH₃ | H | H | CH₃ | CH | CH | CH(CH₃)₂ |
| 483 | CH₂CH₃ | (s)CH₃ | H | H | CH₃ | CH | CH | CH(CH₃)₂ |
| 484 | CH₂CH=CH₂ | (s)CH₃ | H | H | CH₃ | CH | CH | CH(CH₃)₂ |
| 485 | CH₂-c-C₃H₅ | (s)CH₃ | H | H | CH₃ | CH | CH | CH(CH₃)₂ |
| 486 | CH₂CH₂CH₃ | (s)CH₃ | H | H | CH₃ | CH | CH | CH(CH₃)₂ |
| 487 | CH₃ | rac-CH₃ | H | H | CH₃ | CH | CH | CH(CH₃)₂ |
| 488 | CH₂CH=CH₂ | rac-CH₃ | H | H | CH₃ | CH | CH | CH(CH₃)₂ |
| 489 | CH₂-c-C₃H₅ | rac-CH₃ | H | H | CH₃ | CH | CH | CH(CH₃)₂ |
| 490 | CH₂CH₂CH₃ | rac-CH₃ | H | H | CH₃ | CH | CH | CH(CH₃)₂ |
| 491 | CH₃ | (R)CH₃ | H | H | CH₃ | CH | CH | CH(CH₃)₂ |
| 492 | CH₂CH=CH₂ | (R)CH₃ | H | H | CH₃ | CH | CH | CH(CH₃)₂ |
| 493 | CH₂-c-C₃H₅ | (R)CH₃ | H | H | CH₃ | CH | CH | CH(CH₃)₂ |
| 494 | CH₂CH₂CH₃ | (R)CH₃ | H | H | CH₃ | CH | CH | CH(CH₃)₂ |
| 495 | CH₃ | H | CH₃ | H | CH₃ | CH | CH | CH(CH₃)₂ |
| 496 | CH₂CH=CH₂ | H | CH₃ | H | CH₃ | CH | CH | CH(CH₃)₂ |
| 497 | CH₂-c-C₃H₅ | H | CH₃ | H | CH₃ | CH | CH | CH(CH₃)₂ |
| 498 | CH₂CH₂CH₃ | H | CH₃ | H | CH₃ | CH | CH | CH(CH₃)₂ |
| 499 | CH₃ | CH₃ | H | CH₃ | CH₃ | CH | CH | CH(CH₃)₂ |
| 500 | CH₂CH=CH₂ | CH₃ | H | CH₃ | CH₃ | CH | CH | CH(CH₃)₂ |
| 501 | CH₂-c-C₃H₅ | CH₃ | H | CH₃ | CH₃ | CH | CH | CH(CH₃)₂ |
| 502 | CH₂CH₂CH₃ | CH₃ | H | CH₃ | CH₃ | CH | CH | CH(CH₃)₂ |
| 503 | CH₃ | CH₃ | CH₃ | H | CH₃ | CH | CH | CH(CH₃)₂ |
| 504 | CH₂CH=CH₂ | CH₃ | CH₃ | H | CH₃ | CH | CH | CH(CH₃)₂ |
| 505 | CH₂-c-C₃H₅ | CH₃ | CH₃ | H | CH₃ | CH | CH | CH(CH₃)₂ |
| 506 | CH₂CH₂CH₃ | CH₃ | CH₃ | H | CH₃ | CH | CH | CH(CH₃)₂ |
| 507 | (S)(CH₂)₃ | | H | H | CH₃ | CH | CH | CH(CH₃)₂ |
| 508 | (S)(CH₂)₄ | | H | H | CH₃ | CH | CH | CH(CH₃)₂ |
| 509 | rac(CH₂)₃ | | H | H | CH₃ | CH | CH | CH(CH₃)₂ |
| 510 | rac(CH₂)₄ | | H | H | CH₃ | CH | CH | CH(CH₃)₂ |
| 511 | (R)(CH₂)₃ | | H | H | CH₃ | CH | CH | CH(CH₃)₂ |
| 512 | (R)(CH₂)₄ | | H | H | CH₃ | CH | CH | CH(CH₃)₂ |
| 513 | CH₂CH=CH₂ | H | H | H | CH₃ | C—Cl | CH | CH(CH₃)₂ |
| 514 | CH₂-c-C₃H₅ | H | H | H | CH₃ | C—Cl | CH | CH(CH₃)₂ |
| 515 | CH₂CH₂CH₃ | H | H | H | CH₃ | C—Cl | CH | CH(CH₃)₂ |
| 516 | CH₂CH=CH₂ | (s)CH₃ | H | H | CH₃ | C—Cl | CH | CH(CH₃)₂ |
| 517 | CH₂-c-C₃H₅ | (s)CH₃ | H | H | CH₃ | C—Cl | CH | CH(CH₃)₂ |
| 518 | CH₂CH₃ | (s)CH₃ | H | H | CH₃ | C—Cl | CH | CH(CH₃)₂ |
| 519 | CH₂CH₂CH₃ | (s)CH₃ | H | H | CH₃ | C—Cl | CH | CH(CH₃)₂ |
| 520 | CH₂CH=CH₂ | rac-CH₃ | H | H | CH₃ | C—Cl | CH | CH(CH₃)₂ |
| 521 | CH₂-c-C₃H₅ | rac-CH₃ | H | H | CH₃ | C—Cl | CH | CH(CH₃)₂ |
| 522 | CH₂CH₃ | rac-CH₃ | H | H | CH₃ | C—Cl | CH | CH(CH₃)₂ |
| 523 | CH₂CH₂CH₃ | rac-CH₃ | H | H | CH₃ | C—Cl | CH | CH(CH₃)₂ |
| 524 | CH₂CH=CH₂ | (R)CH₃ | H | H | CH₃ | C—Cl | CH | CH(CH₃)₂ |
| 525 | CH₂-c-C₃H₅ | (R)CH₃ | H | H | CH₃ | C—Cl | CH | CH(CH₃)₂ |
| 526 | CH₂CH₂CH₃ | (R)CH₃ | H | H | CH₃ | C—Cl | CH | CH(CH₃)₂ |
| 527 | CH₂CH₃ | (R)CH₃ | H | H | CH₃ | C—Cl | CH | CH(CH₃)₂ |
| 528 | CH₂CH=CH₂ | H | CH₃ | H | CH₃ | C—Cl | CH | CH(CH₃)₂ |
| 529 | CH₂-c-C₃H₅ | H | CH₃ | H | CH₃ | C—Cl | CH | CH(CH₃)₂ |
| 530 | CH₂CH₂CH₃ | H | CH₃ | H | CH₃ | C—Cl | CH | CH(CH₃)₂ |
| 531 | CH₂CH=CH₂ | CH₃ | H | CH₃ | CH₃ | C—Cl | CH | CH(CH₃)₂ |
| 532 | CH₂-c-C₃H₅ | CH₃ | H | CH₃ | CH₃ | C—Cl | CH | CH(CH₃)₂ |
| 533 | CH₂CH₂CH₃ | CH₃ | H | CH₃ | CH₃ | C—Cl | CH | CH(CH₃)₂ |
| 534 | CH₂CH=CH₂ | CH₃ | CH₃ | H | CH₃ | C—Cl | CH | CH(CH₃)₂ |
| 535 | CH₂-c-C₃H₅ | CH₃ | CH₃ | H | CH₃ | C—Cl | CH | CH(CH₃)₂ |
| 536 | CH₂CH₂CH₃ | CH₃ | CH₃ | H | CH₃ | C—Cl | CH | CH(CH₃)₂ |
| 537 | (CH₂)₃ | | H | H | CH₃ | C—Cl | CH | CH(CH₃)₂ |
| 538 | (CH₂)₄ | | H | H | CH₃ | C—Cl | CH | CH(CH₃)₂ |
| 539 | CH₂CH=CH₂ | H | H | H | CH₃ | CH | C—Cl | CH(CH₃)₂ |
| 540 | CH₂-c-C₃H₅ | H | H | H | CH₃ | CH | C—Cl | CH(CH₃)₂ |
| 541 | CH₂CH₂CH₃ | H | H | H | CH₃ | CH | C—Cl | CH(CH₃)₂ |
| 542 | CH₂CH=CH₂ | (s)CH₃ | H | H | CH₃ | CH | C—Cl | CH(CH₃)₂ |
| 543 | CH₂-c-C₃H₅ | (s)CH₃ | H | H | CH₃ | CH | C—Cl | CH(CH₃)₂ |
| 544 | CH₂CH₂CH₃ | (s)CH₃ | H | H | CH₃ | CH | C—Cl | CH(CH₃)₂ |
| 545 | CH₂CH₃ | (s)CH₃ | H | H | CH₃ | CH | C—Cl | CH(CH₃)₂ |
| 546 | CH₂CH=CH₂ | rac-CH₃ | H | H | CH₃ | CH | C—Cl | CH(CH₃)₂ |
| 547 | CH₂-c-C₃H₅ | rac-CH₃ | H | H | CH₃ | CH | C—Cl | CH(CH₃)₂ |

TABLE 1-continued

| No. | R¹ | R²ᵃ | R²ᵇ | R²ᶜ | R³ | X | Y | Rᵇ |
|---|---|---|---|---|---|---|---|---|
| 548 | CH₂CH₃ | rac-CH₃ | H | H | CH₃ | CH | C—Cl | CH(CH₃)₂ |
| 549 | CH₂CH₂CH₃ | rac-CH₃ | H | H | CH₃ | CH | C—Cl | CH(CH₃)₂ |
| 550 | CH₂CH=CH₂ | (R)CH₃ | H | H | CH₃ | CH | C—Cl | CH(CH₃)₂ |
| 551 | CH₂-c-C₃H₅ | (R)CH₃ | H | H | CH₃ | CH | C—Cl | CH(CH₃)₂ |
| 552 | CH₂CH₃ | (R)CH₃ | H | H | CH₃ | CH | C—Cl | CH(CH₃)₂ |
| 553 | CH₂CH₂CH₃ | (R)CH₃ | H | H | CH₃ | CH | C—Cl | CH(CH₃)₂ |
| 554 | CH₂CH=CH₂ | H | CH₃ | H | CH₃ | CH | C—Cl | CH(CH₃)₂ |
| 555 | CH₂-c-C₃H₅ | H | CH₃ | H | CH₃ | CH | C—Cl | CH(CH₃)₂ |
| 556 | CH₂CH₂CH₃ | H | CH₃ | H | CH₃ | CH | C—Cl | CH(CH₃)₂ |
| 557 | CH₂CH=CH₂ | CH₃ | H | CH₃ | CH₃ | CH | C—Cl | CH(CH₃)₂ |
| 558 | CH₂-c-C₃H₅ | CH₃ | H | CH₃ | CH₃ | CH | C—Cl | CH(CH₃)₂ |
| 559 | CH₂CH₂CH₃ | CH₃ | H | CH₃ | CH₃ | CH | C—Cl | CH(CH₃)₂ |
| 560 | CH₂CH=CH₂ | CH₃ | CH₃ | H | CH₃ | CH | C—Cl | CH(CH₃)₂ |
| 561 | CH₂-c-C₃H₅ | CH₃ | CH₃ | H | CH₃ | CH | C—Cl | CH(CH₃)₂ |
| 562 | CH₂CH₂CH₃ | CH₃ | CH₃ | H | CH₃ | CH | C—Cl | CH(CH₃)₂ |
| 563 | (CH₂)₃ | | H | H | CH₃ | CH | C—Cl | CH(CH₃)₂ |
| 564 | (CH₂)₄ | | H | H | CH₃ | CH | C—Cl | CH(CH₃)₂ |
| 565 | CH₂CH=CH₂ | H | H | H | CH₃ | C—CH₃ | CH | CH(CH₃)₂ |
| 566 | CH₂-c-C₃H₅ | H | H | H | CH₃ | C—CH₃ | CH | CH(CH₃)₂ |
| 567 | CH₂CH₂CH₃ | H | H | H | CH₃ | C—CH₃ | CH | CH(CH₃)₂ |
| 568 | CH₂CH=CH₂ | (s)CH₃ | H | H | CH₃ | C—CH₃ | CH | CH(CH₃)₂ |
| 569 | CH₂-c-C₃H₅ | (s)CH₃ | H | H | CH₃ | C—CH₃ | CH | CH(CH₃)₂ |
| 570 | CH₂CH₂CH₃ | (s)CH₃ | H | H | CH₃ | C—CH₃ | CH | CH(CH₃)₂ |
| 571 | CH₂CH=CH₂ | rac-CH₃ | H | H | CH₃ | C—CH₃ | CH | CH(CH₃)₂ |
| 572 | CH₂-c-C₃H₅ | rac-CH₃ | H | H | CH₃ | C—CH₃ | CH | CH(CH₃)₂ |
| 573 | CH₂CH₂CH₃ | rac-CH₃ | H | H | CH₃ | C—CH₃ | CH | CH(CH₃)₂ |
| 574 | CH₂CH=CH₂ | (R)CH₃ | H | H | CH₃ | C—CH₃ | CH | CH(CH₃)₂ |
| 575 | CH₂-c-C₃H₅ | (R)CH₃ | H | H | CH₃ | C—CH₃ | CH | CH(CH₃)₂ |
| 576 | CH₂CH₂CH₃ | (R)CH₃ | H | H | CH₃ | C—CH₃ | CH | CH(CH₃)₂ |
| 577 | CH₂CH=CH₂ | H | CH₃ | H | CH₃ | C—CH₃ | CH | CH(CH₃)₂ |
| 578 | CH₂-c-C₃H₅ | H | CH₃ | H | CH₃ | C—CH₃ | CH | CH(CH₃)₂ |
| 579 | CH₂CH₂CH₃ | H | CH₃ | H | CH₃ | C—CH₃ | CH | CH(CH₃)₂ |
| 580 | CH₂CH=CH₂ | CH₃ | H | CH₃ | CH₃ | C—CH₃ | CH | CH(CH₃)₂ |
| 581 | CH₂-c-C₃H₅ | CH₃ | H | CH₃ | CH₃ | C—CH₃ | CH | CH(CH₃)₂ |
| 582 | CH₂CH₂CH₃ | CH₃ | H | CH₃ | CH₃ | C—CH₃ | CH | CH(CH₃)₂ |
| 583 | CH₂CH=CH₂ | CH₃ | CH₃ | H | CH₃ | C—CH₃ | CH | CH(CH₃)₂ |
| 584 | CH₂-c-C₃H₅ | CH₃ | CH₃ | H | CH₃ | C—CH₃ | CH | CH(CH₃)₂ |
| 585 | CH₂CH₂CH₃ | CH₃ | CH₃ | H | CH₃ | C—CH₃ | CH | CH(CH₃)₂ |
| 586 | (CH₂)₃ | | H | H | CH₃ | C—CH₃ | CH | CH(CH₃)₂ |
| 587 | (CH₂)₄ | | H | H | CH₃ | C—CH₃ | CH | CH(CH₃)₂ |
| 588 | CH₂CH=CH₂ | H | H | H | CH₃ | CH | C—CH₃ | CH(CH₃)₂ |
| 589 | CH₂-c-C₃H₅ | H | H | H | CH₃ | CH | C—CH₃ | CH(CH₃)₂ |
| 590 | CH₂CH₂CH₃ | H | H | H | CH₃ | CH | C—CH₃ | CH(CH₃)₂ |
| 591 | CH₂CH=CH₂ | (s)CH₃ | H | H | CH₃ | CH | C—CH₃ | CH(CH₃)₂ |
| 592 | CH₂-c-C₃H₅ | (s)CH₃ | H | H | CH₃ | CH | C—CH₃ | CH(CH₃)₂ |
| 593 | CH₂CH₂CH₃ | (s)CH₃ | H | H | CH₃ | CH | C—CH₃ | CH(CH₃)₂ |
| 594 | CH₂CH=CH₂ | rac-CH₃ | H | H | CH₃ | CH | C—CH₃ | CH(CH₃)₂ |
| 595 | CH₂-c-C₃H₅ | rac-CH₃ | H | H | CH₃ | CH | C—CH₃ | CH(CH₃)₂ |
| 596 | CH₂CH₂CH₃ | rac-CH₃ | H | H | CH₃ | CH | C—CH₃ | CH(CH₃)₂ |
| 597 | CH₂CH=CH₂ | (R)CH₃ | H | H | CH₃ | CH | C—CH₃ | CH(CH₃)₂ |
| 598 | CH₂-c-C₃H₅ | (R)CH₃ | H | H | CH₃ | CH | C—CH₃ | CH(CH₃)₂ |
| 599 | CH₂CH₂CH₃ | (R)CH₃ | H | H | CH₃ | CH | C—CH₃ | CH(CH₃)₂ |
| 600 | CH₂CH=CH₂ | H | CH₃ | H | CH₃ | CH | C—CH₃ | CH(CH₃)₂ |
| 601 | CH₂-c-C₃H₅ | H | CH₃ | H | CH₃ | CH | C—CH₃ | CH(CH₃)₂ |
| 602 | CH₂CH₂CH₃ | H | CH₃ | H | CH₃ | CH | C—CH₃ | CH(CH₃)₂ |
| 603 | CH₂CH=CH₂ | CH₃ | H | CH₃ | CH₃ | CH | C—CH₃ | CH(CH₃)₂ |
| 604 | CH₂-c-C₃H₅ | CH₃ | H | CH₃ | CH₃ | CH | C—CH₃ | CH(CH₃)₂ |
| 605 | CH₂CH₂CH₃ | CH₃ | H | CH₃ | CH₃ | CH | C—CH₃ | CH(CH₃)₂ |
| 606 | CH₂CH=CH₂ | CH₃ | CH₃ | H | CH₃ | CH | C—CH₃ | CH(CH₃)₂ |
| 607 | CH₂-c-C₃H₅ | CH₃ | CH₃ | H | CH₃ | CH | C—CH₃ | CH(CH₃)₂ |
| 608 | CH₂CH₂CH₃ | CH₃ | CH₃ | H | CH₃ | CH | C—CH₃ | CH(CH₃)₂ |
| 609 | (CH₂)₃ | | H | H | CH₃ | CH | C—CH₃ | CH(CH₃)₂ |
| 610 | (CH₂)₄ | | H | H | CH₃ | CH | C—CH₃ | CH(CH₃)₂ |
| 611 | H | H | H | H | CH₃ | CH | CH | c-C₃H₅ |
| 612 | CH₃ | H | H | H | CH₃ | CH | CH | c-C₃H₅ |
| 613 | CH₂CH₃ | H | H | H | CH₃ | CH | CH | c-C₃H₅ |
| 614 | CH₂CH=CH₂ | H | H | H | CH₃ | CH | CH | c-C₃H₅ |
| 615 | CH₂-c-C₃H₅ | H | H | H | CH₃ | CH | CH | c-C₃H₅ |
| 616 | CH₂CH₂CH₃ | H | H | H | CH₃ | CH | CH | c-C₃H₅ |
| 617 | H | (s)CH₃ | H | H | CH₃ | CH | CH | c-C₃H₅ |
| 618 | CH₃ | (s)CH₃ | H | H | CH₃ | CH | CH | c-C₃H₅ |
| 619 | CH₂CH₃ | (s)CH₃ | H | H | CH₃ | CH | CH | c-C₃H₅ |
| 620 | CH₂CH=CH₂ | (s)CH₃ | H | H | CH₃ | CH | CH | c-C₃H₅ |
| 621 | CH₂-c-C₃H₅ | (s)CH₃ | H | H | CH₃ | CH | CH | c-C₃H₅ |
| 622 | CH₂CH₂CH₃ | (s)CH₃ | H | H | CH₃ | CH | CH | c-C₃H₅ |
| 623 | CH₃ | rac-CH₃ | H | H | CH₃ | CH | CH | c-C₃H₅ |
| 624 | CH₂CH=CH₂ | rac-CH₃ | H | H | CH₃ | CH | CH | c-C₃H₅ |

TABLE 1-continued

| No. | R¹ | R²ᵃ | R²ᵇ | R²ᶜ | R³ | X | Y | Rᵇ |
|---|---|---|---|---|---|---|---|---|
| 625 | CH₂-c-C₃H₅ | rac-CH₃ | H | H | CH₃ | CH | CH | c-C₃H₅ |
| 626 | CH₂CH₂CH₃ | rac-CH₃ | H | H | CH₃ | CH | CH | c-C₃H₅ |
| 627 | CH₂CH₃ | (R)CH₃ | H | H | CH₃ | CH | CH | c-C₃H₅ |
| 628 | CH₂CH=CH₂ | (R)CH₃ | H | H | CH₃ | CH | CH | c-C₃H₅ |
| 629 | CH₂-c-C₃H₅ | (R)CH₃ | H | H | CH₃ | CH | CH | c-C₃H₅ |
| 630 | CH₂CH₂CH₃ | (R)CH₃ | H | H | CH₃ | CH | CH | c-C₃H₅ |
| 631 | CH₃ | H | CH₃ | H | CH₃ | CH | CH | c-C₃H₅ |
| 632 | CH₂CH=CH₂ | H | CH₃ | H | CH₃ | CH | CH | c-C₃H₅ |
| 633 | CH₂-c-C₃H₅ | H | CH₃ | H | CH₃ | CH | CH | c-C₃H₅ |
| 634 | CH₂CH₂CH₃ | H | CH₃ | H | CH₃ | CH | CH | c-C₃H₅ |
| 635 | CH₃ | CH₃ | H | CH₃ | CH₃ | CH | CH | c-C₃H₅ |
| 636 | CH₂CH=CH₂ | CH₃ | H | CH₃ | CH₃ | CH | CH | c-C₃H₅ |
| 637 | CH₂-c-C₃H₅ | CH₃ | H | CH₃ | CH₃ | CH | CH | c-C₃H₅ |
| 638 | CH₂CH₂CH₃ | CH₃ | H | CH₃ | CH₃ | CH | CH | c-C₃H₅ |
| 639 | CH₃ | CH₃ | CH₃ | H | CH₃ | CH | CH | c-C₃H₅ |
| 640 | CH₂CH=CH₂ | CH₃ | CH₃ | H | CH₃ | CH | CH | c-C₃H₅ |
| 641 | CH₂-c-C₃H₅ | CH₃ | CH₃ | H | CH₃ | CH | CH | c-C₃H₅ |
| 642 | CH₂CH₂CH₃ | CH₃ | CH₃ | H | CH₃ | CH | CH | c-C₃H₅ |
| 643 | (s)(CH₂)₃ | | H | H | CH₃ | CH | CH | c-C₃H₅ |
| 644 | (s)(CH₂)₄ | | H | H | CH₃ | CH | CH | c-C₃H₅ |
| 645 | rac(CH₂)₃ | | H | H | CH₃ | CH | CH | c-C₃H₅ |
| 646 | rac(CH₂)₄ | | H | H | CH₃ | CH | CH | c-C₃H₅ |
| 647 | (R)(CH₂)₃ | | H | H | CH₃ | CH | CH | c-C₃H₅ |
| 648 | (R)(CH₂)₄ | | H | H | CH₃ | CH | CH | c-C₃H₅ |
| 649 | CH₂CH=CH₂ | H | H | H | CH₃ | CH | C—Cl | c-C₃H₅ |
| 650 | CH₂-c-C₃H₅ | H | H | H | CH₃ | CH | C—Cl | c-C₃H₅ |
| 651 | CH₂CH₂CH₃ | H | H | H | CH₃ | CH | C—Cl | c-C₃H₅ |
| 652 | CH₂CH=CH₂ | (s)CH₃ | H | H | CH₃ | CH | C—Cl | c-C₃H₅ |
| 653 | CH₂-c-C₃H₅ | (s)CH₃ | H | H | CH₃ | CH | C—Cl | c-C₃H₅ |
| 654 | CH₂CH₃ | (s)CH₃ | H | H | CH₃ | CH | C—Cl | c-C₃H₅ |
| 655 | CH₂CH₂CH₃ | (s)CH₃ | H | H | CH₃ | CH | C—Cl | c-C₃H₅ |
| 656 | CH₂CH=CH₂ | rac-CH₃ | H | H | CH₃ | CH | C—Cl | c-C₃H₅ |
| 657 | CH₂-c-C₃H₅ | rac-CH₃ | H | H | CH₃ | CH | C—Cl | c-C₃H₅ |
| 658 | CH₂CH₃ | rac-CH₃ | H | H | CH₃ | CH | C—Cl | c-C₃H₅ |
| 659 | CH₂CH₂CH₃ | rac-CH₃ | H | H | CH₃ | CH | C—Cl | c-C₃H₅ |
| 660 | CH₂CH=CH₂ | (R)CH₃ | H | H | CH₃ | CH | C—Cl | c-C₃H₅ |
| 661 | CH₂-c-C₃H₅ | (R)CH₃ | H | H | CH₃ | CH | C—Cl | c-C₃H₅ |
| 662 | CH₂CH₂CH₃ | (R)CH₃ | H | H | CH₃ | CH | C—Cl | c-C₃H₅ |
| 663 | CH₂CH₃ | (R)CH₃ | H | H | CH₃ | CH | C—Cl | c-C₃H₅ |
| 664 | CH₂CH=CH₂ | H | H | H | CH₃ | CH | C—CH₃ | c-C₃H₅ |
| 665 | CH₂-c-C₃H₅ | H | H | H | CH₃ | CH | C—CH₃ | c-C₃H₅ |
| 666 | CH₂CH₂CH₃ | H | H | H | CH₃ | CH | C—CH₃ | c-C₃H₅ |
| 667 | CH₂CH=CH₂ | (s)CH₃ | H | H | CH₃ | CH | C—CH₃ | c-C₃H₅ |
| 668 | CH₂-c-C₃H₅ | (s)CH₃ | H | H | CH₃ | CH | C—CH₃ | c-C₃H₅ |
| 669 | CH₂CH₂CH₃ | (s)CH₃ | H | H | CH₃ | CH | C—CH₃ | c-C₃H₅ |
| 670 | CH₂CH=CH₂ | rac-CH₃ | H | H | CH₃ | CH | C—CH₃ | c-C₃H₅ |
| 671 | CH₂-c-C₃H₅ | rac-CH₃ | H | H | CH₃ | CH | C—CH₃ | c-C₃H₅ |
| 672 | CH₂CH₂CH₃ | rac-CH₃ | H | H | CH₃ | CH | C—CH₃ | c-C₃H₅ |
| 673 | CH₂CH=CH₂ | (R)CH₃ | H | H | CH₃ | CH | C—CH₃ | c-C₃H₅ |
| 674 | CH₂-c-C₃H₅ | (R)CH₃ | H | H | CH₃ | CH | C—CH₃ | c-C₃H₅ |
| 675 | CH₂CH₂CH₃ | (R)CH₃ | H | H | CH₃ | CH | C—CH₃ | c-C₃H₅ |
| 676 | CH₂CH=CH₂ | H | H | H | CH₃ | C—Cl | CH | c-C₃H₅ |
| 677 | CH₂-c-C₃H₅ | H | H | H | CH₃ | C—Cl | CH | c-C₃H₅ |
| 678 | CH₂CH₂CH₃ | H | H | H | CH₃ | C—Cl | CH | c-C₃H₅ |
| 679 | CH₂CH=CH₂ | (s)CH₃ | H | H | CH₃ | C—Cl | CH | c-C₃H₅ |
| 680 | CH₂-c-C₃H₅ | (s)CH₃ | H | H | CH₃ | C—Cl | CH | c-C₃H₅ |
| 681 | CH₂CH₃ | (s)CH₃ | H | H | CH₃ | C—Cl | CH | c-C₃H₅ |
| 682 | CH₂CH₂CH₃ | (s)CH₃ | H | H | CH₃ | C—Cl | CH | c-C₃H₅ |
| 683 | CH₂CH=CH₂ | rac-CH₃ | H | H | CH₃ | C—Cl | CH | c-C₃H₅ |
| 684 | CH₂-c-C₃H₅ | rac-CH₃ | H | H | CH₃ | C—Cl | CH | c-C₃H₅ |
| 685 | CH₂CH₂CH₃ | rac-CH₃ | H | H | CH₃ | C—Cl | CH | c-C₃H₅ |
| 686 | CH₂CH=CH₂ | (R)CH₃ | H | H | CH₃ | C—Cl | CH | c-C₃H₅ |
| 687 | CH₂-c-C₃H₅ | (R)CH₃ | H | H | CH₃ | C—Cl | CH | c-C₃H₅ |
| 688 | CH₂CH₃ | (R)CH₃ | H | H | CH₃ | C—Cl | CH | c-C₃H₅ |
| 689 | CH₂CH₂CH₃ | (R)CH₃ | H | H | CH₃ | C—Cl | CH | c-C₃H₅ |
| 690 | CH₂CH=CH₂ | H | H | H | CH₃ | C—CH₃ | CH | c-C₃H₅ |
| 691 | CH₂-c-C₃H₅ | H | H | H | CH₃ | C—CH₃ | CH | c-C₃H₅ |
| 692 | CH₂CH₂CH₃ | H | H | H | CH₃ | C—CH₃ | CH | c-C₃H₅ |
| 693 | CH₂CH=CH₂ | (s)CH₃ | H | H | CH₃ | C—CH₃ | CH | c-C₃H₅ |
| 694 | CH₂-c-C₃H₅ | (s)CH₃ | H | H | CH₃ | C—CH₃ | CH | c-C₃H₅ |
| 695 | CH₂CH₂CH₃ | (s)CH₃ | H | H | CH₃ | C—CH₃ | CH | c-C₃H₅ |
| 696 | CH₂CH=CH₂ | rac-CH₃ | H | H | CH₃ | C—CH₃ | CH | c-C₃H₅ |
| 697 | CH₂-c-C₃H₅ | rac-CH₃ | H | H | CH₃ | C—CH₃ | CH | c-C₃H₅ |
| 698 | CH₂CH₂CH₃ | rac-CH₃ | H | H | CH₃ | C—CH₃ | CH | c-C₃H₅ |
| 699 | CH₃ | H | H | H | CH₃ | CH | CH | C₂H₅ |
| 700 | CH₂CH=CH₂ | H | H | H | CH₃ | CH | CH | C₂H₅ |
| 701 | CH₂-c-C₃H₅ | H | H | H | CH₃ | CH | CH | C₂H₅ |

TABLE 1-continued

| No. | R¹ | R²ᵃ | R²ᵇ | R²ᶜ | R³ | X | Y | Rᵇ |
|---|---|---|---|---|---|---|---|---|
| 702 | CH₂CH₂CH₃ | H | H | H | CH₃ | CH | CH | C₂H₅ |
| 703 | CH₃ | (s)CH₃ | H | H | CH₃ | CH | CH | C₂H₅ |
| 704 | CH₂CH=CH₂ | (s)CH₃ | H | H | CH₃ | CH | CH | C₂H₅ |
| 705 | CH₂-c-C₃H₅ | (s)CH₃ | H | H | CH₃ | CH | CH | C₂H₅ |
| 706 | CH₂CH₃ | (s)CH₃ | H | H | CH₃ | CH | CH | C₂H₅ |
| 707 | CH₂CH₂CH₃ | (s)CH₃ | H | H | CH₃ | CH | CH | C₂H₅ |
| 708 | CH₂CH=CH₂ | rac-CH₃ | H | H | CH₃ | CH | CH | C₂H₅ |
| 709 | CH₂CH₂CH₃ | rac-CH₃ | H | H | CH₃ | CH | CH | C₂H₅ |
| 710 | CH₃ | (R)CH₃ | H | H | CH₃ | CH | CH | C₂H₅ |
| 711 | CH₂CH=CH₂ | (R)CH₃ | H | H | CH₃ | CH | CH | C₂H₅ |
| 712 | CH₂-c-C₃H₅ | (R)CH₃ | H | H | CH₃ | CH | CH | C₂H₅ |
| 713 | CH₂CH=CH₂ | H | CH₃ | H | CH₃ | CH | CH | C₂H₅ |
| 714 | CH₂CH₂CH₃ | H | CH₃ | H | CH₃ | CH | CH | C₂H₅ |
| 715 | CH₂CH=CH₂ | CH₃ | H | CH₃ | CH₃ | CH | CH | C₂H₅ |
| 716 | CH₂CH₂CH₃ | CH₃ | H | CH₃ | CH₃ | CH | CH | C₂H₅ |
| 717 | CH₂CH=CH₂ | CH₃ | CH₃ | H | CH₃ | CH | CH | C₂H₅ |
| 718 | CH₂CH₂CH₃ | CH₃ | CH₃ | H | CH₃ | CH | CH | C₂H₅ |
| 719 | (s)(CH₂)₃ | | H | H | CH₃ | CH | CH | C₂H₅ |
| 720 | (s)(CH₂)₄ | | H | H | CH₃ | CH | CH | C₂H₅ |
| 721 | rac(CH₂)₃ | | H | H | CH₃ | CH | CH | C₂H₅ |
| 722 | rac(CH₂)₄ | | H | H | CH₃ | CH | CH | C₂H₅ |
| 723 | H | H | H | H | CH₃ | CH | CH | CH=CH₂ |
| 724 | CH₃ | H | H | H | CH₃ | CH | CH | CH=CH₂ |
| 725 | CH₂CH₃ | H | H | H | CH₃ | CH | CH | CH=CH₂ |
| 726 | CH₂CH=CH₂ | H | H | H | CH₃ | CH | CH | CH=CH₂ |
| 727 | CH₂-c-C₃H₅ | H | H | H | CH₃ | CH | CH | CH=CH₂ |
| 728 | CH₂CH₂CH₃ | H | H | H | CH₃ | CH | CH | CH=CH₂ |
| 729 | H | (s)CH₃ | H | H | CH₃ | CH | CH | CH=CH₂ |
| 730 | CH₃ | (s)CH₃ | H | H | CH₃ | CH | CH | CH=CH₂ |
| 731 | CH₂CH₃ | (s)CH₃ | H | H | CH₃ | CH | CH | CH=CH₂ |
| 732 | CH₂CH=CH₂ | (s)CH₃ | H | H | CH₃ | CH | CH | CH=CH₂ |
| 733 | CH₂-c-C₃H₅ | (s)CH₃ | H | H | CH₃ | CH | CH | CH=CH₂ |
| 734 | CH₂CH₂CH₃ | (s)CH₃ | H | H | CH₃ | CH | CH | CH=CH₂ |
| 735 | CH₂CH=CH₂ | rac-CH₃ | H | H | CH₃ | CH | CH | CH=CH₂ |
| 736 | CH₂CH₂CH₃ | rac-CH₃ | H | H | CH₃ | CH | CH | CH=CH₂ |
| 737 | CH₂CH₃ | (s)CH₃ | H | H | CH₃ | CH | CH | CH=CH₂ |
| 738 | CH₂CH=CH₂ | (R)CH₃ | H | H | CH₃ | CH | CH | CH=CH₂ |
| 739 | CH₂-c-C₃H₅ | (R)CH₃ | H | H | CH₃ | CH | CH | CH=CH₂ |
| 740 | CH₂CH₂CH₃ | (R)CH₃ | H | H | CH₃ | CH | CH | CH=CH₂ |
| 741 | CH₂CH=CH₂ | H | CH₃ | H | CH₃ | CH | CH | CH=CH₂ |
| 742 | CH₂CH₂CH₃ | H | CH₃ | H | CH₃ | CH | CH | CH=CH₂ |
| 743 | CH₂CH=CH₂ | CH₃ | H | CH₃ | CH₃ | CH | CH | CH=CH₂ |
| 744 | CH₂CH₂CH₃ | CH₃ | H | CH₃ | CH₃ | CH | CH | CH=CH₂ |
| 745 | CH₂CH=CH₂ | CH₃ | CH₃ | H | CH₃ | CH | CH | CH=CH₂ |
| 746 | CH₂CH₂CH₃ | CH₃ | CH₃ | H | CH₃ | CH | CH | CH=CH₂ |
| 747 | (CH₂)₃ | | H | H | CH₃ | CH | CH | CH=CH₂ |
| 748 | (CH₂)₄ | | H | H | CH₃ | CH | CH | CH=CH₂ | rac: racemate;
(S): S configuration;
(R) R configuration.

Other examples of compounds according to the invention are the compounds of the general formulae Ia.3, Ib, Ic, Id, Ie and If:

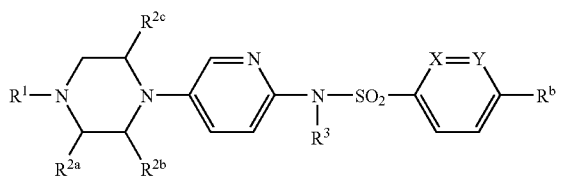

(Ia.3)

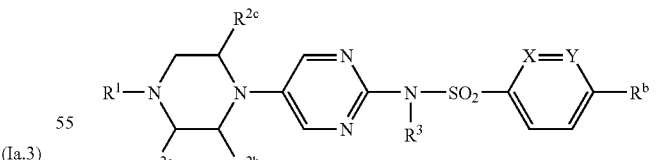

(Ib)

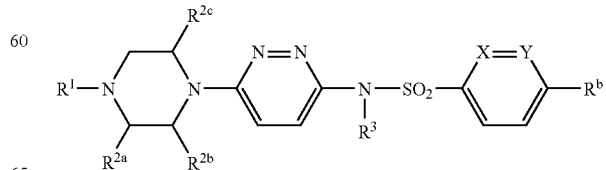

(Ic)

-continued

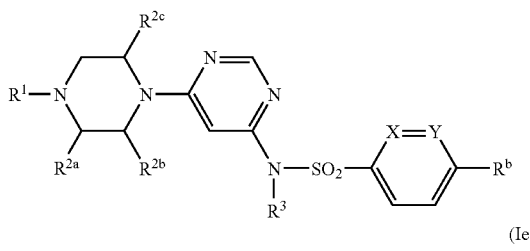
(Id)

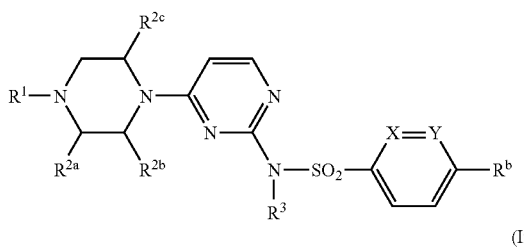
(Ie)

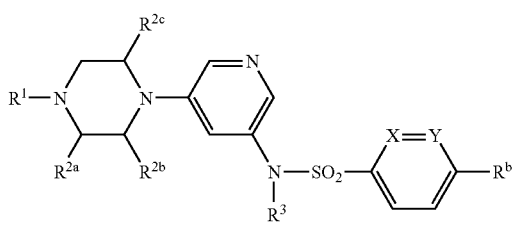
(If)

in which $R^1$, $R^{2a}$, $R^{2b}$, $R^{2c}$, $R^3$, X, Y and $R^b$ have the meanings specified in one line in Table 1.

Among the compounds of the general formula I, preference is also given to the compounds of the general formula Ig

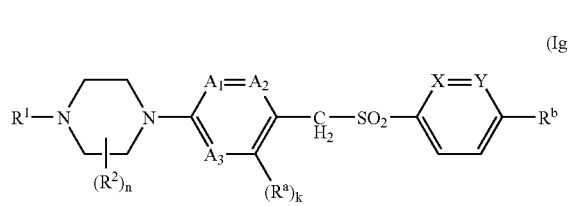
(Ig)

in which n, k, $R^1$, $R^2$, $R^a$, $R^b$, $A^1$, $A^2$, $A^3$, X and Y have the meanings given for formula Ia.

Among the compounds of the general formula I, preference is also given to the compounds of the general formula Ih

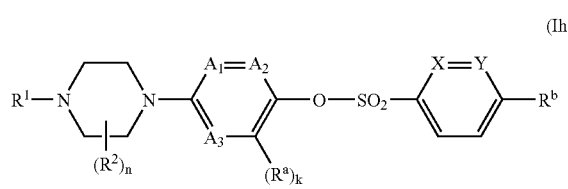
(Ih)

in which n, k, $R^1$, $R^2$, $R^a$, $R^b$, $A^1$, $A^2$, $A^3$, X and Y have the meanings given for formula Ia.

Among the compounds of general formulae Ig and Ih, preference is given to the compounds of general formula Ig.1, Ig.2, Ih.1 and Ih.2

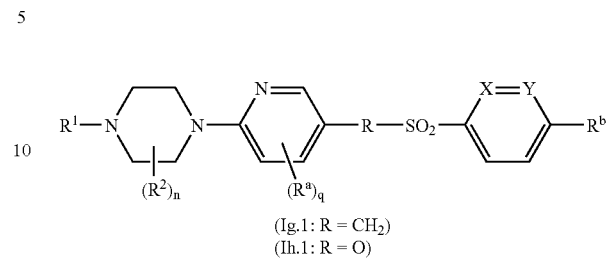
(Ig.1: R = CH$_2$)
(Ih.1: R = O)

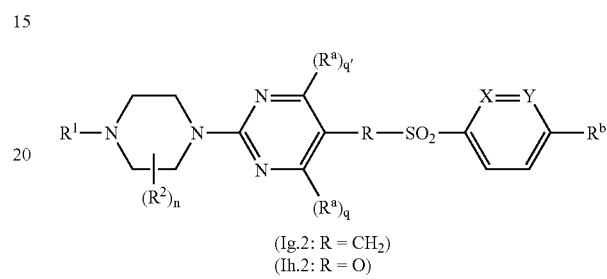
(Ig.2: R = CH$_2$)
(Ih.2: R = O)

in which n, q, q', X, Y, $R^1$, $R^2$, $R^a$ and $R^b$ have the meanings mentioned previously for formulae Ia.1 and Ia.2 and R is CH$_2$ (compounds Ig.1 and Ig.2) or O (compounds Ih.1 or Ih.2).

Examples of compounds of the formula Ig.1 and Ih.1 are the compounds of the following general formulae Ig.1a, Ig.1b, Ig.1c, Ig.1d, Ig.1e, Ig.1f, Ig.1g, Ig.1h, Ig.1k, Ih.1a, Ih.1b, Ih.1c, Ih.1h, Ih.1e, Ih.1f, Ih.1g, Ih.1h andIh.1k:

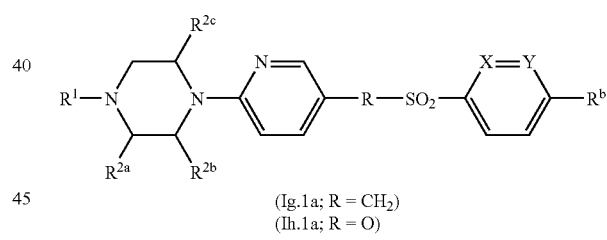
(Ig.1a; R = CH$_2$)
(Ih.1a; R = O)

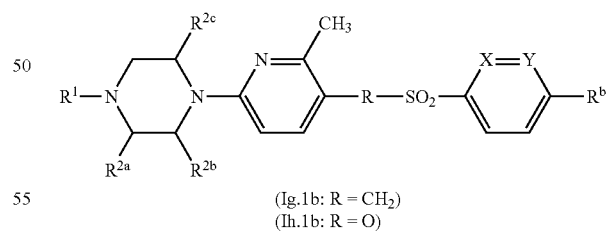
(Ig.1b: R = CH$_2$)
(Ih.1b: R = O)

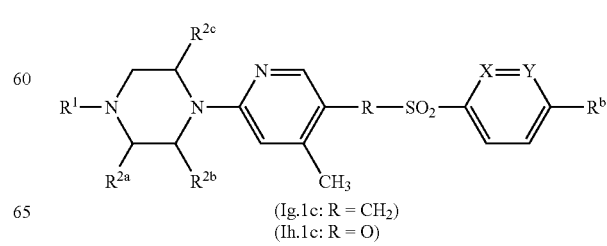
(Ig.1c: R = CH$_2$)
(Ih.1c: R = O)

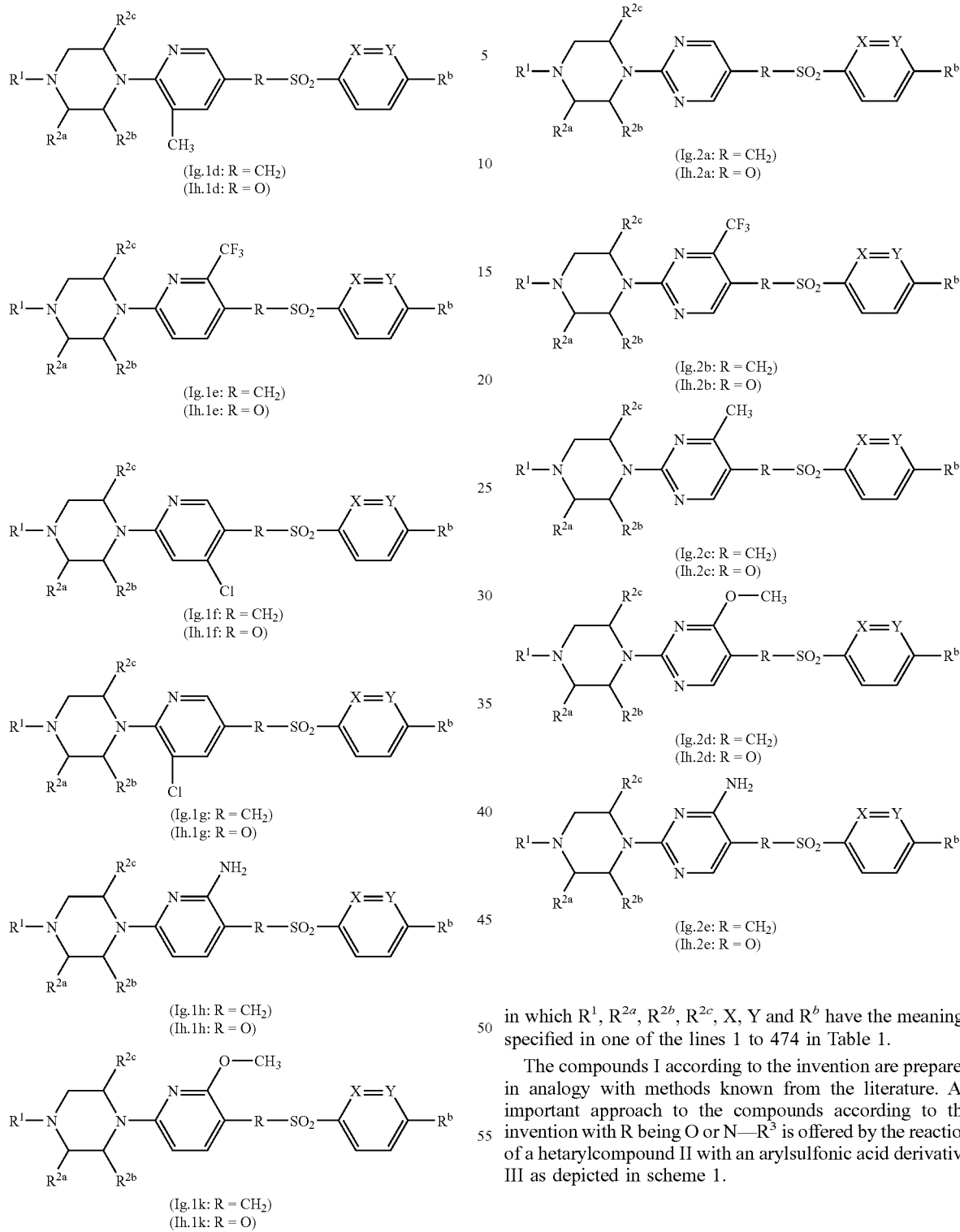

in which $R^1$, $R^{2a}$, $R^{2b}$, $R^{2c}$, X, Y and $R^b$ have the meanings specified in one of the lines 1 to 474 in Table 1.

Examples of compounds of the formula Ig.1 and Ih.1 are the compounds of the following general formulae Ig.2a, Ig.2b, Ig.2c, Ig.2d, Ig.2e, Ih.2a, Ih.2b, Ih.2c, Ih.2d and Ih.2e:

in which $R^1$, $R^{2a}$, $R^{2b}$, $R^{2c}$, X, Y and $R^b$ have the meanings specified in one of the lines 1 to 474 in Table 1.

The compounds I according to the invention are prepared in analogy with methods known from the literature. An important approach to the compounds according to the invention with R being O or N—$R^3$ is offered by the reaction of a hetarylcompound II with an arylsulfonic acid derivative III as depicted in scheme 1.

Scheme 1:

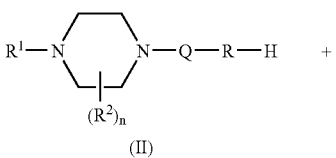

-continued

In scheme 1, n, $R^1$, $R^2$, $R^3$, Ar and Q have the previously mentioned meanings. R is O or N—$R^3$. X is a nucleophilically displaceable leaving group, in particular a halogen atom and, especially, chlorine or bromine. The reaction depicted in scheme 1 takes place under the reaction conditions which are customary for preparing arylsulfonamide compounds or arylsulfonic esters, respectively, and which are described, for example, in J. March, Advanced Organic Chemistry, $3^{rd}$ edition, John Wiley & Sons, New York, 1985 p 444 and the literature cited therein, European J. Org. Chem. 2002 (13), pp. 2094-2108, Tetrahedron 2001, 57 (27) pp. 5885-5895, Bioorganic and Medicinal Chemistry Letters, 2000, 10(8), pp. 835-838 and Synthesis 2000 (1), pp. 103-108.

The reaction customarily takes place in an inert solvent, for example in an ether, such as diethyl ether, diisopropyl ether, methyl tert-butyl ether or tetrahydrofuran, a halohydrocarbon, such as dichloromethane, an aliphatic or cycloaliphatic hydrocarbon, such as pentane, hexane or cyclohexane, or an aromatic hydrocarbon, such as toluene, xylene, cumene and the like, or in a mixture of the above-mentioned solvents.

The reaction of II with III is customarily carried out in the presence of an auxiliary base. Suitable bases are inorganic bases, such as sodiumcarbonate or potassiumcarbonate, or sodiumhydrogencarbonate or potassiumhydrogencarbonate, and organic bases, for example trialkylamines, such as triethylamine, or pyridine compounds, such as pyridine, lutidine and the like. The latter compounds can at the same time serve as solvents. The auxiliary base is customarily employed in at least equimolar quantities, based on the amine compound II.

The compounds of the general formula II are known per se or, in case R is N—$R^{3a}$, can be prepared in the manner shown in schemes 2.

Scheme 2:

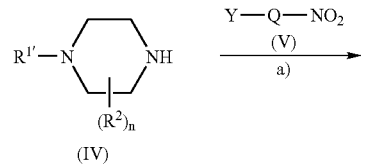

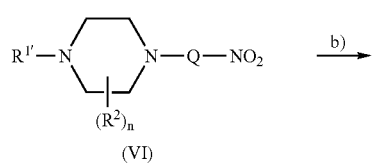

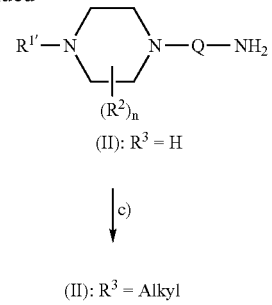

In scheme 2, n, $R^2$ and Q have the previously mentioned meanings. $R^{1'}$ has the meanings different from hydrogen which are specified for $R^1$ or is a suitable protecting group. Suitable protecting groups are disclosed, for example, in P. Kocienski, Protecting Groups, Thieme-Verlag, Stuttgart 2000, Chapter 6. Y is a nucleophilically displaceable leaving group, in particular a halogen atom, e.g. chlorine or bromine, or an alkylsulfonyl group, e.g. methylsulfonyl.

The reaction depicted in step a) in scheme 2 takes place under the reaction conditions which are customary for a nucleophilic substitution on an aromatic radical and which are described, for example, in Tetrahedron 1999, 55(33), pp.10243-10252, J. Med. Chem. 1997, 40(22), pp. 3679-3686 and Synthetic Communications, 1993, 23(5), pp. 591-599. Where appropriate, it can be advantageous to convert a ring nitrogen atom in the Q group into its N-oxide (see, for example, Angew. Chem. Int. Ed. Engl.,2002 41 (11), pp. 1937-1940, J. Med. Chem. 1985, 28(2), pp. 248-252 and Tetrahedron Lett. 2002 43(17) pp. 3121-3123). This approach has proved to be of value, in particular, for preparing compounds I in which Q is a pyridin-2,4-diyl group. In connection with the subsequent reduction of the nitro group in VI (step b), the N-oxide group is also reduced. For this, the reduction is carried out, for example, in the presence of indium salts.

If 5-bromonitropyridine is used as compound V in step a) in accordance with scheme 2, the coupling is also achieved under palladium catalysis in the presence of an auxiliary base, for example an alkali metal carbonate such as cesium carbonate. Particularly suitable palladium catalysts in this connection are palladium(0) compounds or palladium compounds which are able to form a palladium(0) compound under reaction conditions, e.g. palladium dichloride, tetrakis(triphenylphosphine)palladiu m(0), tris(dibenzylideneacetone)dipalladium(0), advantageously in combination with phosphine ligands, e.g. triarylphosphines, such as triphenylphosphine, trialkylphosphines, such as tributylphosphine, and cycloalkylphosphines, such as tricyclohexylphosphine, and, especially, using phosphine chelate ligands, such as 2,2'-bis(diphenylphosphino)-1,1'-binaphthyl. The conditions which are required for reactions of this nature are described, for example, in Tetrahedron Lett. 2001, 42(22), p. 3681 and Tetrahedron Lett. 2002, 43(12), pp. 2171-2173.

In step b), the nitro group in VI is reduced to the $NH_2$ group in II. Subsequently, in step c), the $NH_2$ group can be converted into a —$NR^{3'}$H group, in which $R^{3'}$ has the meanings different from hydrogen which are specified for $R^3$.

The reaction conditions which are required for step b) correspond to the customary conditions for reducing aromatic nitro groups which have been described extensively in the literature (see, for example, J. March, Advanced Organic Chemistry, 3rd ed., J. Wiley & Sons, New-York, 1985, p.1183 and the literature cited in this reference).

The reduction is achieved, for example, by reacting the nitro compound VII with a metal such as iron, zinc or tin under acidic reaction conditions, i.e. using nascent hydrogen, or using a complex hydride such as lithium aluminum hydride or sodium borohydride, preferably in the presence of transition metal compounds of nickel or cobalt such as $NiCl_2(P(phenyl)_3)_2$, or $CoCl_2$, (see Ono et al. Chem. Ind. (London), 1983 p.480), or using $NaBH_2S_3$ (see Lalancette et al. Can. J. Chem. 49, 1971, p. 2990), with it being possible to carry out these reductions, depending on the given reagent, in substance or in a solvent or diluent. Alternatively, the reduction of VI to II can be carried out with hydrogen in the presence of a transition metal catalyst, e.g. using hydrogen in the presence of catalysts based on platinum, palladium, nickel, ruthenium or rhodium. The catalysts can contain the transition metal in elemental form or in the form of a complex compound, of a salt or of an oxide of the transition metal, with it being possible, for the purpose of modifying the activity, to use customary coligands, e.g. organic phosphine compounds, such as triphenylphosphine, tricyclohexylphosphine or tri-n-butylphosphines or phosphites. The catalyst is customarily employed in quantities of from 0.001 to 1 mol per mol of compound VI, calculated as catalyst metal. In a preferred variant, the reduction is effected using tin(II) chloride in analogy with the methods described in Bioorganic and Medicinal Chemistry Letters, 2002, 12(15), pp. 1917-1919 and J. Med. Chem. 2002, 45(21), pp. 4679-4688. The reaction of VI with tin(II) chloride is preferably carried out in an inert organic solvent, preferably an alcohol such as methanol, ethanol, isopropanol or butanol.

Reducing VI results in compounds II in which $R^3$ is hydrogen. Customary methods can then be used to react these compounds with an alkylating agent $R^{3'}$—X, in which $R^{3'}$ is $C_1$-$C_4$-alkyl and X is a nucleophilically displaceable leaving group (e.g. halogen, such as chlorine, bromine or iodine), resulting in a compound II in which $R^3$=alkyl (step c). The reaction conditions which are required for this are disclosed, for example, in WO 02/83652, Tetrahedron 2000, 56(38) pp. 7553-7560 and Synlett. 2000 (4), pp. 475-480.

The compound I can also be prepared by the route depicted in scheme 3:

Scheme 3:

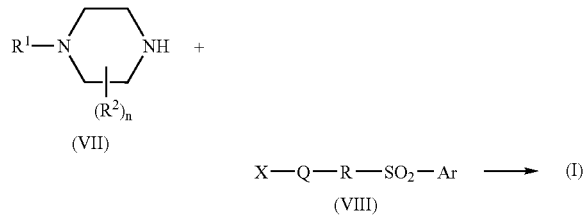

In scheme 3, n, R, $R^1$, $R^2$, Ar and Q have the previously mentioned meanings. Y is a nucleophilically displaceable leaving group, in particular a halogen atom, e.g. chlorine or bromine, or an alkylsulfonyl group, e.g. methylsulfonyl. The reaction of VII with VIII, as depicted in scheme 3, takes place under the reaction conditions specified for scheme 2, step a). Compounds of the general formulae VII and VIII are known or can be prepared in analogy with the methods known from the literature. Compounds or the formula VIII, wherein R is N—$R^3$ or an oxygen atom can be prepared by amidation of the the corresponding aminocompound X—Q—$NHR^3$ (or esterification of the corresponding hydroxycompound X—Q—OH) with a sulfonyl-halide, especiall with a sulfonylchloride of the formula Z—$SO_2$—Ar, wherein Z is halogen, especially chlorine or bromine, according to standard methods of organic chemistry (see e.g. J. March, Advanced Organic Chemistry, $3^{rd}$ edition, John Wiley & Sons, New York, 1985 p 444 and the literature cited therein).

Compounds of general formula I, in which $R^1$ is an allyl group, can be converted into compounds possessing different $R^1$ substituents using the synthetic route shown in scheme 4.

Scheme 4:

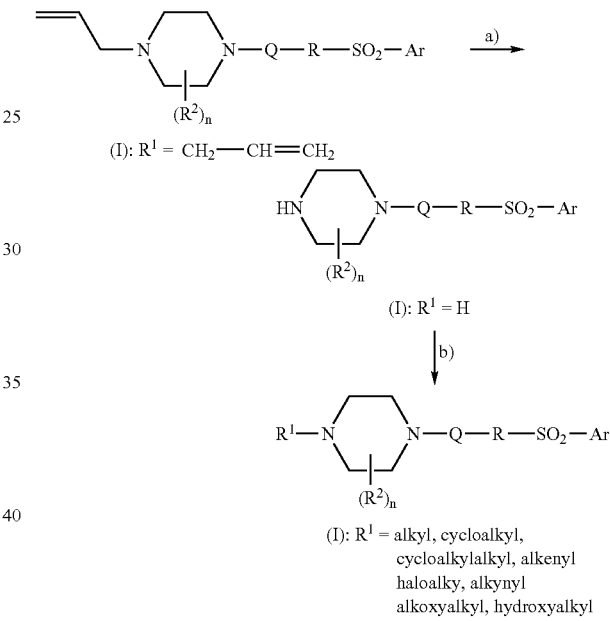

In scheme 4, n, R, $R^2$, Ar and Q have the previously mentioned meanings. The elimination of the allyl group, as depicted in step a) in scheme 4, is achieved, for example, by reacting I [$R^1$=allyl] with an allyl trapping agent, such as mercaptobenzoic acid or 1,3-dimethylbarbituric acid, in the presence of catalytic quantities of palladium (0) compounds or palladium compounds which are able to form a palladium (0) compound under reaction conditions, e.g. palladium dichloride, tetrakis(triphenylphosphine)palladium(0) or tris (dibenzylideneacetone)dipalladium(0), advantageously in combination with phosphine ligands, e.g. triarylphosphines, such as triphenylphosphine, trialkylphosphines, such as tributylphosphine, and cycloalkylphosphines, such as tricyclohexylphosphine, and especially with phosphine chelate ligands, such as 2,2'-bis(diphenylphosphino)-1,1'-binaphthyl or 1,4-bis(diphenylphosphino)butane, using methods known from the literature (with regard to eliminating N-allyl in the presence of mercaptobenzoic acid, see WO 94/24088; with regard to eliminating in the presence of 1,3-dimethylbarbituric acid, see J. Am. Chem. Soc. 2001, 123 (28), pp. 6801-6808 and J. Org. Chem 2002, 67(11) pp. 3718-3723). Alternatively, the elimination of N-allyl, as depicted in scheme 4 step a), can also be effected by reacting in the presence of rhodium compounds, such as tris(triphenylphosphine)chlororhodium(I), using methods known from the literature (see J. Chem. Soc., Perkin Transaction I: Organic and Bio-Organic Chemistry 1999 (21) pp. 3089-3104 and Tetrahedron Asymmetry 1997, 8(20), pp. 3387-3391).

The resulting piperazine compound I [$R^1$=H] can then be reacted, in a known manner, in the sense of an alkylation, with a compound $R^1$—X. In this compound, $R^1$ is $C_1$-$C_4$-alkyl, $C_3$-$C_6$-cycloalkyl, $C_1$-$C_4$-haloalkyl, $C_1$-$C_4$-alkoxy-$C_1$-$C_4$-alkyl or $C_3$-$C_6$-cycloalkyl-$C_1$-$C_4$-alkyl and X is a nucleophilically displaceable leaving group, e.g. halogen, trifluoroacetate, alkylsulfonate, arylsulfonate, alkyl sulfate and the like. The reaction conditions which are required for the alkylation in step b) have been adequately disclosed, e.g. in Bioorganic and Medicinal Chemistry Left. 2002, 12(7), pp. 2443-2446 and also 2002, 12(5), pp. 1917-1919.

The conversion, as depicted in scheme 4, step b), of the piperazine compound I [$R^1$=H] obtained in step a) can also be achieved, in the sense of a reductive amination, by reacting I [$R^1$=H] with a suitable ketone or aldehyde in the presence of a reducing agent, e.g. in the presence of a borohydride such as sodium borohydride, sodium cyanoborohydride or sodium triacetoxyborohydride. The skilled person is familiar with the reaction conditions which are required for a reductive amination, e.g. from Bioorganic and Medicinal Chemistry Left. 2002, 12(5), pp. 795-798 and 12(7) pp. 1269-1273.

The conversion, as depicted in scheme 4, step b), of the piperazine compound I [$R^1$=H] obtained in step a) can also be achieved by successive acylation and subsequent reduction of the acylation product, using the method depicted in scheme 4a:

Scheme 4a:

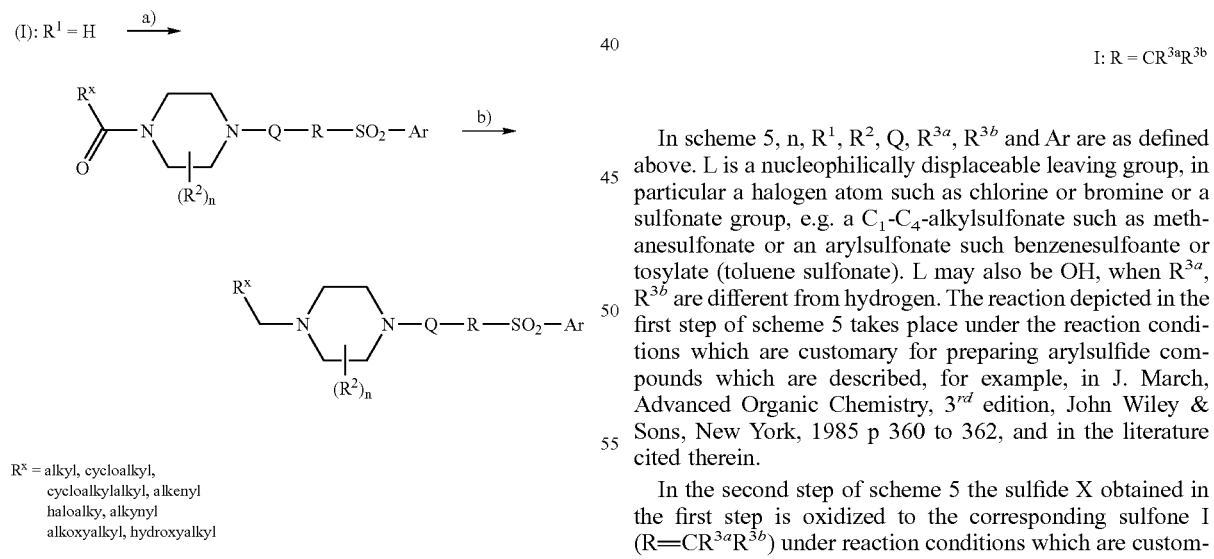

$R^x$ = alkyl, cycloalkyl,
cycloalkylalkyl, alkenyl
haloalky, alkynyl
alkoxyalkyl, hydroxyalkyl In scheme 4a, n, R, $R^2$, Ar and Q have the previously mentioned meanings. The acylation in step a) and the reduction in step b) are effected using standard methods of organic chemistry as are described, for example, in J. March, Advanced Organic Chemistry, 3rd ed. J. Wiley & Sons, New York 1985, p.370 and 373 (acylation) and p. 1099 f. and in the literature cited in this publication (with regard to acylation, see also Synth. Commun. 1986, 16, p. 267, and with regard to reduction, see also J. Heterocycl. Chem. 1979, 16, p. 1525).

In compounds of the general formula I which carry a halogen atom, in particular bromine or iodine, on the aromatic radical Ar, the halogen atom can be converted into an alkyl, alkenyl, cycloalkyl, alkynyl or cycloalkylalkyl group using methods which are known per se. The conversion is achieved by coupling the halo compound I to an alkyl-, alkenyl-, alkynyl-, cycloalkyl- or cycloalkylalkyl-boronic acid compound under the conditions of a Suzuki coupling as is described, for example, in Tetrahedron Lett. 2002, 43, pp. 6987-6990; Chem. Rev. 1995, 95, pp. 2457-2483 and J. Org. Chem. 66(21) (2001), pp. 7124-7128.

Compounds of the formula I, wherein R is $CR^{3a}R^{3b}$, can be also prepared by the synthetic route illustrated in scheme 5:

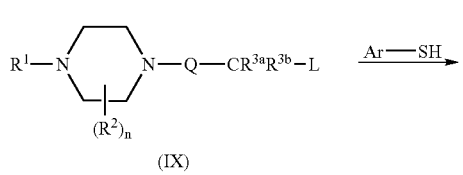

(IX)

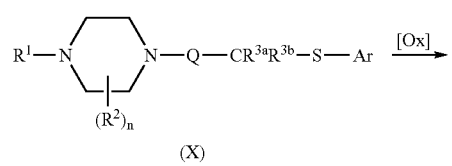

(X)

I: R = $CR^{3a}R^{3b}$

In scheme 5, n, $R^1$, $R^2$, Q, $R^{3a}$, $R^{3b}$ and Ar are as defined above. L is a nucleophilically displaceable leaving group, in particular a halogen atom such as chlorine or bromine or a sulfonate group, e.g. a $C_1$-$C_4$-alkylsulfonate such as methanesulfonate or an arylsulfonate such benzenesulfoante or tosylate (toluene sulfonate). L may also be OH, when $R^{3a}$, $R^{3b}$ are different from hydrogen. The reaction depicted in the first step of scheme 5 takes place under the reaction conditions which are customary for preparing arylsulfide compounds which are described, for example, in J. March, Advanced Organic Chemistry, $3^{rd}$ edition, John Wiley & Sons, New York, 1985 p 360 to 362, and in the literature cited therein.

In the second step of scheme 5 the sulfide X obtained in the first step is oxidized to the corresponding sulfone I (R=$CR^{3a}R^{3b}$) under reaction conditions which are customary for preparing arylsulfone compounds from the corresponding arylsulfides and which are described, for example, in J. March, Advanced Organic Chemistry, $3^{rd}$ edition, John Wiley & Sons, New York, 1985 p 1089 f. and in the literature cited therein.

The compounds of the formula IX are known in the art or can be prepared according to the method depicted in scheme 6:

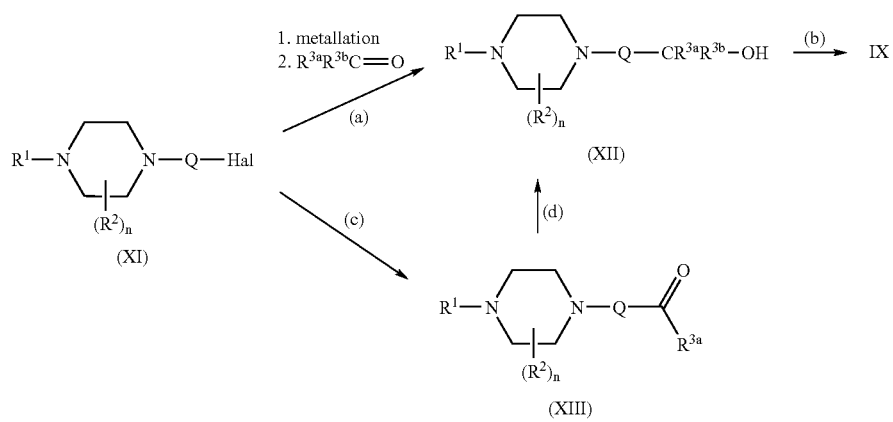

In scheme 6, n, $R^1$, $R^2$, Q, $R^{3a}$, $R^{3b}$ and Ar are as defined above. Hal is halogen, especially chlorine, bromine or iodine. In step (a) of scheme 6 the halogen compound XI is first metallized, i.e. converted into the corresponding lithium compound or magnesium compound by standard methods of organic chemistry and the thus obtained metal compound is reacted with an aldehyde or ketone to obtain the alcohol XII (see e.g. Tetrahedron 2003, 59 (24), 4303-4308). In step (b) he OH group of XII is then converted into a suitable leaving group, e.g. into a halogen atom by reaction with thionylhalide such as $SOCl_2$ or phosphorylhalide such as $POCl_3$, or into an alkylsulfonate or arylsulfonate by reaction with an alkylsulfonylhalide such as methanesulfonylchloride or with an arylsulfonylhalide such as toluoenesulfonylchloride (see e.g. J. Med. Chem. 1985, 28 (12), 1790-1796).

Alternatively the halogen compound XI is converted into the carbonyl compound XIII (step c, see e.g. J. Med. Chem. 1987, 30 (8), 1494-1497), which is then reduced ($R^{3b}$=H) or reacted with an alkylgrignard $R^{3b}$—Mg—X (X=halogen, e.g. Cl or Br) to obtain the alcohol XII (step (d), see e.g. J. Org. Chem. 2003, 68 (9), 3736-3738).

If not otherwise indicated, the above-described reactions are generally carried out in a solvent at temperatures between room temperature and the boiling temperature of the solvent employed. Alternatively, the activation energy which is required for the reaction can be introduced into the reaction mixture using microwaves, something which has proved to be of value, in particular, in the case of the reactions catalyzed by transition metals (with regard to reactions using microwaves, see Tetrahedron 2001, 57, p. 9199 ff. p. 9225 ff. and also, in a general manner, "Microwaves in Organic Synthesis", André Loupy (Ed.), Wiley-VCH 2002.

Examples of solvents which can be used are ethers, such as diethyl ether, diisopropyl ether, methyl tert-butyl ether or tetrahydrofuran, aprotic polar solvent, such as dimethylformamide, dimethyl sulfoxide, dimethoxyethane, and acetonitrile, aromatic hydrocarbons, such as toluene and xylene, ketones, such as acetone or methyl ethyl ketone, halohydrocarbons, such as dichloromethane, trichloromethane and dichloroethane, esters, such as ethyl acetate and methyl butyrate, carboxylic acids, such as acetic acid or propionic acid, and alcohols, such as methanol, ethanol, n-propanol, isopropanol and butanol.

If desired, it is possible for a base to be present in order to neutralize protons which are released in the reactions. Suitable bases include inorganic bases, such as sodium carbonate, potassium carbonate, sodium hydrogen carbonate or potassium hydrogen carbonate, and, in addition, alkoxides, such as sodium methoxide or sodium ethoxide, alkali metal hydrides, such as sodium hydride, and also organometallic compounds, such as butyllithium compounds or alkylmagnesium compounds, or organic nitrogen bases, such as triethylamine or pyridine. The latter compounds can at the same time serve as solvents.

The crude product is isolated in a customary manner, for example by filtering, distilling off the solvent or extracting from the reaction mixture, etc. The resulting compounds can be purified in a customary manner, for example by means of recrystallizing from a solvent, by means of chromatography or by means of converting into an acid addition salt.

The acid addition salts are prepared in a customary manner by mixing the free base with a corresponding acid, where appropriate in solution in an organic solvent, for example a lower alcohol, such as methanol, ethanol or propanol, an ether, such as methyl tert-butyl ether or diisopropyl ether, a ketone, such as acetone or methyl ethyl ketone, or an ester, such as ethyl acetate.

The compounds according to the invention of the formula I are highly selective dopamine $D_3$ receptor ligands which, because of their low affinity for other receptors such as $D_1$ receptors, $D_4$ receptors, α1-adrenergic and/or α2-adrenergic receptors, muscarinergic receptors, histamine receptors, opiate receptors and, in particular, dopamine $D_2$ receptors, give rise to fewer side-effects than do the classic neuroleptics, which are $D_2$ receptor antagonists.

The high affinity of the compounds according to the invention for $D_3$ receptors is reflected in very low in-vitro $K_i$ values of as a rule less than 100 nM (nmol/l), in particular less than 50 nM and, in particular, of less than 10 nM. The displacement of $[^{125}I]$-iodosulpride can, for example, be used in receptor binding studies for determining binding affinities for $D_3$ receptors.

The selectivity $K_i(D_2)/K_i(D_3)$ of the compounds according to the invention is as a rule at least 10, preferably at least 30, even better at least 50 and particularly advantageously at least 100. The displacement of $[^3H]SCH23390$, $[^{125}I]$ iodosulpride or $[^{125}I]$ spiperone can be used, for example, for carrying out receptor binding studies on $D_1$, $D_2$ and $D_4$ receptors.

Because of their binding profile, the compounds can be used for treating diseases which respond to dopamine $D_3$ ligands, i.e. they are effective for treating those disturbances or diseases in which exerting an influence on (modulating)

the dopamine $D_3$ receptors leads to an improvement in the clinical picture or to the disease being cured. Examples of these diseases are disturbances or diseases of the central nervous system.

Disturbances or diseases of the central nervous system are understood as meaning disturbances which affect the spinal chord and, in particular, the brain. Within the meaning of the invention, the term "disturbance" denotes anomalies which are as a rule regarded as being pathological conditions or functions and which can manifest themselves in the form of particular signs, symptoms and/or malfunctions. While the treatment according to the invention can be directed toward individual disturbances, i.e. anomalies or pathological conditions, it is also possible for several anomalies, which may be causatively linked to each other, to be combined into patterns i.e. syndromes, which can be treated in accordance with the invention.

The disturbances which can be treated in accordance with the invention are, in particular, psychiatric and neurological disturbances. These disturbances include, in particular, organic disturbances, including symptomatic disturbances, such as psychoses of the acute exogenous reaction type or attendant psychoses of organic or exogenous cause, e.g., in association with metabolic disturbances, infections and endocrinopathogies; endogenous psychoses, such as schizophrenia and schizotype and delusional disturbances; affective disturbances, such as depressions, mania and/or manic-depressive conditions; and also mixed forms of the above-described disturbances; neurotic and somatoform disturbances and also disturbances in association with stress; dissociative disturbances, e.g. loss of consciousness, clouding of consciousness, double consciousness and personality disturbances; disturbances in attention and waking/sleeping behavior, such as behavioral disturbances and emotional disturbances whose onset lies in childhood and youth, e.g. hyperactivity in children, intellectual deficits, in particular attention disturbances (attention deficit disorders), memory disturbances and cognitive disturbances, e.g. impaired learning and memory (impaired cognitive function), dementia, narcolepsy and sleep disturbances, e.g. restless legs syndrome; development disturbances; anxiety states, delirium; sexlife disturbances, e.g. impotence in men; eating disturbances, e.g. anorexia or bulimia; addiction; and other unspecified psychiatric disturbances.

The disturbances which can be treated in accordance with the invention also include Parkinson's disease and epilepsy and, in particular, the affective disturbances connected thereto.

The addiction diseases include psychic disturbances and behavioral disturbances which are caused by the abuse of psychotropic substances, such as pharmaceuticals or narcotics, and also other addiction diseases, such as addiction to gaming (impulse control disorders not elsewhere classified). Examples of addictive substances are: opioids (e.g. morphine, heroin and codeine), cocaine; nicotine; alcohol; substances which interact with the GABA chloride channel complex, sedatives, hypnotics and tranquilizers, for example benzodiazepines; LSD; cannabinoids; psychomotor stimulants, such as 3,4-methylenedioxy-N-methylamphetamine (ecstasy); amphetamine and amphetamine-like substances such as methylphenidate and other stimulants including caffeine. Addictive substances which come particularly into consideration are opioids, cocaine, amphetamine or amphetamine-like substances, nicotine and alcohol.

With regard to the treatment of addiction diseases, particular preference is given to those compounds according to the invention of the formula I which themselves do not possess any psychotropic effect. This can also be observed in a test using rats, which, after having been administered compounds which can be used in accordance with the invention, reduce their self administration of psychotropic substances, for example cocaine.

According to another aspect of the present invention, the compounds according to the invention are suitable for treating disturbances whose causes can at least partially be attributed to an anomalous activity of dopamine $D_3$ receptors.

According to another aspect of the present invention, the treatment is directed, in particular, toward those disturbances which can be influenced, within the sense of an expedient medicinal treatment, by the binding of preferably exogeneously administered binding partners (ligands) to dopa mine $D_3$ receptors.

The diseases which can be treated with the compounds according to the invention are frequently characterized by progressive development, i.e. the above-described conditions change over the course of time; as a rule, the severity increases and conditions may possibly merge into each other or other conditions may appear in addition to those which already exist.

The compounds according to the invention can be used to treat a large number of signs, symptoms and/or malfunctions which are connected with the disturbances of the central nervous system and, in particular, the abovementioned conditions. These signs, symptoms and/or malfunctions include, for example, a disturbed relationship to reality, lack of insight and ability to meet customary social norms or the demands made by life, changes in temperament, changes in individual drives, such as hunger, sleep, thirst, etc., and in mood, disturbances in the ability to observe and combine, changes in personality, in particular emotional lability, hallucinations, ego-disturbances, distractedness, ambivalence, autism, depersonalization and false perceptions, delusional ideas, chanting speech, lack of synkinesia, short-step gait, flexed posture of trunk and limbs, tremor, poverty of facial expression, monotonous speech, depressions, apathy, impeded spontaneity and decisiveness, impoverished association ability, anxiety, nervous agitation, stammering, social phobia, panic disturbances, withdrawal symptoms in association with dependency, maniform syndromes, states of excitation and confusion, dysphoria, dyskinetic syndromes and tic disturbances, e.g. Huntington's chorea and Gilles-de-la-Tourette's syndrome, vertigo syndromes, e.g. peripheral positional, rotational and oscillatory vertigo, melancholia, hysteria, hypochondria and the like.

Within the meaning of the invention, a treatment also includes a preventive treatment (prophylaxis), in particular as relapse prophylaxis or phase prophylaxis, as well as the treatment of acute or chronic signs, symptoms and/or malfunctions. The treatment can be orientated symptomatically, for example as the suppression of symptoms. It can be effected over a short period, be orientated over the medium term or can be a long-term treatment, for example within the context of a maintenance therapy.

The compounds according to the invention are preferentially suitable for treating diseases of the central nervous system, in particular for treating affective disturbances; neurotic disturbances, stress disturbances and somatoform disturbances and psychoses, and, in particular, for treating schizophrenia and depression. Because of their high selectivity with regard to the $D_3$ receptor, the compounds I according to the invention are also suitable for treating disturbances of kidney function, in particular disturbances of kidney function which are caused by diabetes mellitus (see WO 00/67847) and, especially, diabetic nephropathy.

Within the context of the treatment, the use according to the invention of the described compounds involves a method. In this method, an effective quantity of one or more compounds, as a rule formulated in accordance with pharmaceutical and veterinary practice, is administered to the individual to be treated, preferably a mammal, in particular a human being, productive animal or domestic animal. Whether such a treatment is indicated, and in which form it is to take place, depends on the individual case and is subject to medical assessment (diagnosis) which takes into consideration signs, symptoms and/or malfunctions which are present, the risks of developing particular signs, symptoms and/or malfunctions, and other factors.

As a rule, the treatment is effected by means of single or repeated daily administration, where appropriate together, or alternating, with other active compounds or active compound-containing preparations such that a daily dose of preferably from about 0.1 to 1000 mg/kg of bodyweight, in the case of oral administration, or of from about 0.1 to 100 mg/kg of bodyweight, in the case of parenteral administration, is supplied to an individual to be treated.

The invention also relates to the production of pharmaceutical compositions for treating an individual, preferably a mammal, in particular a human being, productive animal or domestic animal. Thus, the ligands are customarily administered in the form of pharmaceutical compositions which comprise a pharmaceutically acceptable excipient together with at least one ligand according to the invention and, where appropriate, other active compounds. These compositions can, for example, be administered orally, rectally, transdermally, subcutaneously, intravenously, intramuscularly or intranasally.

Examples of suitable pharmaceutical formulations are solid medicinal forms, such as powders, granules, tablets, in particular film tablets, lozenges, sachets, cachets, sugar-coated tablets, capsules, such as hard gelatin capsules and soft gelatin capsules, suppositories or vaginal medicinal forms, semisolid medicinal forms, such as ointments, creams, hydrogels, pastes or plasters, and also liquid medicinal forms, such as solutions, emulsions, in particular oil-in-water emulsions, suspensions, for example lotions, injection preparations and infusion preparations, and eyedrops and eardrops. Implanted release devices can also be used for administering inhibitors according to the invention. In addition, it is also possible to use liposomes or microspheres.

When producing the compositions, inhibitors according to the invention are usually mixed or diluted with an excipient. Excipients can be solid, semisolid or liquid materials which serve as vehicles, carriers or medium for the active compound.

Suitable excipients are listed in the specialist medicinal monographs. In addition, the formulations can comprise pharmaceutically acceptable carriers or customary auxiliary substances, such as glidants; wetting agents; emulsifying and suspending agents; preservatives; antioxidants; antiirritants; chelating agents; coating auxiliaries; emulsion stabilizers; film formers; gel formers; odor masking agents; taste corrigents; resin; hydrocolloids; solvents; solubilizers; neutralizing agents; diffusion accelerators; pigments; quaternary ammonium compounds; refatting and overfatting agents; raw materials for ointments, creams or oils; silicone derivatives; spreading auxiliaries; stabilizers; sterilants; suppository bases; tablet auxiliaries, such as binders, fillers, glidants, disintegrants or coatings; propellants; drying agents; opacifiers; thickeners; waxes; plasticizers and white mineral oils. A formulation in this regard is based on specialist knowledge as described, for example, in Fiedler, H. P., Lexikon der Hilfsstoffe für Pharmazie, Kosmetik und angrenzende Gebiete [Encyclopedia of auxiliary substances for pharmacy, cosmetics and related fields], $4^{th}$ edition, Aulendorf: ECV-Editio-Kantor-Verlag, 1996.

The following examples serve to explain the invention without limiting it.

The magnetic nuclear resonance spectral properties (NMR) refer to the chemical shifts (δ) expressed in parts per million (ppm). The relative area of the shifts in the $^1$H NMR spectrum corresponds to the number of hydrogen atoms for a particular functional type in the molecule. The nature of the shift, as regards multiplicity, is indicated as singlet (s), broad singlet (s. br.), doublet (d), broad doublet (d br.), triplet (t), broad triplet (t br.), quartet (q), quintet (quint.) and multiplet (m).

PREPARATION EXAMPLES

Example 1

N-[6-(4-Allylpiperazin-1-yl)pyridin-3-yl]-4-isopropylbenzenesulfonamide 1.1 1-Allyl-4-(5-nitropyridin-2-yl)piperazine 2.0 g (12.61 mmol) of 2-chloro-5-nitropyridine were dissolved in 8 ml of dimethylformamide, and 3.49 g (25.23 mmol) of potassium carbonate were added. After that, a solution of 1.75 g (13.88 mmol) of N-allylpiperazine in 2 ml of dimethylformamide was added slowly dropwise to the reaction mixture (exothermic reaction). The reaction mixture was then stirred at room temperature for 2 hours. After the solvent had been concentrated down to dryness, the resulting residue was stirred up in 100 ml of heptane. The precipitate which remained was filtered off with suction. The filtrate was concentrated, resulting in 720 mg of the title compound. The precipitate which had been filtered off with suction was treated with 150 ml of water and extracted three times with diethyl ether. The organic phase was washed with a saturated solution of sodium chloride and dried over sodium sulfate. A further 2.24 g of the title compound were isolated after the solvent had been filtered and concentrated down to dryness. The total yield of 1-allyl-4-(5-nitropyridin-2-yl)piperazine was 2.96 g (95% of theory).

MS [m+1]: 249.

1.2 6-(4-Allylpiperazin-1-yl)pyridine-3-amine 2.2 g (8.86 mmol) of 1-allyl-4-(5-nitropyridin-2-yl)piperazine from Example 1.1 were dissolved in 150 ml of methanol after which 18 g (79.75 mmol) of tin(II) chloride dihydrate were added and the mixture was stirred at 70° C. for 4 hours. After the solvent had been evaporated down to dryness, water was added to the residue. The aqueous reaction mixture was made alkaline with dilute sodium hydroxide solution and then extracted with ethyl acetate. The solid which had precipitated out was filtered off. After that, the phases were separated and the aqueous phase was extracted in each case twice with ethyl acetate and dichloromethane. The combined organic phases were dried over sodium sulfate. 1.74 g (90% of theory) of the title compound were obtained after the drying agent had been removed and the solvent had been evaporated down to dryness.

MS [m+1]: 219.

1.3 N-[6-(4-Allylpiperazin-1-yl)pyridin-3-yl]-4-isopropyl-benzenesulfonamide 1.4 g (7.97 mmol) of 6-(4-allylpiperazin-1-yl)pyridin-3-ylamine from Example 1.2 and 1.74 g (7.97 mmol) of 4-isopropylbenzenesulfonyl chloride were dissolved in 30 ml of tetrahydrofuran at room temperature. 3.3 ml (23.91 mmol) of triethylamine were then added to this mixture. After that, the reaction mixture was stirred overnight at room temperature. After the solvent had been evaporated to dryness, water was added to the residue. The aqueous reaction mixture was made acid with 1N hydrochloric acid and extracted twice with diethyl ether. After that, the aqueous phase was made alkaline (pH 9-10) with a 1N aqueous solution of sodium hydroxide and then extracted twice with diethyl ether. After the combined organic phases had been dried over sodium sulfate, the drying agent had been filtered off and the solvent had been evaporated down to dryness, the resulting residue was chromatographed on silica gel using cyclohexane/ethyl acetate (45:55% to 100% ethyl acetate). The filtrate was evaporated down to dryness. The resulting residue was thoroughly stirred in 10 ml of heptane, filtered off in suction and dried, with 1.93 g (61% of theory) of the title compound being obtained.

$^1$H-NMR (500 MHz, CDCl$_3$): δ [ppm] 7.7 (s, 1H); 7.6 (d, 2H); 7.4 (d, 1H); 7.3 (d, 2H); 6.6 (d, 1H); 6.4 (bs, 1H); 5.9 (m, 1H); 5.2 (m, 2H); 3.5 (m, 4H); 3.1 (m, 2H); 3.0 (m, 1H); 2.5 (m, 4H); 1.2 (d, 6H).

MS [m+1]: 401.

Example 2

N-[6-(4-Allylpiperazin-1-yl)pyridin-3-yl]-4-propyl-benzenesulfonamide 373 mg of the title compound were obtained in an analogous manner to that described in Example 1.3 when starting with 4-n-propylbenzenesulfonyl chloride.

$^1$H-NMR (500 MHz, CDCl$_3$): δ [ppm] 7.7 (m, 1H); 7.6 (m, 2H); 7.4 (d, 1H); 7.3 (m, 2H); 6.6 (d, 1H); 6.3 (bs, 1H); 5.9 (m, 1H); 5.2 (m, 2H); 3.5 (m, 4H); 3.1 (m, 2H); 2.6 (m, 2H); 2.5 (m, 4H); 1.7 (m, 2H); 0.9 (m, 3H).

MS [m+1]: 401.

Example 3

N-[6-(4-Allylpiperazin-1-yl)pyridin-3-yl]-4-butyl-benzenesulfonamide 405 mg of the title compound were obtained in an analogous manner to that described in Example 1.3 when starting with 4-n-butylbenzenesulfonyl chloride.

$^1$H-NMR (500 MHz, CDCl$_3$): δ [ppm] 7.7 (m, 1H); 7.6 (m, 2H); 7.4 (d, 1H); 7.3 (m, 2H); 6.6 (d, 1H); 6.2 (bs, 1H); 5.9 (m, 1H); 5.2 (m, 2H); 3.5 (m, 4H); 3.0 (m, 2H); 2.7 (m, 2H); 2.5 (m, 4H); 1.6 (m, 2H); 1.4 (m, 2H); 0.9 (m, 3H).

MS [m+1]: 415.

Example 4

N-[6-(4-Allylpiperazin-1-yl)pyridin-3-yl]-4-trifluoromethylbenzenesulfonamide 500 mg of the title compound were obtained in an analogous manner to that described in Example 1.3 when starting with 4-trifluoromethylbenzenesulfonyl chloride.

$^1$H-NMR (500 MHz, CDCl$_3$): δ [ppm] 7.9 (d, 2H); 7.8 (m, 3H); 7.3 (d, 1H); 6.6 (d, 1H); 5.9 (m, 1H); 5.2 (m, 2H); 3.5 (m, 4H); 3.1 (m, 2H); 2.5 (m, 4H).

MS [m+1]: 427.

Example 5

N-[6-(4-Allylpiperazin-1-yl)pyridin-3-yl]-4-ethyl-benzenesulfonamide hydrochloride The Example 1.3 was repeated with 4-ethylbenzenesulfonyl chloride being used instead of 4-isopropylbenzenesulfonyl chloride. The resulting reaction product was converted into the hydrochloride with ethereal hydrochloric acid, with 480 mg (please complete) of the title compound being obtained.

$^1$H-NMR (400 MHz, DMSO-d$_6$): δ [ppm] 11.5 (bs, 1H); 10.0 (s, 1H); 7.8 (d, 2H); 7.6 (d, 2H); 7.4 (m, 3H); 6.9 (d, 1H); 6.0 (m, 1H); 5.5 (m, 2H); 4.3 (m, 2H); 3.8 (m, 2H); 3.4 (m, 2H); 3.3 (m, 2H); 3.0 (m, 2H); 2.7 (m, 2H); 1.2 (t, 3H).

MS [m+1]: 387 (free base).

Example 6

N-[6-(4-Allylpiperazin-1-yl)pyridin-3-yl]-4-vinyl-benzenesulfonamide hydrochloride Example 1.3 was repeated with 4-vinylbenzenesulfonyl chloride being used instead of 4-isopropylbenzenesulfonyl chloride. The resulting reaction product was converted into the hydrochloride with ethereal hydrochloric acid, with 300 mg of the title compound being obtained.

$^1$H-NMR (400 MHz, DMSO-d$_6$): δ [ppm] 11.1 (bs, 1H); 10.0 (s, 1H); 7.8 (d, 1H); 7.6 (m, 4H); 7.3 (d, 1H); 6.9 (d, 1H); 6.8 (dd, 1H); 6.0 (m, 2H); 5.5 (m, 3H); 4.3 (m, 2H); 3.8 (m, 2H); 3.4 (m, 2H); 3.2 (m, 2H); 3.0 (m, 2H).

MS [m+1]: 385 (free base).

Example 7

4-Isopropyl-N-(6-piperazin-1-ylpyridin-3-yl)benzenesulfonamide 95 mg (0.1 mmol) of tris-(dibenzylideneacetone)dipalladium(0) and 44 mg (0.1 mmol) of 1,4-bis-(diphenylphosphino)butane were dissolved in 10 ml of tetrahydrofuran under an argon atmosphere. A solution composed of 1.1 g (2.75 mmol) of N-[6-(4-allylpiperazin-1-yl)pyridin-3-yl]-4-isopropylbenzenesulfonamide from Example 1.3I in 3 ml of tetrahydrofuran was then added dropwise to the reaction mixture. After that, a solution of 386 mg (2.5 mmol) of 2-mercaptobenzoic acid in 2 ml of tetrahydrofuran was added dropwise to the reaction mixture and the mixture was stirred at room temperature for 90 minutes. A solution of a further 386 mg (2.5 mmol) of 2-mercaptobenzoic acid in 2 ml of tetrahydrofuran was then added dropwise to the reaction mixture. The reaction mixture was stirred overnight at room temperature and, after that, the solvent was evaporated down to dryness. 150 ml of water were added to the resulting residue, after which the mixture was made acid with 1N aqueous hydrochloric acid and extracted three times with diethyl ether. The aqueous phase was then made alkaline, to pH>11, with a 1N aqueous solution of sodium hydroxide and subsequently extracted three times with dichloromethane. After that, the aqueous phase was adjusted to pH 8-9, saturated with an aqueous solution of sodium chloride and, after that, extracted several times with dichloromethane. 840 mg (82% of theory) of the title compound were obtained after the combined organic phases had been dried over sodium sulfate and the solvent had been filtered and evaporated down to dryness.

$^1$H-NMR (400 MHz, CDCl$_3$): δ [ppm] 7.7 (d, 1H); 7.6 (d, 2H); 7.4 (dd, 1H); 7.3 (d, 2H); 6.6 (d, 1H); 3.5 (m, 4H); 3.0 (m, 5H); 1.2 (d, 6H).

MS [m+1]: 361.

Example 8

N-{6-[4-(Cyclohexylmethyl)piperazin-1-yl]pyridin-3-yl}-4-isopropyl-benzenesulfonamide hydrochloride 150 mg (0.42 mmol) of 4-isopropyl-N-(6-piperazin-1-yl-pyridin-3-yl)-benzenesulfonamide from Example 7 and 51 mg (0.46 mmol) of cyclohexanealdehyde were dissolved in 5 ml of dichloromethane and 40 µl (0.62 mmol) of glacial acetic acid under a nitrogen atmosphere. 133 mg (0.63 mmol) of sodium trisacetoxyborohydride were then added. The mixture was stirred at room temperature for 90 minutes and, after that, the solvent was evaporated down to dryness. The resulting residue was taken up in water and this mixture was made to pH>11 with a 1N aqueous solution of sodium hydroxide. After that, the aqueous reaction mixture was extracted with diethyl ether. After the organic phase had been dried over sodium sulfate and the solvent had been filtered and evaporated down to dryness, the resulting residue was converted into the hydrochloride with ethereal hydrochloric acid, resulting in 156 mg (76% of theory) of the title compound.

$^1$H-NMR (500 MHz, DMSO-d$_6$): δ [ppm] 10.4 (bs, 1H); 10.0 (s, 1H); 7.8 (d, 1H); 7.6 (d, 2H); 7.4 (d, 2H); 7.3 (d, 1H); 6.9 (d, 1H); 4.2 (m, 2H); 3.5 (m, 2H); 3.4 (m, 2H); 3.0 (m, 5H); 1.8 (m, 3H); 1.7 (m, 3H); 1.2 (m, 9H); 1.0 (m, 2H).

MS [m+1]: 457 (free base).

The compounds of Examples 9 to 12 were prepared in an analogous manner.

Example 9

N-[6-(4-Isobutylpiperazin-1-yl)pyridin-3-yl]-4-isopropylbenzenesulfonamide hydrochloride $^1$H-NMR (500 MHz, DMSO-d$_6$): δ [ppm] 10.4 (bs, 1H); 10.0 (s, 1H); 7.8 (m, 1H); 7.6 (d, 2H); 7.5 (d, 2H); 7.4 (m, 1H); 6.9 (d, 1H); 4.2 (d, 2H); 3.5 (d, 2H); 3.4 (m, 2H); 3.0 (m, 5H); 2.1 (m, 1H); 1.2 (d, 6H); 1.0 (d, 6H).

MS [m+1]: 417 (free base).

Example 10

4-Isopropyl-N-[6-(4-methylpiperazin-1-yl)pyridin-3-yl]benzenesulfonamide $^1$H-NMR (500 MHz, CDCl$_3$): δ [ppm] 7.7 (d, 1H); 7.6 (d, 2H); 7.4 (dd, 1H); 7.3 (d, 2H);

6.6 (d, 1H); 3.5 (m, 4H); 3.0 (m, 1H); 2.5 (m, 4H); 2.3 (s, 3H); 1.2 (d, 6H).

MS [m+1]: 375.

Example 11

N-[6-(4-Ethylpiperazin-1-yl)pyridin-3-yl]-4-isopropylbenzenesulfonamide hydrochloride $^1$H-NMR (500 MHz, DMSO-d$_6$): δ [ppm] 10.4 (bs, 1H); 10.0 (s, 1H); 7.8 (d, 1H); 7.6 (d, 2H); 7.4 (d, 2H); 7.3 (d, 1H); 6.9 (d, 1H); 4.3 (m, 2H); 3.5 (m, 2H); 3.2 (m, 2H); 3.1 (m, 2H); 3.0 (m, 3H); 1.3 (m, 3H); 1.2 (d, 6H).

MS [m+1]: 389 (free base).

Example 12

N-{6-[4-(Cyclopropylmethyl)piperazin-1-yl]pyridin-3-yl}-4-isopropylbenzenesulfonamide hydrochloride $^1$H-NMR (500 MHz, DMSO-d$_6$): δ [ppm] 10.8 (bs, 1H); 10.0 (s, 1H); 7.8 (d, 1H); 7.6 (d, 2H); 7.4 (d, 2H); 7.3 (d, 1H); 6.9 (d, 1H); 4.3 (m, 2H); 3.6 (m, 2H); 3.3 (m, 2H); 3.0 (m, 5H); 1.2 (d, 6H); 1.1 (m, 1H); 0.6 (m, 2H); 0.4 (m, 2H).

MS [m+1]: 415 (free base)

Example 13

N-[6-(4-Allyl-3-methylpiperazin-1-yl)pyridin-3-yl]-4-isopropylbenzenesulfonamide hydrochloride 13.1 3-Methyl-1-(5-nitropyridin-2-yl)piperazine 872 mg (6.31 mmol) of potassium carbonate were added to a solution of 500 mg (3.15 mmol) of 2-chloro-5-nitropyridine in 7 ml of dimethylformamide. After that, a solution of 350 mg (3.32 mmol) of 2-methylpiperazine in 3 ml of dimethylformamide was slowly added dropwise to the reaction mixture while cooling with ice (exothermic reaction). The reaction mixture was stirred for 1 hour while cooling with ice and then stirred overnight at room temperature. After the solvent had been evaporated to dryness, the residue was taken up in water and this mixture was extracted three times with diethyl ether. The combined organic phases were dried over sodium sulfate, filtered and evaporated to dryness, with 3-methyl-1-(5-nitropyridin-2-yl)piperazine (Yield: 650 mg, 89% of theory) being obtained.

$^1$H-NMR (500 MHz, CDCl$_3$): δ [ppm] 9.0 (s, 1H); 8.2 (d, 1H); 6.6 (d, 1H); 4.4 (m, 2H); 3.2 (m, 1H); 3.1 (m, 1H); 2.9 (m, 2H); 2.7 (m, 1H); 1.2 (m, 3H).

$^{13}$C-NMR (125 MHz, CDCl$_3$): 160.4 (C); 146.5 (CH); 134.9 (C); 133.0 (C); 104.5 (CH); 52.2 (CH$_2$); 50.6 (CH); 45.7 (CH$_2$); 45.4 (CH$_2$); 19.6 (CH$_3$).

13.2 1-Allyl-2-methyl-4-(5-nitropyridin-2-yl)piperazine 630 mg (2.72 mmol) of 3-methyl-1-(5-nitropyridin-2-yl)piperazine from Example 13.1 and 267 µl (3.09 mmol) of allyl bromide were dissolved in 10 ml of dimethylformamide. 1.2 ml (8.4 mmol) of triethylamine were then added dropwise to the solution. After the mixture had been stirred at room temperature for 1 hour, a further 65 µl (0.75 mmol) of allyl bromide were added dropwise to the reaction mixture, which was then stirred for a further hour. After that, a further 65 µl (0.75 mmol) of allyl bromide and 0.5 ml (3.6 mmol) of triethylamine were added dropwise. The mixture was then stirred overnight at room temperature. After the solvent had been evaporated down to dryness, the resulting residue was taken up in water and this solution was made alkaline using a 1N aqueous solution of sodium hydroxide. After that, the aqueous reaction mixture was extracted three times with diethyl ether. The combined organic phases were dried over sodium sulfate, filtered and evaporated down to dryness, with 707 mg (90% of theory) of the title compound being obtained.

MS [m+1]: 263.

13.3 6-(4-Allyl-3-methylpiperazin-1-yl)pyridine-3-amine 4.975 g (22.05 mmol) of tin(II) chloride dihydrate were added to a solution of 707 mg (2.45 mmol) of 1-allyl-2-methyl-4-(5-nitropyridin-2-yl)piperazine from Example 13.2 in 50 ml of methanol and the resulting mixture was stirred at 70° C. for 90 minutes. After the solvent had been evaporated down to dryness, water was added to the resulting residue and the mixture was made alkaline using a dilute aqueous solution of sodium hydroxide. After that, the aqueous reaction mixture was extracted with ethyl acetate. The solid which had precipitated out was filtered off with suction and the phases were separated. The aqueous phase was extracted with dichloromethane. After that, the combined organic phases were dried over sodium sulfate, filtered and evaporated down to dryness. The resulting title compound was used in the next step without any further purification.

MS [m+1]: 233.

13.4 N-[6-(4-Allyl-3-methylpiperazin-1-yl)pyridin-3-yl]-4-isopropylbenzenesulfonamide hydrochloride 305 mg (1.31 mmol) of 6-(4-allyl-3-methylpiperazin-1-yl)pyridin-3-ylamine from Example 13.3 and 301 mg (1.38 mmol) of 4-isopropylbenzenesulfonyl chloride were dissolved in 10 ml of tetrahydrofuran at room temperature, after which 0.55 ml (3.94 mmol) of triethylamine was added dropwise. After that, the reaction mixture was stirred overnight at room temperature. After the solvent had been evaporated down to dryness, the resulting residue was treated with water and the mixture was made acid with 1N hydrochloric acid and extracted twice with diethylether. The aqueous phase was made alkaline, to pH 9-10, using a 1N aqueous solution of sodium hydroxide and then extracted twice with diethyl ether. After the combined organic phases had been dried over sodium sulfate and the solvent had been filtered and evaporated down to dryness, the resulting residue was purified by column chromatography (cyclohexane/ethylacetate from 50:50 to 20:80). After that, the filtrate was evaporated down to dryness. The resulting residue was converted into the hydrochloride using ethereal hydrochloric acid, with 417 mg (74% of theory) of the title compound being obtained.

$^1$H-NMR (400 MHz, DMSO-d$_6$): δ [ppm] 11.3 (bs, 1H); 10.0 (s, 1H); 7.8 (d, 1H); 7.6 (d, 2H); 7.4 (d, 2H); 7.3 (d, 1H); 6.9 (d, 1H); 6.0 (m, 1H); 5.5 (m, 2H); 4.3 (m, 1H); 4.0 (m, 1H); 3.7 (m, 1H); 3.4 (m, 1H); 3.2 (m, 3H); 3.0 (m, 3H); 1.4 (d, 3H); 1.2 (d, 6H).

MS [m+1]: 415 (free base).

Example 13a

N-{6-[4-Allyl-(3S)-methylpiperazin-1-yl]pyridin-3-yl}-4-isopropylbenzenesulfonamide (S enantiomer as free base)

The preparation was effected in analogy with the preparation of the racemic compound, with enantiomerically pure (2S)-methylpiperazine being used in step 13.1 instead of racemic 2-methylpiperazine.

$^1$H-NMR (400 MHz, DMSO-d$_6$): δ [ppm] 11.3 (bs, 1H); 10.0 (s, 1H); 7.8 (s, 1H); 7.6 (d, 2H); 7.4 (d, 2H); 7.3 (d, 1H); 6.9 (d, 1H); 6.0 (m, 1H); 5.5 (m, 2H); 4.3 (m, 2H); 4.0 (m, 1H); 3.7 (m, 1H); 3.4 (m, 1H); 3.2 (m, 1H); 3.1 (m, 1H); 3.0 (m, 2H).1.4 (d, 3H); 1.2 (d, 6H).

MS [m+1]: 415 (free base)

Example 14

4-Isopropyl-N-[6-(3-methyl-4-propylpiperazin-1-yl)pyridin-3-yl]benzenesulfonamide hydrochloride 100 mg (0.24 mmol) of N-[6-(4-allyl-3-methylpiperazin-1-yl)pyridin-3-yl]-4-isopropylbenzenesulfonamide hydrochloride from Example 13.4 were dissolved in 10 ml of ethyl acetate, after which 10 mg of palladium on active charcoal (10%) were added and the mixture was stirred overnight at room temperature under a hydrogen atmosphere. After that, the catalyst was filtered off and the filtrate was evaporated down to dryness. After 1 ml of dichloromethane had been added to the resulting residue, diethyl ether was slowly added dropwise until the solution became cloudy. The reaction mixture was stirred for 30 minutes and the precipitate which had formed was filtered off with suction. The filtrate was evaporated down to dryness, after which the residue was dissolved in a 1:1 mixture of dichloromethane and diethyl ether and converted into the hydrochloride by adding ethereal hydrochloric acid. 71 mg (63% of theory) of the title compound were obtained.

$^1$H-NMR (400 MHz, DMSO-d$_6$): δ [ppm] 10.9 (bs, 1H); 10.0 (s, 1H); 7.8 (d, 1H); 7.6 (d, 2H); 7.4 (d, 2H); 7.3 (d, 1H); 6.9 (d, 1H); 4.2 (m, 2H); 3.6 (m, 1H); 3.4-3.0 (m, 7H); 1.7 (m, 2H); 1.4 (d, 3H); 1.2 (d, 6H); 0.9 (m, 3H).

MS [m+1]: 417 (free base).

Example 14a

4-Isopropyl-N-{6-[(3S)-methyl-4-propylpiperazin-1-yl]pyridin-3-yl}benzenesulfonamide as free base (S enantiomer)

The preparation was effected in analogy with the preparation of the racemic compound, with enantiomerically pure (2S)-methylpiperazine being used instead of racemic 2-methylpiperazine.

$^1$H-NMR (400 MHz, DMSO-d$_6$): δ [ppm] 9.7 (s, 1H); 7.7 (s, 1H); 7.6 (d, 2H); 7.4 (d, 2H); 7.2 (d, 1H); 6.7 (d, 1H); 3.8 (m, 2H); 2.9 (m, 2H); 2.8 (m, 1H); 2.6 (m, 2H); 2.3 (m, 1H), 2.1 (m, 2H); 1.4 (m, 2H); 1.2 (d, 6H); 1.0 (m, 3H); 0.8 (m, 3H).

MS [m+1]: 417 (free base)

Example 15

N-[5-(4-Allylpiperazin-1-yl)pyridin-2-yl]-4-isopropylbenzenesulfonamide hydrochloride 15.1 1-Allyl-4-(6-nitropyridin-3-yl)piperazine 315 mg (2.5 mmol) of N-allylpiperazine were dissolved in 5 ml of toluene under an argon atmosphere. 93 mg (0.1 mmol) of tris-(dibenzylideneacetone)-dipalladium(0) (Pd$_2$dba$_3$), 126 mg (0.2 mmol) of 2,2'-bis-(diphenylphosphino)-1,1'-binaphthy I (BINAP), 1.14 g (3.5 mmol) of cesium carbonate and 515 mg (2.54 mmol) of 5-bromo-2-nitropyridine were then added and the mixture was stirred at 120° C., in a microwave oven, for 4 hours. After the reaction mixture had cooled down to room temperature, a saturated aqueous solution of ammonium chloride was added. After that, the aqueous reaction mixture was extracted three times with in each case 50 ml of ethyl acetate. After the organic phase had been dried over sodium sulfate, the drying agent had been filtered off and the solvent had been evaporated down to dryness, the residue was chromatographed through silica gel using ethyl acetate/methanol (4:1), with 304 mg (46% of theory) of the title compound being obtained.

$^1$H-NMR (400 MHz, CDCl$_3$): δ [ppm] 8.2 (m, 2H); 7.2 (dd, 1H); 5.9 (m, 1H); 5.3 (m, 2H); 3.5 (m, 4H); 3.1 (m, 2H); 2.6 (m, 4H).

MS [m+1]: 249

15.2 5-(4-Allylpiperazin-1-yl)pyridine-2-amine 300 mg (1.21 mmol) of 1-allyl-4-(6-nitropyridin-3-yl) piperazine from Example 15.1 were dissolved in 20 ml of methanol, after which 2.18 g (9.67 mmol) of tin(II) chloride dihydrate were added and the mixture was stirred at 70° C. for 2 hours. After the solvent had been evaporated down to dryness, the resulting residue was treated with water and this mixture was made alkaline using a dilute aqueous solution of sodium hydroxide and extracted with ethyl acetate. The solid which had precipitated out was filtered off with suction. The phases were then separated and the aqueous phase was extracted three times with ethyl acetate. The combined organic phases were dried over sodium sulfate, filtered and evaporated down to dryness, with 183 mg (69% of theory) of the title compound being obtained.

MS [m+1]: 219.

15.3 N-[5-(4-Allylpiperazin-1-yl)pyridin-2-yl]-4-isopropyl-benzenesulfonamide hydrochloride 520 mg (2.38 mmol) of 5-(4-allylpiperazin-1-yl)pyridin-2-ylamine and 495 mg (2.26 mmol) of 4-isopropylbenzene-sulfonyl chloride were dissolved in 5 ml of tetrahydrofuran at room temperature, after which 1.0 ml (7.15 mmol) of triethylamine was added dropwise and the mixture was stirred at 40-50° C. for 6 hours. After the solvent had been evaporated down to dryness, the resulting residue was treated with water and this mixture was made acid using 1N aqueous hydrochloric acid and extracted twice with diethyl ether. The aqueous phase was made alkaline, to pH 9-10, using a 1N aqueous solution of sodium hydroxide and then extracted twice with ethyl acetate. After the combined organic phases had been dried over sodium sulfate, the drying agent had been filtered off and the solvent had been evaporated down to dryness, the resulting residue was chromatographed on silica gel using ethyl acetate. After the solvent had been removed, the resulting residue was brought into solution using a little diethyl ether in dichloromethane and then converted into the hydrochloride using ethereal hydrochloric acid. 415 mg (44% of theory) of the title compound were obtained.

$^1$H-NMR (400 MHz, DMSO-d$_6$): δ [ppm] 11.6 (bs, 1H); 7.9 (d, 1H); 7.8 (d, 2H); 7.5 (dd, 1H); 7.4 (d, 2H); 7.1 (d, 1H); 6.0 (m, 1H); 5.5 (m, 2H); 3.7 (m, 4H); 3.4 (m, 2H); 3.1 (m, 4H); 3.0 (m, 1H); 1.2 (d, 6H).

$^{13}$C-NMR (100 MHz, DMSO-d$_6$): δ [ppm] 153.3 (C); 144.5 (C); 141.6 (C); 138.4 (C); 134.3 (CH); 127.3 (CH); 127.0 (CH); 126.8 (CH); 124.8 (CH$_2$); 113.8 (CH); 57.3 (CH$_2$); 49.6 (CH$_2$); 45.2 (CH$_2$); 33.3 (CH); 23.4 (CH$_3$).

MS [m+1]: 401.

Example 16

N-[2-(4-Allylpiperazin-1-yl)pyrimidin-5-yl]-4-iso-propylbenzenesulfonamide 16.1 2-(4-Allylpiperazin-1-yl)-5-nitropyrimidine 114 mg (2.38 mmol) of 50% sodium hydride were added, under a nitrogen atmosphere and while cooling with ice, to a solution of 273 mg (2.17 mmol) of N-allylpiperazine in 5 ml of dimethylformamide. After 30 minutes, a solution of 440 mg (2.17 mmol) of 2-(methylsulfone)-5-nitropyrimidine in 5 ml of dimethylformamide was added dropwise to the reaction mixture. After 10 minutes, 70 ml of water were added and the reaction mixture was extracted twice with in each case 50 ml of ethyl acetate. After the combined organic phases had been dried over sodium sulfate, the drying agent had been filtered off and the solvent had been evaporated to dryness, 535 mg (99% of theory) of the title compound were obtained.

$^1$H-NMR (400 MHz, CDCl$_3$): δ [ppm] 9.0 (s, 2H); 5.8 (m, 1H); 5.2 (m, 2H); 4.0 (m, 4H); 3.1 (m, 2H); 2.5 (m, 4H).

MS [m+1]: 250.

16.2 2-(4-Allylpiperazin-1-yl)pyrimidine-5-amine 3.84 g (17.0 mmol) of tin(II) chloride dihydrate were added to a solution of 530 mg (2.13 mmol) of 2-(4-allylpiperazin-1-yl)-5-nitropyrimidine from Example 16.1 in 20 ml of methanol and, after that, the reaction mixture was heated at reflux for 1 hour. After the solvent had been evaporated to dryness, the residue was treated with saturated aqueous sodium chloride solution and then made alkaline using dilute aqueous sodium hydroxide solution. After that, the aqueous reaction mixture was extracted with ethyl acetate. The solid which had precipitated out was filtered off with suction. The phases were then separated and the aqueous phase was extracted in each case twice with ethyl acetate and dichloromethane. After the combined organic phases had been dried over sodium sulfate, the drying agent had been filtered off and the solvent had been evaporated down to dryness, 220 mg (46% of theory) of the title compound were obtained.

16.3 N-[2-(4-Allylpiperazin-1-yl)pyrimidin-5-yl]-4-isopropylbenzenesulfonamide 216 mg (0.98 mmol) of 2-(4-Allylpiperazin-1-yl)pyrimidin-5-ylamine from Example 16.2 and 215 mg (0.98 mmol) of 4-isopropylbenzenesulfonyl chloride were dissolved in 20 ml of tetrahydrofuran at room temperature, after which 0.4 ml (3.0 mmol) of triethylamine was added dropwise and the mixture was stirred at room temperature overnight. After the solvent had been evaporated down to dryness, water was added to the resulting residue. The aqueous reaction mixture was made acid using 1N aqueous hydrochloric acid and extracted twice with diethyl ether. The aqueous phase was made alkaline to pH 9-10, using a 1N solution of sodium hydroxide and then extracted three times with diethyl ether. The combined organic phases were dried over sodium sulfate. The residue which was obtained after filtering off the drying agent and evaporating the solvent down to dryness was thoroughly stirred with a mixture composed of heptane and diethyl ether, filtered off with suction and dried, with 71 mg (18% of theory) of the title compound being obtained.

$^1$H-NMR (500 MHz, CDCl$_3$): δ [ppm] 8.0 (s, 2H); 7.7 (d, 2H); 7.3 (d, 2H); 6.2 (bs, 1H); 5.9 (m, 1H); 5.2 (m, 2H); 3.8 (m, 4H); 3.1 (m, 2H); 3.0 (m, 1H); 2.5 (m, 4H); 1.3 (d, 6H).

MS [m+1]: 402.

Example 17

4-Isopropyl-N-[2-(4-propylpiperazin-1-yl)pyrimidin-5-yl]benzenesulfonamide hydrochloride 70 mg (0.17 mmol) of N-[2-(4-allylpiperazin-1-yl)pyrimidin-5-yl]-4-isopropylbenzenesulfonamide from Example 16.3 were dissolved in 30 ml of ethyl acetate, after which 10 mg of palladium on active charcoal (10%) were added and the mixture was stirred at room temperature for 2 hours under a hydrogen atmosphere. The catalyst was then filtered off and the filtrate was concentrated by evaporation. The residue was brought into solution using 25 ml of diethyl ether and converted into the hydrochloride with ethereal hydrochloric acid, resulting in 58 mg (76% of theory) of the title compound being obtained.

$^1$H-NMR (400 MHz, DMSO-d$_6$): δ [ppm] 11.0 (bs, 1H); 10.0 (s, 1H); 8.1 (s, 2H); 7.7 (d, 2H); 7.5 (d, 2H); 4.6 (m, 2H); 3.5 (m, 2H); 3.4 (m, 2H); 3.0 (m, 5H); 1.7 (m, 2H); 1.3 (d, 6H); 0.9 m, 3H).

MS [m+1]: 404 (free base).

Example 18

N-[6-(4-Allylpiperazin-1-yl)pyrimidin-4-yl]-4-isopropylbenzenesulfonamide 18.1 N-(6-Chloropyrimidin-4-yl)-4-isopropylbenzenesulfonamide 996 mg (5.0 mmol) of isopropylbenzenesulfonamide were dissolved in 20 ml of dimethyl sulfoxide, after which 288 mg (6.0 mmol) of 50% sodium hydride were added and the mixture was stirred at room temperature for 30 minutes. 819 mg (5.5 mmol) of 4,6-dichloropyrimidine were then added and the reaction mixture was stirred overnight at room temperature. Subsequently, the mixture was heated at 90° C. for 3 hours and, after that, stirred at 120° C., in a microwave oven, for 30 minutes. After the reaction mixture had cooled down to room temperature, it was diluted with 150 ml of water, neutralized with citric acid and extracted three times with diethyl ether. The residue, which was obtained after drying with sodium sulfate and after removing the solvent, was dissolved in 100 ml of diethyl ether and extracted with an aqueous solution of sodium hydrogen carbonate. The aqueous phase was acidified and extracted with diethyl ether. The organic phase was dried, filtered and evaporated down to dryness, with 440 mg (28% of theory) of the title compound being obtained.

MS [m+1]: 312.

18.2 N-[6-(4-Allylpiperazin-1-yl)pyrimidin-4-yl]-4-isopropylbenzenesulfonamide 430 mg (1.38 mmol) of N-(6-chloropyrimidin-4-yl)-4-isopropylbenzenesulfonamide from Example 18.1 were dissolved in 3 ml of dimethyl sulfoxide, after which 1.74 g (13.79 mmol) of N-allylpiperazine were added and the mixture was stirred overnight. Subsequently, the reaction mixture was stirred at 100° C., in a microwave oven, for 45 minutes. After the reaction mixture had cooled down to room temperature, it was diluted with 50 ml of water. After that, the aqueous reaction mixture was extracted with 50 ml of ethyl acetate and the precipitate was filtered off with suction, with 190 mg (34% of theory) of the title compound being obtained.

$^1$H-NMR (400 MHz, CDCl$_3$): δ [ppm] 8.4 (s, 1H); 7.8 (d, 2H); 7.3 (d, 2H); 6.1 (s, 1H); 5.9 (m, 1H); 5.2 (m, 2H); 3.6 (m, 4H); 3.0 (m, 3H); 2.5 (m, 4H); 1.3 (d, 6H).

MS [m+1]: 402.

Example 19

N-[2-(4-Allylpiperazin-1-yl)pyridin-5-yl]-4-bromobenzenesulfonamide hydrochloride The preparation was effected in analogy with Example 1.3, with 4-bromobenzenesulfonyl chloride being used instead of 4-isopropylbenzenesulfonyl chloride. The reaction product which was obtained was converted into the hydrochloride using ethereal hydrochloric acid, resulting in 398 mg of the title compound.

MS [m+1]: 436/438

Example 20

N-[6-(4-Allylpiperazin-1-yl)pyridin-3-yl]-4-cyclopropylbenzenesulfonamide 398 mg (0.84 mmol) of N-[6-(4-allylpiperazin-1-yl)pyridin-3-yl]-4-bromobenzenesulfonamide from Example 19, 101 mg (1.18 mmol) of cylcopropylboronic acid, 676 mg (3.19 mmol) of K$_3$PO$_4$ and 26 mg (0.09 mmol) of tricyclohexylphosphine were dissolved in 4 ml of toluene and 0.2 ml of water under a nitrogen atmosphere. 10 mg (0.04 mmol) of palladium(II) acetate were then added and the mixture was stirred at 100° C., in a microwave oven, for one hour. After the solvent had been evaporated down to dryness, the resulting residue was treated with water and the mixture was then extracted with ethyl acetate. Because the phases only separated poorly, the finely divided solid was filtered off. The aqueous phase was extracted twice with ethyl acetate. After the combined organic phases had bee n dried over sodium sulfate and the solvent had been filtered and evaporated down to dryness, the resulting residue was purified by column chromatography.

MS [m+1]: 399 $^1$H-NMR (400 MHz, DMSO-d$_6$): δ [ppm] 11.1 (bs, 1H); 9.9 (s, 1H); 7.8 (s, 1H); 7.6 (d, 2H); 7.3 (dd, 1H); 7.2 (d, 2H); 6.9 (d, 1H); 6.0 (m, 1H); 5.5 (d, 2H); 4.3 (m, 2H); 3.8 (m, 2H); 3.4 (m, 2H); 3.2 (m, 2H); 3.0 (m, 2H); 2.0 (m, 1H); 1.0 (m, 2H); 0.8 (m, 2H).

The compounds of the following examples 21 to 40 were prepared in analogous manner:

Example 21

4-Isopropyl-N-[2-(4-propylpiperazin-1-yl)pyridin-3-yl]-benzenesulfonamide hydrochloride MS [m+1]: 403 (free base).

Example 22

4-Isopropyl-N-[2-(3,5-dimethyl-4-propylpiperazin-1-yl)pyridin-3-yl]benzenesulfonamide trifluoroacetate MS [m+1]: 431 (free base).

Example 23

N-[2-(4-Allyl-3-methylpiperazin-1-yl)pyridin-3-yl]-4-trifluoromethylbenzenesulfonamide hydrochloride MS [m+1]: 441 (free base).

Example 24

N-[6-(4-Allyl-3,5-dimethylpiperazin-1-yl)pyridin-3-yl]-4-isopropylbenzenesulfonamide hydrochloride MS [m+1]: 429 (free base)

Example 25

N-[6-(4-Allyl-3,5-dimethylpiperazin-1-yl)pyridin-3-yl]-4-trifluoromethylbenzenesulfonamide hydrochloride MS [m+1]: 455 (free base)

Example 26

N-[6-(4-Allylpiperazin-1-yl)pyridin-3-yl]-4-trifluoromethylbenzenesulfonamide

MS [m+1]: 427

Example 27

4-Bromo-N-[6-(4-propylpiperazin-1-yl)pyridin-3-yl]-benzenesulfonamide

MS [m+1]: 439/441

Example 28

4-Chloro-N-[6-(4-propylpiperazin-1yl)pyridin-3-yl]-benzenesulfonamide

MS [m+1]: 395

Example 29

4-Isopropyl-N-[6-(5-propyl-2,5-diazabicyclo[2.2.1]hept-2-yl)pyridin-3-yl]-benzenesulfonamide hydrochloride MS [m+1]: 415 (free base)

Example 30

N-[6-(5-Allyl-2,5-diazabicyclo[2.2.1]hept-2-yl)pyridin-3-yl]-4-isopropylbenzenesulfonamide hydrochloride MS [m+1]: 413 (free base)

Example 31

N-[6-(4-Propylpiperazin-1-yl)pyridin-3-yl]-4-vinylbenzenesulfonamide hydrochloride MS [m+1]: 387 (free base)

Example 32

N-{6-[4-(3-Fluoropropyl)piperazin-1-yl]pyridin-3-yl}-4-isopropylbenzenesulfonamide hydrochloride MS [m+1]: 421 (free base)

Example 33

4-Isopropyl-N-[6-(4-prop-2-yn-1-ylpiperazin-1-yl)pyridin-3-yl]-benzenesulfonamide hydrochloride MS [m+1]: 399 (free base)

Example 34

4-Ethyl-N-[6-(4-propylpiperazin-1-yl)pyridin-3-yl]-benzenesulfonamide hydrochloride MS [m+1]: 389 (free base)

Example 35

N-[6-(4-Allylpiperazin-1-yl)pyridin-3-yl]-4-chlorobenzenesulfonamide hydrochloride MS [m+1]: 393 (free base)

Example 36

4-Isopropyl-N-(4-methyl-6-piperazin-1-ylpyridin-3-yl)-benzenesulfonamide hydrochloride MS [m+1]: 375 (free base)

Example 37

N-[6-(4-Allylpiperazin-1-yl)-4-methylpyridin-3-yl]-4-isopropylbenzenesulfonamide hydrochloride MS [m+1]: 415 (free base)

Example 38

4-Isopropyl-N-[4-methyl-6-(4-propylpiperazin-1-yl)pyridin-3-yl]-benzenesulfonamide hydrochloride MS [m+1]: 417 (free base)

Example 39

N-[4-Methyl-6-(4-propylpiperazin-1-yl)pyridin-3-yl]-4-vinylbenzenesulfonamide hydrochloride MS [m+1]: 401 (free base)

Example 40

N-[6-(4-Butylpiperazin-1-yl)pyridin-3-yl]-4-isopropylbenzenesulfonamide hydrochloride MS [m+1]: 417 (free base)

Example 41

N{6-[(3S)-4-Ethyl-3-methylpiperazin-1-yl]pyridin-3-yl}-4-isopropylbenzenesulfonamide hydrochloride MS [m+1]: 403 (free base)

Example 42

N-[2-(4-Allylpiperazin-1-yl)pyridin-5-yl]-4-(N-pyrrolidinyl)benzenesulfonamide fumarate Reaction of 0.300 g of 6-(4-allylpiperazin-1-yl)-2-methylpyridin-3-amine (1.29 mmol) and 0.282 g of 4-isopropylbenzene-1-sulfonyl chloride (1.29 mmol) in 10 ml of a mixture of pyridine and dichloromethane (1:2) yielded 0.465 g (87%) of the title compound as a white solid. The title compound was onverted into the fumarate salt in methanol by addition of fumaric acid.

MS [m+1]: 415

$^1$H-NMR (400 MHz, CH$_3$OD): δ [ppm]: 7.6 (d, 2H), 7.5 (d, 2H), 7.3 (m, 1H), 7.2 (m, 1H), 7.1 (d, 1H), 6.5 (d, 1H), 5.9 (m, 1H), 5.4 (m, 2H), 3.5 (m, 5H), 3.0 (m, 4H), 2.8 (m, 2H), 1.9 (s, 3H), 1.2 (m, 6H).

Example 43

4-Isopropyl-[N-[2-(4-allylpiperazin-1-yl)-6-methylpyridin-5-yl]-4-(N-pyrrolidinyl)benzenesulfonamide, Fumarate Reaction of 0.300 g of 6-(4-allylpiperazin-1-yl)-2-methylpyridin-3-amine (1.29 mmol) and 0.282 g of 4-isopropylbenzene-1-sulfonyl chloride (1.29 mmol) in 10 ml of a mixture of pyridine/dichloromethane (1:2) yielded 0.465 g (87%) of the title compound as a white solid. The title compound was converted into the fumarate salt in methanol by addition of fumaric acid.

MS [m+1]: 415 $^1$H-NMR (400 MHz, MeOD): δ [ppm] 7.6 (d, 2H), 7.5 (d, 2H), 7.3 (m, 1H), 7.2 (m, 1H), 7.1 (d, 1H), 6.5 (d, 1H), 5.9 (m, 1H), 5.4 (m, 2H), 3.5 (m, 5H), 3.0 (m, 4H), 2.8 (m, 2H), 1.9 (s, 3H), 1.2 (m, 6H).

Example 44

4-tert-Butyl-[N-[2-(4-allylpiperazin-1-yl)-6-methylpyridin-5-yl]-benzenesulfonamide, fumarate Reaction of 0.300 g of 6-(4-allylpiperazin-1-yl)-2-methylpyridin-3-amine (1.29 mmol) and 0.300 g of 4-tert-butyl-benzene-1-sulfonyl chloride (1.29 mmol) in 10 ml of a mixture of pyridine/dichloromethane (1:2) yielded 0.525 g (95%) of the title compound as a white solid. The title compound was onverted into the fumarate salt in methanol by addition of fumaric acid. MS [m+1]: 429

$^1$H-NMR (400 MHz, DMSO-d$_6$): δ [ppm] 9.3 (s, 2H), 8.6 (d, 2H), 7.8 (m, 1H), 7.4 (m, 2H), 7.0 (d, 1H), 6.6 (d, 1H), 5.8 (m, 1H), 5.2 (m, 2H), 3.4 (m, 4H), 2.9 (m, 2H), 2.4 (m, 4H), 1.9 (s, 3H), 1.3 (s, 9H).

Example 45

4-tert-pentyl-[N-[2-(4-Allylpiperazin-1-yl)-6-methylpyridin-5-yl]-benzenesulfonamide, Fumarate Reaction of 0.300 g of 6-(4-allylpiperazin-1-yl)-2-methylpyridin-3-amine (1.29 mmol) and 0.318 g of 4-tert-pentylbenzene-1-sulfonyl chloride (1.29 mmol) in 10 mL pyridine-dichloromethane (1:2) yielded 0.564 g (99%) of the title compound as a white solid. The title compound was onverted into the fumarate salt in methanol by addition of fumaric acid. MS [m+1]: 443

$^1$H-NMR (400 MHz, DMSO-d$_6$): δ [ppm] 9.3 (s, 2H), 8.6 (d, 2H), 7.8 (m, 1H), 7.4 (m, 2H), 7.0 (d, 1H), 6.5 (d, 1H), 5.8 (m, 1H), 5.2 (m, 2H), 3.4 (m, 4H), 3.0 (m, 2H), 2.4 (m, 4H), 1.9 (s, 3H), 1.6 (m, 2H), 1.2 (s, 6H), 0.6 (t, 3H).

The compounds of Examples 46 to were prepared in analogous manner:

Example 46

4-Ethyl-N-[6-((S)-3-methyl-4-propyl-piperazin-1-yl)-pyridin-3-yl]-benzenesulfonamide, hydrochloride $^1$H-NMR (400 MHz, DMSO-d$_6$): δ [ppm] 10.9 (bs, 1H); 10.0 (s,1H); 7.8 (m, 1H); 7.6 (d, 2H); 7.4 (d, 2H); 7.3 (dd, 1H); 6.9 (d, 1H); 4.3 (m, 2H); 3.5-2.9 (m, 7H); 2.7 (m, 2H); 1.7 (m, 2H); 1.4 (m, 2H); 1.2 (m, 4H); 0.9 (t, 3H).

MS [m+1]: 403

Example 47

N-[6-((S)-3-methyl-4-propyl-piperazin-1-yl)-pyridin-3-yl]-4-vinylbenzenesulfonamide, hydrochloride $^1$H-NMR (400 MHz, DMSO-d$_6$): δ [ppm] 10.4 (bs, 1H); 10.0 (s, 1H); 7.8 (s, 1H); 7.7 (m, 4H); 7.3 (d, 1H); 6.9 (d, 1H); 6.8 (dd, 1H); 6.0 (d, 1H); 5.4 (d, 1H); 4.3 (m, 2H); 3.5 (m, 1H); 3.3-2.9 (m, 6H); 1.7 (m, 2H); 1.4 (m, 2H); 1.2 (m, 1H); 0.9 (t, 3H).

MS [m+1]: 401

Example 48

N-[6-((S)-4-Allyl-3-methyl-piperazin-1-yl)-2-methoxy-pyridin-3-yl]-4-isopropylbenzenesulfonamide, hydrochloride $^1$H-NMR (400 MHz, DMSO-d$_6$): δ [ppm] 11.1 (bs, 1H); 9.2 (s, 1H); 7.6 (d, 2H); 7.4 (d, 2H); 7.3 (m,1H); 6.4 (m, 1H); 6.0 (m, 1H); 5.5 (m, 2H); 4.3 (m, 2H); 4.0 (m, 1H); 3.7 (m, 2H); 3.4-3.2 (m, 5H); 3.1 (m, 1H); 3.0 (m, 2H); 1.4 (m, 2H); 1.2 (m, 7H).

MS [m+1]: 445

Example 49

4-Isopropyl-N-[2-methoxy-6-((S)-3-methyl-4-propyl-piperazin-1-yl)-pyridin-3-yl]-benzenesulfonamide, hydrochloride $^1$H-NMR (400 MHz, DMSO-d$_6$): δ [ppm] 10.8 (bs, 1H); 9.3 (s, 1H); 7.6 (d, 2H); 7.4 (d, 2H); 7.3 (m, 1H); 6.4 (m, 1H); 4.2 (m, 2H); 3.5-3.2 (m, 8H); 3.1 (m, 1H); 3.0 (m, 2H); 1.7 (m, 2H); 1.4 (m, 2H); 1.2 (m, 7H); 0.9 (t, 3H).

MS [m+1]: 447

Example 50

N-[6-((S)-4-Allyl-3-ethyl-piperazin-1-yl)-pyridin-3-yl]-4-isopropylbenzenesulfonamide, hydrochloride $^1$H-NMR (400 MHz, DMSO-d$_6$): δ [ppm] 11.2 (bs, 1H); 10.0 (s, 1H); 7.8 (d, 1H); 7.6 (d, 2H); 7.4 (d, 2H); 7.3 (m,1H); 6.9 (d, 1H); 6.0 (m, 1H); 5.5 (m 2H); 4.2 (m, 2H); 4.0 (m, 2H); 3.4-3.0 (m, 6H); 1.7 (m, 2H); 1.2 (d, 6H); 1.0 (t, 3H).

MS [m+1]: 429

Example 51

N-[6-((S)-3-Ethyl-4-propyl-piperazin-1-yl)-pyridin-3-yl]-4-isopropylbenzenesulfonamide, hydrochloride $^1$H-NMR(400 MHz, DMSO-d$_6$): δ [ppm] 11.2 (bs, 1H); 10.2 (s, 1H); 7.8 (d, 1H); 7.7 (d, 2H); 7.4 (m, 3H); 7.0 (d, 1H); 4.2 (m, 2H); 3.6-3.0 (m, 8H); 2.0 (m, 1H); 1.7 (m, 3H); 1.2 (d, 6H); 1.0 (m, 6H).

MS [m+1]: 431

Example 52

4-Isopropyl-N-(2-piperazin-1-yl-pyrimidin-5-yl)-benzenesulfonamide

$^1$H-NMR (400 MHz, DMSO-d$_6$): δ [ppm] 8.0 (s, 2H); 7.6 (d, 2H); 7.4 (d, 2H); 3.6 (m, 4H); 3.0 (m, 1H); 2.7 (m, 4H); 1.2 (d, 6H).
MS [m+1]: 362

Example 53

N-[2-(4-Ethyl-piperazin-1-yl)-pyrimidin-5-yl]-4-isopropylbenzenesulfonamide, hydrochloride

$^1$H-NMR (400 MHz, D$_2$O): δ [ppm] 7.7 (s, 2H); 7.3 (d, 2H); 7.1 (d, 2H); 4.3 (m, 2H); 3.3 (m, 2H); 3.0 (m, 4H); 2.7 (m, 3H); 1.0 (t, 3H); 0.9 (d, 6H).
MS [m+1]: 390

Example 54

N-[2-((S)-4-Ethyl-3-methyl-piperazin-1-yl)-pyrimidin-5-yl]-4-isopropylbenzenesulfonamide, hydrochloride

$^1$H-NMR (400 MHz, DMSO-d$_6$): δ [ppm] 10.7 (bs, 1H); 10.0 (s, 1H); 8.1 (m, 2H); 7.6 (d, 2H); 7.4 (d, 2H); 4.6 (m, 2H); 3.4 (m, 4H); 3.2 (m, 1H); 3.0 (m, 3H); 1.4 (m, 2H); 1.2 (m, 10H).
MS [m+1]: 404

Example 55

N-[2-((S)-4-Allyl-3-methyl-piperazin-1-yl)-pyrimidin-5-yl]-4-isopropyl-benzenesulfonamide, hydrochloride

$^1$H-NMR (400 MHz, DMSO-d$_6$): δ [ppm] 11.0 (bs, 1H); 10.0 (s, 1H); 8.1 (s, 2H); 7.6 (d, 2H); 7.4 (d, 2H); 6.0 (m, 1H); 5.5 (m, 2H); 4.6 (m, 2H); 4.0 (m, 2H); 3.7 (m, 2H); 3.3 (m, 3H); 3.0 (m,1 H); 1.4 (m, 2H); 1.2 (m, 7H).
MS [m+1]: 416

Example 56

4-Isopropyl-N-[2-((S)-3-methyl-4-propyl-piperazin-1-yl)-pyrimidin-5-yl]-benzenesulfonamide, hydrochloride

$^1$H-NMR (400 MHz, DMSO-d$_6$): δ [ppm] 10.6 (bs, 1H); 10.0 (s, 1H); 8.1 (m, 2H); 7.6 (d, 2H); 7.4 (d, 2H); 4.5 (m, 2H); 3.5 (m, 2H); 3.3 (m, 3H); 3.0 (m, 3H); 1.7 (m, 2H); 1.4 (m, 2H); 1.2 (m, 7H); 0.9 (t, 3H). MS [m+1]: 418

Example 57

4-Ethyl-N-[2-((S)-3-methyl-4-propyl-piperazin-1-yl)-pyrimidin-5-yl]-benzenesulfonamide, hydrochloride

$^1$H-NMR (400 MHz, DMSO-d$_6$): δ [ppm] 10.8 (bs, 1H); 10.0 (s,1H); 8.1 (m, 2H); 7.6 (d, 2H); 7.4 (d, 2H); 4.5 (m, 2H); 3.5 (m, 2H); 3.3 (m, 3H); 3.0 (m, 2H); 2.7 (m, 2H); 1.7 (m, 2H); 1.4 (m, 2H); 1.2 (m, 4H); 0.9 (t, 3H).
MS [m+1]: 404

Example 58

N-[2-((S)-3-Methyl-4-propyl-piperazin-1-yl)-pyrimidin-5-yl]-4-vinylbenzenesulfonamide, hydrochloride

$^1$H-NMR (400 MHz, DMSO-d$_6$): δ [ppm] 10.7 (bs, 1H); 10.0 (s, H); 8.1 (d, 2H); 7.7 (m, 4H); 6.8 (dd, 1H); 6.0 (d, 1H); 5.5 (d, 1H); 4.5 (m, 2H); 3.5 (m, 2H); 3.3 (m, 3H); 3.0 (m, 2H); 1.7 (m, 2H); 1.4 (m, 2H); 1.2 (m, 1H); 0.9 (t, 3H).
MS [m+1]: 402

Example 59

4-Isopropyl-benzenesulfonic acid 6-(4-allyl-piperazin-1-yl)-pyridin-3-yl ester

59.1 4-Isopropyl-benzenesulfonic acid 6-chloro-pyridin-3-yl ester

A reaction flask containing 500 mg of 6-chloropyridin-3-ol (3.86 mmol) and 844 mg of 4-isopropyl-benzenesulfonylchloride (0.20 mmol) in dry tetrahydrofurane (10 ml) was flushed with N$_2$. 1.6 ml of triethylamine were added and the reaction mixture was stirred at room temperature for 2 h. Thereby 4-isopropyl-benzenesulfonic acid 6-chloro-pyridin-3-yl ester ester was obtained in 98% yield.

MS [m+1]: 312 $^1$H-NMR (400 MHz, DMSO-d$_6$): δ [ppm] 8.1 (d, 1H); 7.8 (d, 2H); 7.6 (m, 4H); 3.0 (m,1H); 1.2 (d, 6H).

59.2 4-Isopropyl-benzenesulfonic acid 6-(4-allyl-piperazin-1-yl)-pyridin-3-yl ester A flask containing 45 mg of palladium(II) acetate (0.2 mmol), 126 mg of BINAP (0.20 mmol) and 0.233 mg of sodium tert-butylate in dry toluene (15 mL) was flushed with nitrogen 1.275 g of 1-allylpiperazin (10 mmol) were added and the reaction mixture was heated to 50° C. 630 mg of 4-isopropyl-benzenesulfonic acid 6-chloro-pyridin-3-yl ester (2.0 mmol) were dissolved in toluene and the solution was slowly added over a period of 10 minutes into the reaction mixture with stirring. The mixture was heated to reflux with stirring for 7 h. Thereby 4-isopropyl-benzenesulfonic acid 6-(4-allyl-piperazin-1-yl)-pyridin-3-yl ester was obtained in 21% yield.

MS [m+1]: 402 $^1$H-NMR (400 MHz, DMSO-d$_6$): δ [ppm] 7.8 (d, 2H); 7.7 (d, 1H); 7.6 (d, 2H); 7.2 (dd, 1H); 6.8 (d, 1H); 5.8 (m, 1H); 5.2 (m, 2H); 3.5 (m, 4H); 3.0 (m, 3H); 2.5 (m, 4H); 1.2 (d, 6H).

Example 60

4-Isopropyl-benzenesulfonic acid 6-(4-propyl-piperazin-1-yl)-pyridin-3-yl ester, hydrochloride

In a reaction flask 5 mg of palladium on charcoal were added to 50 mg of 4-isopropylbenzenesulfonic acid 6-(4-allyl-piperazin-1-yl)-pyridin-3-yl ester from example 59(0.12 mmol) in dry ethyl acetate (5 ml). The atmosphere was then charged with hydrogen gas and the reaction mixture was stirred at room temperature for 1 hour. Thereby, 4-isopropyl-benzenesulfonic acid 6-(4-propyl-piperazin-1-yl)-pyridin-3-yl ester were obtained in 58% yield. The compound was converted into its hydrochloride salt by addition of HCl in ether.

MS [m+1]: 404 $^1$H-NMR (400 MHz, DMSO-d$_6$): δ [ppm] 11.0 (bs, 1H); 7.8 (m, 3H); 7.6 (d, 2H); 7.3 (dd, 1H); 6.9 (d, 1H); 4.3 (d, 2H); 3.5 (d, 2H); 3.3 (dd, 2H); 3.0 (m, 5H); 1.7 (m, 2H); 1.3 (d, 6H); 0.9 (t, 3H).

Examples of Galenic Administration Forms
  A) Tablets
    Tablets of the following composition are pressed on a tablet press in the customary manner:
    40 mg of substance from Example 2
    120 mg of corn starch
    13.5 mg of gelatin
    45 mg of lactose
    2.25 mg of Aerosil® (chemically pure silicic acid in submicroscopically fine dispersion)
    6.75 mg of potato starch (as a 6% paste)
  B) Sugar-coated tablets
    20 mg of substance from Example 2
    60 mg of core composition
    70 mg of saccharification composition
    The core composition consists of 9 parts of corn starch, 3 parts of lactose and 1 part of 60:40 vinylpyrrolidone/vinyl acetate copolymer. The saccharification composition consists of 5 parts of cane sugar, 2 parts of corn starch, 2 parts of calcium carbonate and 1 part of talc. The sugar-coated tablets which had been prepared in this way are subsequently provided with a gastric juice-resistant coating.

Biological Investigations—Receptor Binding Studies:
  The substance to be tested was either dissolved in methanol/Chremophor® (BASF-AG) or in dimethyl sulfoxide and then diluted with water to the desired concentration.

Dopamine $D_3$ Receptor:
  The assay mixture (0.250 ml) was composed of membranes derived from ~$10^6$ HEK-293 cells possessing stably expressed human dopamine $D_3$ receptors, 0.1 nM $[^{125}I]$-iodosulpride and incubation buffer (total binding) or, in addition, test substance (inhibition curve) or 1 µM spiperone (nonspecific binding). Each assay mixture was run in triplicate.
  The incubation buffer contained 50 mM tris, 120 mM NaCl, 5 mM KCl, 2 mM $CaCl_2$, 2 mM $MgCl_2$ and 0.1% bovine serum albumin, 10 µM quinolone and 0.1% ascorbic acid (prepared fresh daily). The buffer was adjusted to pH 7.4 with HCl.

Dopamine $D_{2L}$ Receptor:
  The assay mixture (1 ml) was composed of membranes from ~$10^6$ HEK-293 cells possessing stably expressed human dopamine $D_{2L}$ receptors (long isoform) and 0.01 nM $[^{125}I]$ iodos-piperone and incubation buffer (total binding) or, in addition, test substance (inhibition curve) or 1 µM haloperidol (nonspecific binding). Each assay mixture was run in triplicate.
  The incubation buffer contained 50 mM tris, 120 mM NaCl, 5 mM KCl, 2 mM $CaCl_2$, 2 mM $MgCl_2$ and 0.1% bovine serum albumin. The buffer was adjusted to pH 7.4 with HCl.

Measurement and Analysis:
  After having been incubated at 25° C. for 60 minutes, the assay mixtures were filtered through a Whatman GF/B glass fiber filter under vacuum using a cell collecting device. The filters were transferred to scintillation viols using a filter transfer system. After 4 ml of Ultima Gold® (Packard) have been added, the samples were shaken for one hour and the radioactivity was then counted in a Beta-Counter (Packard, Tricarb 2000 or 2200CA). The cpm values were converted into dpm using a standard quench series and the program belonging to the instrument.
  The inhibition curves were analyzed by means of iterative nonlinear regression analysis using the Statistical Analysis System (SAS) which is similar to the "LIGAND" program described by Munson and Rodbard.
  In these tests, the compounds according to the invention exhibit very good affinities for the $D_3$ receptor (<100 nM, frequently <50 nM) and bind selectively to the $D_3$ receptor. The results of the binding tests are given in Table 1.

TABLE 1

| Example | $K_i$ ($D_3$) [nM] | Selectivity vs. $D_2L$* |
|---|---|---|
| 1 | 3.0 | 232 |
| 2 | 5.5 | 25 |
| 3 | 5.9 | 15 |
| 5 | 11.4 | 108 |
| 6 | 9.7 | 169 |
| 7 | 11.4 | 68 |
| 10 | 7.5 | 93 |
| 11 | 6.2 | 77 |
| 13 | 3.6 | 131 |
| 13a | 2.7 | 96 |
| 14 | 2.5 | 81 |
| 14a | 1.5 | 184 |
| 16 | 3.8 | 131 |
| 17 | 8.2 | 148 |
| 19 | 36.9 | 91 |
| 22 | 21.9 | 22 |
| 24 | 25.0 | 47 |
| 27 | 21.4 | 55 |
| 28 | 25.3 | 67 |
| 29 | 16.9 | 31 |
| 30 | 11.1 | 17 |
| 31 | 14.0 | 96 |
| 32 | 17.0 | 74 |
| 34 | 9.6 | 73 |
| 35 | 26.6 | 51 |
| 36 | 5.4 | 50 |
| 37 | 2.7 | 86 |
| 38 | 17.2 | 22 |
| 39 | 34.6 | 30 |
| 42 | 5.3 | 33 |
| 43 | 1.1 | 80 |
| 44 | 1.4 | 41 |
| 45 | 1.4 | 24 |
| 46 | 7.1 | 50 |
| 47 | 6.1 | 118 |
| 48 | 0.8 | 21 |
| 49 | 0.4 | 19 |
| 50 | 9.9 | 57 |
| 51 | 3.1 | 101 |
| 52 | 14.2 | 63 |
| 53 | 8.8 | 149 |
| 54 | 2.3 | 84 |
| 55 | 2.9 | 159 |
| 56 | 1.6 | 399 |
| 57 | 7.3 | 234 |
| 58 | 6.2 | 254 |
| 59 | 16.2 | 75 |
| 60 | 17.4 | 47 |

*$K_i(D_3)/K_i(D_{2L})$

The invention claimed is:
1. An N-[(piperazinyl)hetaryl]arylsulfonamide compound of the general formula I

$$R^1-N\overset{\frown}{\underset{\smile}{\phantom{X}}}N-Q-R-SO_2-Ar \quad (I)$$

$(R^2)_n$ in which
  R is oxygen, a group $N-R^3$ or a group $CR^{3a}R^{3b}$;
  Q is a bivalent, 6-membered heteroaromatic radical selected from pyridindiyl and pyrimidindiyl, and which optionally carries one or two substituents $R^a$ which is/are selected, independently of each other, from halogen, CN, NO$_2$, CO$_2$R$^4$, COR$^5$, C$_1$-C$_4$-alkyl, C$_1$-C$_4$-alkoxy, C$_1$-C$_4$-haloalkyl, NH$_2$, NHR$^6$, NR$^6$R$^7$ and C$_1$-C$_4$-haloalkoxy;

Ar is phenyl or a 6-membered heteroaromatic radical selected from pyridinyl and pyrimidinyl, and which carries one or two substituents $R^b$, which is/are selected from halogen, NO$_2$, CN, CO$_2$R$^4$, COR$^5$, NHR$^6$, NR$^6$R$^7$, C$_1$-C$_6$-alkyl, C$_1$-C$_6$-haloalkyl, C$_1$-C$_6$-alkoxy, C$_1$-C$_6$-haloalkoxy, C$_2$-C$_6$-alkenyl, C$_2$-C$_6$-alkynyl, C$_3$-C$_8$-cycloalkyl, C$_3$-C$_6$-cycloalkoxy, C$_3$-C$_6$-cycloalkyl-C$_1$-C$_4$-alkyl and C$_1$-C$_4$-haloalkyl, with it also being possible for two radicals Rb which are bonded to adjacent C atoms of Ar to be together C$_3$-C$_4$-alkylene; n 0, 1 or 2;

$R^1$ is hydrogen, C$_1$-C$_4$-alkyl, C$_1$-C$_4$-haloalkyl, C$_3$-C$_6$-cycloalkyl, C$_3$-C$_6$-cycloalkyl-C$_1$-C$_4$-alkyl, C$_1$-C$_4$-hydroxyalkyl, C$_1$-C$_4$-alkoxy-C$_1$-C$_4$-alkyl, C$_3$-C$_4$-alkenyl or C$_3$-C$_4$-alkynyl;

$R^2$ is C$_1$-C$_4$-alkyl or, together with $R^1$, is C$_2$-C$_5$-alkylene or, in the case of n=2, the two radicals $R^2$ can together be C$_1$-C$_4$-alkylene;

$R^3$ is hydrogen or C$_1$-C$_4$-alkyl;

$R^{3a}$, $R^{3b}$ are, independently of each other, hydrogen or C$_1$-C$_4$-alkyl;

$R^4$ is C$_1$-C$_4$-alkyl, C$_1$-C$_4$-haloalkyl, C$_2$-C$_4$-alkenyl C$_3$-C$_6$-cycloalkyl, C$_3$-C$_6$-cycloalkyl-C$_1$-C$_4$-alkyl, phenyl or benzyl; and $R^5$ is hydrogen, C$_1$-C$_4$-alkyl, C$_1$-C$_4$-haloalkyl, C$_2$-C$_4$-alkenyl C$_3$-C$_8$-cycloalkyl, C$_3$-C$_8$-cycloalkyl-C$_1$-C$_4$-alkyl, phenyl or benzyl;

$R^6$, $R^7$ are each independently selected from C$_1$-C$_4$-alkyl, C$_1$-C$_4$-haloalkyl or together with the nitrogen to which they are bound form a saturated 3-, 4-, 5- or 6-membered heterocycle, which additionally may comprise an oxygen atom or an additional nitrogen atom as a ring member and which may carry 1, 2, 3 or 4 C$_1$-C$_4$ alkyl groups;

the N-oxides thereof and the physiologically tolerated acid addition salts of these compounds;

with the exception of the compounds: 4-methyl-N-[6-(4-methylpiperazin-1-yl)pyridin-3-yl) benzenesulfonamide and 4-chloro-N-[6-(4-methylpiperazin-1-yl)pyridin-3-yl) benzenesulfonamide.

2. The compound as claimed in claim 1, wherein R is N—R$^3$ with R$^3$ being H or C$_1$—C$_4$-alkyl.

3. The compound as claimed in claim 2, wherein

Q is a bivalent, 6-membered heteroaromatic radical selected from pyridindiyl and pyrimidindiyl, and which optionally carries one or two substituents $R^a$ which is/are selected, independently of each other, from halogen, CN, NO$_2$, CO$_2$R$^4$, COR$^5$, C$_1$-C$_4$-alkyl and C$_1$-C$_4$-haloalkyl and Ar is phenyl or a 6-membered heteroaromatic radical selected from pyridinyl and pyrimidinyl, and which carries one or two substituents R$_b$, which is/are selected from halogen, NO$_2$, CN, CO$_2$R$^4$, COR$^5$, C$_1$-C$_6$-alkyl, C$_2$-C$_6$-alkenyl, C$_2$-C$_6$-alkynyl, C$_3$-C$_6$-cycloalkyl, C$_3$-C$_6$-cycloalkyl-C$_1$-C$_4$-alkyl and C$_1$-C$_4$-haloalkyl, with it also being possible for two radicals R$^b$ which are bonded to adjacent C atoms of Ar to be together C$_3$-C$_4$-alkylene.

4. The compound as claimed in claim 1, in which the piperazine ring is bonded to the heteroaromatic radical Q in the para position in relation to the group R—SO$_2$—Ar.

5. The compound as claimed in claim 1, in which Q is a radical of the formula

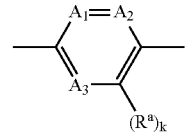

one of the variables $A_1$, $A_2$ or $A_3$ is N, the remaining two variables being CH or C—R$^a$, or $A_1$ and $A_3$ are N and $A_3$ is CH or C—R$^a$, k=0 or 1 and $R^a$ is selected from halogen, C$_1$-C$_4$-alkyl, C$_1$-C$_4$-haloalkyl, C$_1$-C$_4$-alkoxy, NH$_2$, NHR$^6$, NR$^6$R$^7$ and C$_1$-C$_4$-haloalkoxy, with the proviso that k is 0 if two of the variables $A_1$, $A_2$ and $A_3$ are C—R$^a$.

6. The compound as claimed in claim 5, in which $A_3$ is nitrogen, $A_2$ is CH and $A_1$ is N or CH and wherein the piperazine radical is located in the 2 position.

7. The compound as claimed in claim 6, in which Q is pyridin-2,5-diyl which carries the piperazine radical in the 2 position.

8. The compound as claimed in claim 5, in which Q is a radical of the formula

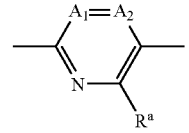

in which $A_1$ is N or CH and $A_2$ is CH and $R^a$ is selected from, C$_1$-C$_4$-alkoxy, NH$_2$, NHR$^6$, NR$^6$R$^7$ and C$_1$-C$_4$-haloalkoxy.

9. The compound as claimed in claim 8, in which the piperazine radical is located in the 2 position.

10. The compound as claimed in claim 1, in which the radical Ar carries a substituent $R^b$ in the para position and, optionally, a further substituent $R^b$ in the meta position or in the ortho position, in each case based on the binding site of the sulfonamide group.

11. The compound as claimed in claim 1, in which Ar is phenyl or pyridyl, which radicals possess one or 2 $R^b$ substituents.

12. The compound as claimed in claim 1, in which $R^1$ is not hydrogen or methyl.

13. The compound as claimed in claim 1 of the general formula Ia

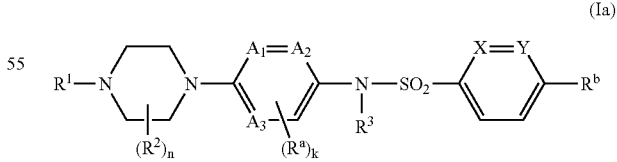

in which n, $R^1$, $R^2$, $R^3$, $R^a$ and $R^b$ have the meanings given in claim 1 and in which one of the variables $A_1$, $A_2$ or $A_3$ is $N_1$, the remaining two variables being CH or C—R$^a$, or $A_1$ and $A_3$ are N and $A_2$ is CH or C—R$^a$, with the proviso that k is 0 if two of the variables $A_1$, $A_2$ and $A_3$ are C—R$^a$, X and Y are selected frgom CH, C—R$^{b'}$ and N, in which $R^{b'}$ is halogen, methyl, CN, difluoromethyl or trifluoromethyl, with X and Y not simultaneously being N or simultaneously being C—R$^{b1}$, and k is 0 or 1.

14. The compound of the formula Ia as claimed in claim 13, in which k =0 and one of the variables $A_1$, $A_2$ or $A_3$ is N, the remaining two variables being CH or $A_1$ and $A_3$ are N and $A_2$ is CH.

15. The compound of the formula Ia as claimed in claim 14, in which $A_1$ is CH or N, $A_2$ is CH and $A_3$ is N.

16. The compound of the formula Ia as claimed in claim 13, in which k is 1, $A_1$ is CH or N, $A_2$ is CH and $A_3$ is N, and R$^a$ is selected from, $C_1$-$C_4$-alkoxy, $NH_2$, NHR$^6$, NR$^6$R$^7$ and $C_1$-$C_4$-haloalkoxy and R$^a$ is bound to the carbon atom adjacent to $A_3$.

17. The compound of the formula Ia as claimed in claim 13, in which n is 0 or 1 and, in the case of n=1, R$^2$ is bonded to the C atom of the piperazine ring which is adjacent to the group R$^1$—N and is a methyl group having the S configuration.

18. The compound of the formula Ia as claimed in claim 13, in which R$^1$ is not hydrogen or methyl.

19. The compound of the formula Ia as claimed in claim 13, of the general formula Ia.1

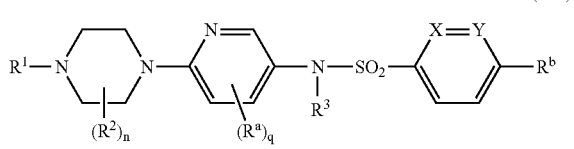

(Ia.1)

in which n, X, Y, R$^1$, R$^2$, R$^3$, R$^a$ and R$^b$ have the meanings given in claim 13 and q is 0, 1 or 2.

20. The compound of the formula Ia as claimed in claim 13, of the general formula Ia.2

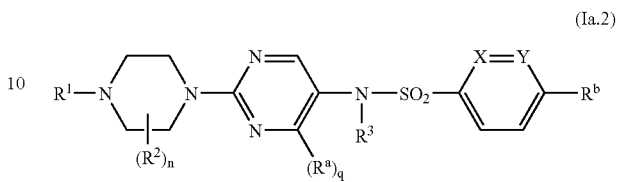

(Ia.2)

in which n, X, Y, R$^1$, R$^2$, R$^3$, R$^a$ and R$^b$ have the meanings given in claim 13 and q is 0 or 1.

21. A pharmaceutical composition which comprises at least one N-[(piperazinyl)hetaryl]arylsulfonamide compound as claimed in claim 1 and/or at least one physiologically tolerated acid addition salt of I and/or an N-oxide of I, together with physiologically acceptable carriers and/or auxiliary substances.

22. A method for treating a medical disorder susceptible to treatment with a dopamine $D_3$ receptor antagonist or a dopamine $D_3$ agonist selected from Parkinson's disease, and schizophrenia, one compound of the formula I of claim 1 to a subject in need thereof.

* * * * *

UNITED STATES PATENT AND TRADEMARK OFFICE
CERTIFICATE OF CORRECTION

PATENT NO. : 7,320,979 B2
APPLICATION NO. : 10/823317
DATED : January 22, 2008
INVENTOR(S) : Braje et al.

It is certified that error appears in the above-identified patent and that said Letters Patent is hereby corrected as shown below:

Column 65, line 12, delete "$C_3$-$C_8$" and insert --$C_3$-$C_6$--

Column 65, line 31, delete both instances of "$C_3$-$C_8$" and insert --$C_3$-$C_6$--

Column 66, line 63, delete "$N_1$" and insert --N--.

Signed and Sealed this

Seventeenth Day of June, 2008

JON W. DUDAS
*Director of the United States Patent and Trademark Office*